(12) United States Patent
Bischof et al.

(10) Patent No.: US 10,464,862 B2
(45) Date of Patent: Nov. 5, 2019

(54) OLIGOMERIZATION REACTIONS USING ALUMINOXANES

(71) Applicant: Chevron Phillips Chemical Company LP, The Woodlands, TX (US)

(72) Inventors: Steven M. Bischof, Humble, TX (US);
Jared T. Fern, Kingwood, TX (US);
Uriah J. Kilgore, Kingwood, TX (US);
Orson L. Sydora, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/719,107

(22) Filed: Sep. 28, 2017

(65) Prior Publication Data

US 2019/0092709 A1    Mar. 28, 2019

(51) Int. Cl.
*C07C 2/36* (2006.01)
*B01J 31/24* (2006.01)
(Continued)

(52) U.S. Cl.
CPC .............. *C07C 2/36* (2013.01); *B01J 31/143* (2013.01); *B01J 31/189* (2013.01);
(Continued)

(58) Field of Classification Search
CPC ... C07C 2/36; C07C 2531/24; C07C 2531/14; B01J 31/143; B01J 31/2438
See application file for complete search history.

(56) References Cited

U.S. PATENT DOCUMENTS

| | | |
|---|---|---|
| 3,361,525 A | 1/1968 | De Rycke et al. |
| 4,538,018 A | 8/1985 | Carter |

(Continued)

FOREIGN PATENT DOCUMENTS

| | | |
|---|---|---|
| CN | 1490291 A | 4/2004 |
| DE | 1146892 B | 4/1963 |

(Continued)

OTHER PUBLICATIONS

Imhoff et al., "Characterization of Methylaluminoxanes and Determination of trimethylaluminum Using Proton NMR", Organometallics 1998, 17, 1941-1945). (Year: 1998).*

(Continued)

*Primary Examiner* — In Suk C Bullock
*Assistant Examiner* — Ali Z Fadhel
(74) *Attorney, Agent, or Firm* — Conley Rose, P.C.

(57) ABSTRACT

Disclosed are processes for oligomerizing ethylene by contacting a catalyst system, ethylene, and optionally hydrogen to form an oligomer product in a reaction zone, wherein the catalyst system comprises: a chromium component comprising an $N^2$-phosphinyl amidine chromium compound complex, an $N^2$-phosphinyl formamidine chromium compound complex, and/or an $N^2$-phosphinyl guanidine chromium compound complex, and an aluminoxane; wherein the aluminoxane is characterized by 400 MHz proton NMR in which: (a) the ratio of peaks found in the range of –0.86 ppm to –0.74 ppm to peaks found in a range of –0.03 ppm to 0.07 ppm is less than or equal to 2.8:1; (b) the ratio of peaks found in the range of –0.03 ppm to 0.025 ppm to peaks found in a range of 0.025 ppm to 0.07 ppm is less than or equal to 15:1; and/or (c) the ratio of peaks found in a range of –0.86 ppm to –0.78 ppm to peaks found in the range of –0.78 ppm to –0.74 ppm is less than or equal to 6.5:1.

24 Claims, 6 Drawing Sheets

(51) Int. Cl.
*B01J 31/14* (2006.01)
*B01J 31/18* (2006.01)

(52) U.S. Cl.
CPC ........ *B01J 31/2438* (2013.01); *B01J 2231/20* (2013.01); *B01J 2531/62* (2013.01); *C07C 2531/14* (2013.01); *C07C 2531/24* (2013.01)

(56) References Cited

U.S. PATENT DOCUMENTS

| | | |
|---|---|---|
| 5,217,703 A | 6/1993 | Goodson |
| 7,276,566 B2 | 10/2007 | Muruganandam et al. |
| 7,300,904 B2 | 11/2007 | Dixon et al. |
| 7,361,623 B2 | 4/2008 | Dixon et al. |
| 7,554,001 B2 | 6/2009 | Dixon et al. |
| 7,994,363 B2 | 8/2011 | Gao et al. |
| 8,252,956 B2 | 8/2012 | Gao et al. |
| 8,367,786 B2 | 2/2013 | Dixon et al. |
| 8,680,003 B2 | 3/2014 | Sydora et al. |
| 8,865,610 B2 | 10/2014 | Sydora et al. |
| 9,283,555 B2 | 3/2016 | Sydora et al. |
| 9,707,549 B1 | 7/2017 | Kilgore et al. |
| 9,732,106 B2 | 8/2017 | Sydora et al. |
| 10,183,960 B1 | 1/2019 | Bischof et al. |
| 10,232,339 B2 | 3/2019 | Bischof et al. |
| 2002/0182124 A1 | 12/2002 | Woodard et al. |
| 2003/0195307 A1 | 10/2003 | Kaji et al. |
| 2004/0008572 A1 | 1/2004 | Stuart |
| 2004/0152935 A1 | 8/2004 | Jones et al. |
| 2005/0002841 A1 | 1/2005 | Moberg |
| 2006/0223960 A1* | 10/2006 | Jaber .................. C08F 10/00 526/153 |
| 2006/0247399 A1 | 11/2006 | McConville et al. |
| 2007/0185360 A1 | 8/2007 | Buchanan et al. |
| 2008/0207973 A1 | 8/2008 | Palmas et al. |
| 2010/0041841 A1 | 2/2010 | Terry et al. |
| 2010/0222622 A1 | 9/2010 | Overett et al. |
| 2010/0240847 A1* | 9/2010 | Dixon .................. B01J 31/188 526/161 |
| 2010/0274065 A1 | 10/2010 | Sydora |
| 2012/0142989 A1 | 6/2012 | Jaber et al. |
| 2012/0309965 A1* | 12/2012 | Sydora .................. C07F 9/46 544/64 |
| 2013/0090508 A1 | 4/2013 | Wang et al. |
| 2013/0331629 A1* | 12/2013 | Sydora .................. C07C 2/26 585/523 |
| 2015/0152200 A1 | 6/2015 | Hanton et al. |
| 2016/0375431 A1* | 12/2016 | Carney .................. C07F 9/46 585/513 |
| 2017/0341998 A1 | 11/2017 | Bischof et al. |
| 2017/0341999 A1 | 11/2017 | Fern et al. |
| 2017/0342000 A1 | 11/2017 | Bischof et al. |
| 2017/0342001 A1 | 11/2017 | Fern et al. |
| 2017/0349505 A1 | 12/2017 | Kilgore et al. |
| 2019/0091675 A1 | 3/2019 | Bischof et al. |
| 2019/0092708 A1 | 3/2019 | Bischof et al. |

FOREIGN PATENT DOCUMENTS

| | | |
|---|---|---|
| EP | 0780353 A1 | 6/1997 |
| EP | 2684857 A1 | 1/2014 |
| WO | 0204119 A1 | 1/2002 |
| WO | 2004056477 A1 | 7/2004 |
| WO | 2004056478 A1 | 7/2004 |
| WO | 2004056479 A1 | 7/2004 |
| WO | 2004056480 A1 | 7/2004 |
| WO | 2005039758 A1 | 5/2005 |
| WO | 2005123633 A1 | 12/2005 |
| WO | 2005123884 A2 | 12/2005 |
| WO | 2007007272 A2 | 1/2007 |
| WO | 2007088329 A1 | 8/2007 |
| WO | 2008014139 A2 | 1/2008 |
| WO | 2008119153 A1 | 10/2008 |
| WO | 2010034101 A1 | 4/2010 |
| WO | 2010034102 A1 | 4/2010 |
| WO | 2010051415 A1 | 5/2010 |
| WO | 2011130822 A1 | 10/2011 |
| WO | 2011137027 A1 | 11/2011 |
| WO | 2011140629 A1 | 11/2011 |
| WO | 2012051698 A1 | 4/2012 |
| WO | 2012071644 A1 | 6/2012 |
| WO | 2012092415 A1 | 7/2012 |
| WO | 2012142693 A1 | 10/2012 |
| WO | 2013168106 A1 | 11/2013 |
| WO | 2015094207 A1 | 6/2015 |
| WO | 2015097599 A1 | 7/2015 |
| WO | 2017010998 A1 | 1/2017 |
| WO | 2017011127 A1 | 1/2017 |
| WO | 2019067466 A1 | 4/2019 |

OTHER PUBLICATIONS

Office Action (Final) dated Feb. 6, 2018 (43 pages), U.S. Appl. No. 15/167,009, filed May 27, 2016.

Office Action (Final) dated Feb. 6, 2018 (53 pages), U.S. Appl. No. 15/167,024, filed May 27, 2016.

Bartlett, Stuart A., et al., "Activation of [CrCl3{R—Sn(H)S-R}] Catalysts for Selective Trimerization of Ethene: A Freeze-Quench Cr K-Edge XAFS Study," ACS Catalysis, Oct. 21, 2014, pp. 4201-4204, vol. 4, No. 11, American Chemical Society.

Bhaduri, Sumit, et al., "Density functional studies on chromium catalyzed ethylene trimerization," Journal of Organometallic Chemistry, Apr. 15, 2009, pp. 1297-1307, vol. 694, Elsevier B. V.

Britovsek, George, J. P.; "A DFT Mechanistic Study on Ethylene Tri- and Tetramerization with Cr/PNP Catalysts: Single versus Double Insertion Pathways," Chemistry A European Journal, Nov. 14, 2016, pp. 16891-16896, vol. 22, No. 47, Wiley-VCH Verlag GmbH & Co. KGaA, Weinheim.

Britovsek, George, J. P.; "Mechanistic study of ethylene tri- and tetramerisation with Cr/PNP catalysts: effects of additional donors," Catalysis Science & Technology, Oct. 28, 2016, pp. 8234-8241, vol. 6, No. 23, Royal Society of Chemistry.

Budzelaar, Peter H.M., "Ethene trimerization at CrI/CrIII—A Density functional theory (DFT) Study," Canadian Journal of Chemistry, 2009, pp. 832-837, vol. 87, Canadian Journal of Chemistry.

Filing receipt and specification for patent application entitled "Carbonyl-Containing Perfluorohydrocarbyl-N2-Phosphinyl Amidine Compounds, Chromium Salt Complexes and Their Use to Oligomerize Ethylene," by Steven M. Bischof, et al., filed Sep. 22, 2017 as U.S. Appl. No. 15/712,295.

Filing receipt and specification for patent application entitled "Perfluorohydrocarbyl-N2-Phosphinyl Amidine Compounds, Chromium Salt Complexes, Catalyst Systems, and Their Use to Oligomerize Ethylene," by Steven M. Bischof, et al., filed Sep. 22, 2017 as U.S. Appl. No. 15/712,304.

Filing receipt and specification for patent application entitled "Fluorinated N2-Phosphinyl Amidine Compounds, Chromium Salt Complexes, Catalyst Systems, and Their Use to Oligomerize Ethylene," by Steven M. Bischof, et al., filed Sep. 22, 2017 as U.S. Appl. No. 15/712,307.

Gong, Minglan, et al., "Selective Co-Oligomerization of Ethylene and 1-Hexene by Chromium-PNP Catalysts: A DFT Study," Organometallics, Mar. 29, 2016, pp. 972-981, vol. 35, No. 7, American Chemical Society.

Hossain, Anwar, et al., "Spin-crossover in Chromium-catalyzed Ethylene Trimerization Density Functional Theory Study," Bulletin of the Korean Chemical Society, Sep. 2014, pp. 2835-2838, vol. 35, No. 9, Korea Chemical Society.

Marenich, Aleksandr V., et al., "Universal Solvation Model Based on Solute Electron Density and on a Continuum Model of the Solvent Defined by the Bulk Dielectric Constant and Atomic Surface Tensions," Journal of Physical Chemistry B, Apr. 14, 2009, pp. 6378-6396, vol. 113, No. 18, American Chemical Society.

Qi, Yuan, et al., "Role of 1,2-Dimethoxyethane in the Transformation from Ethylene Polymerization to Trimerization Using Chromium Tris(2-ethylhexanoate)-Based Catalyst System: A DFT Study," Organometallics, Mar. 2, 2010, pp. 1588-1602, vol. 29, No. 7, American Chemical Society.

(56) References Cited

OTHER PUBLICATIONS

Van Rensburg, Werner Janse, et al., "A DFT Study toward the Mechanish of Chromium-Catalyzed Ethylene Trimerization," Organometallics, Feb. 17, 2004, pp. 1207-1222, vol. 23, No. 6, American Chemical Society.
Yang, Yun, et al., "Mechanistic DFT Study on Ethylene Trimerization of Chromium Catalysts Supported by a Versatile Pyrrole Ligand System," Organometallics, May 15, 2014, pp. 2599-2607, vol. 33, No. 10, American Chemical Society.
Fawcett, F.S., et al., "Cyanogen Fluoride: Synthesis and Properties," Journal of the American Chemical Society, Jul. 5, 1964, pp. 2576-2579, vol. 86, No. 13, American Chemical Society.
Office Action (Final) dated Feb. 28, 2018 (43 pages), U.S. Appl. No. 15/167,017, filed May 27, 2016.
Morse, J. G., et al., "Substituted Difluoro- and Dichlorophosphines," Inorganic Syntheses, 1967, pp. 147-156, vol. 10, McGraw-Hill Book Company, Inc.
Singh, Rajendra P., et al., "The first application of SelectfluorTM in electrophilic fluorination of amines: a new route to −NF2, −NHF, and >NF compounds," Chemical Communication, 2001, pp. 1196-1197, vol. 13, Royal Society of Chemistry.
Agapie, Theodor, et al., "Mechanistic Studies of Olefin and Alkyne Trimerization with Chromium Catalysts: Deuterium Labeling and Studies of Regiochemistry Using a Model Chromacyclopentane Complex," J. Am. Chem. Soc., 2007, pp. 14281-14295, vol. 129, No. 46, American Chemical Society.
Bollmann, Annette, et al., "Ethylene Tetramerization: A New Route to Produce 1-Octene in Exceptionally High Selectivities," J. Am. Chem. Soc., 2004, pp. 14712-14713, vol. 126, No. 45, American Chemical Society.
Carter, Anthea, et al., "High activity ethylene trimerisation catalysts based on diphospine ligands," Chemical Communications, vol. 8, 2002, pp. 858-859 plus 2 pages Supplementary Information.
Filing receipt and specification for patent application entitled "Fouling Protection for an Oligomerization Reactor Inlet," by Steven M. Bischof, et al., filed Jun. 6, 2017 as U.S. Appl. No. 15/615,113.
Group notation revised in periodic table, Feb. 4, 1985, C&EN, pp. 26-27.
McNaught, Alan D., et al., "Compendium of Chemical Terminology," IUPAC Recommendations, Second edition, 1997, 5 pages, Wiley-Blackwell.
Sydora, Orson L., et al., "Selective Ethylene Tri-/Tetramerization Catalysts," ACS Catalysis, 2012, pp. 2452-2455, vol. 2, American Chemical Society.
Office Action dated Apr. 25, 2017 (21 pages), U.S. Appl. No. 15/166,991, filed May 27, 2016.
Office Action dated Jul. 24, 2017 (33 pages), U.S. Appl. No. 15/167,009, filed May 27, 2016.
Foreign communication from a related counterpart application—International Search Report and Written Opinion, PCT/US2017/033165, dated Aug. 3, 2017, 11 pages.
Foreign communication from a related counterpart application—International Search Report and Written Opinion, PCT/US2017/033168, dated Aug. 3, 2017, 8 pages.
Office Action dated Aug. 2, 2017 (36 pages), U.S. Appl. No. 15/167,024, filed May 27, 2016.
Foreign communication from a related counterpart application—International Search Report and Written Opinion, PCT/US2017/032191, dated Aug. 14, 2017, 15 pages.
Kuhlmann, S,. et al,. "Chromium catalyzed tetramerization of ethylene in a continuous tube reactor—Proof of concept and kinetic aspects," Journal of Catalysis, 2009, pp. 83-91, vol. 262, No. 1, Elsevier Inc.
Office Action dated Aug. 30, 2017 (28 pages), U.S. Appl. No. 15/167,017, filed May 27, 2016.
Foreign communication from a related counterpart application—International Search Report and Written Opinion, PCT/US2017/032199, dated Aug. 17, 2017, 14 pages.
Office Action (Final) dated Nov. 1, 2017 (40 pages), U.S. Appl. No. 15/166,991, filed May 27, 2017.
AkzoNobel Product Data Sheet MMAO-3A/Heptane Solutions, 2014, 2 pgs.
AkzoNobel Safety Data Sheet MMAO-3A 7 wt% Al in Heptane, 2016, 17 pgs.
AkzoNobel Product Data Sheet MMA0-20/Heptane Solutions, 2014, 2 pgs.
AkzoNobel Safety Data Sheet MMAO-20 11-30% in Heptane, 2007, 9 pgs.
Kappler, B., et al., "Real-time Monitoring of Ethene/1-hexene Copolymerizations: Determination of Catalyst Activity, Copolymer Composition and Copolymerization Parameters," Polymer, 2003, vol. 44, pp. 6179-6186.
Office Action dated Jun. 28, 2018 (24 pages), U.S. Appl. No. 15/166,991, filed May 27, 2016.
Office Action dated Jul. 27, 2018 (24 pages), U.S. Appl. No. 15/167,017, filed May 27, 2016.
Office Action dated Jul. 17, 2018 (53 pages), U.S. Appl. No. 15/615,113, filed Jun. 6, 2017.
Office Action dated Aug. 2, 2018 (19 pages), U.S. Appl. No. 15/167,024, filed May 27, 2016.
Office Action dated Sep. 18, 2018 (31 pages), U.S. Appl. No. 15/712,295, filed Sep. 22, 2017.
Office Action dated Oct. 1, 2018 (26 pages), U.S. Appl. No. 15/167,009, filed May 27, 2016.
Foreign communication from a related counterpart application—International Search Report and Written Opinion, PCT/US2018/052709, dated Jan. 11, 2019, 12 pages.
Office Action (Final) dated Jan. 23, 2019 (25 pages), U.S. Appl. No. 15/166,991, filed May 27, 2016.
Notice of Allowance dated Jan. 29, 2019 (7 pages), U.S. Appl. No. 15/712,295, filed Sep. 22, 2017.
Office Action (Final) dated Feb. 13, 2019 (17 pages), U.S. Appl. No. 15/167,024, filed May 27, 2016.
Notice of Allowance dated Feb. 14, 2019 (9 pages), U.S. Appl. No. 15/167,009, filed May 27, 2016.
Foreign communication from a related counterpart application—International Search Report and Written Opinion, PCT/US2018/036068, dated Feb. 25, 2019, 15 pages.
Office Action dated Mar. 13, 2019 (58 pages), U.S. Appl. No. 16/262,164, filed Jan. 30, 2019.
Filing Receipt and Specification of U.S. Appl. No. 16/408,110, filed May 9, 2019, entitled, "Reduced Polymer Formation for Selective Ethylene Oligomerizations," 123 pages.
Notice of Allowance dated May 7, 2019 (8 pages), U.S. Appl. No. 15/167,024, filed May 7, 2019.
Notice of Allowance dated May 13, 2019 (13 pages), U.S. Appl. No. 15/166,991, filed May 27, 2016.
Restriction Requirement dated May 31, 2019 (10 pages), U.S. Appl. No. 15/712,307, filed Sep. 22, 2017.

* cited by examiner

OLIGOMERIZATION REACTIONS USING ALUMINOXANES

TECHNICAL FIELD

The present disclosure relates to processes for selective oligomerization of ethylene; more particularly, the present disclosure relates to processes for selective oligomerization of ethylene utilizing catalyst systems comprising a heteroatomic ligand chromium compound complex; still more particularly, the present disclosure relates to processes for selective oligomerization of ethylene utilizing catalyst systems formed via treatment of a heteroatomic ligand chromium compound complex with a modified methylaluminoxane having particular proton NMR peak ratios (e.g., MMAO-20).

BACKGROUND

The development of alpha olefin oligomerization techniques for the production of linear alpha olefins ($C_6$ to $C_{20}$) which do not utilize triethylaluminum (TEA) as part of the catalyst system has been a challenge. Both the economics and relative efficiency of TEA-based techniques have been difficult to match in alternative techniques. Some commercial success has been achieved using alternative techniques which use homogeneous catalyst systems; these techniques generally require extended secondary processing to recover the linear alpha olefins from undesired fractions/products such as butene or waxes.

Commercial selective olefins technology, based on pyrrole and PNP ligated chromium complexes, produce 1-hexene and/or 1-octene, without the generation of other undesirable fractions such as butene or waxes. The reaction mechanism operates via a unique metallocycle mechanism, with catalyst systems generated via treating a chromium compound/complex with an activator. These activators are typically based on materials such as aluminum alkyls, alkylaluminoxanes, borates, etc. Activation can be done in batch methodology prior to introducing the catalyst system to a reaction zone, or in a continuous method in which the components are mixed in a reaction zone, and then continuously added to a second reaction zone containing ethylene.

Improper activation can lead to a variety of undesired effects including, without limitation, the co-generation of by-products, such as cyclopentane(s), mixed $C_{10}$'s, $C_{12}$'s, and $C_{14}$'s, and polyethylene. The co-generation of polyethylene polymer can lead to reactor wall fouling that can cause reduced run time, loss of heat transfer for cooling the exothermic reaction, and poor overall reactor performance. Accordingly, there is an ongoing need for improved activators that provide for complete activation of chromium compounds while reducing the co-generation of undesired by-products.

SUMMARY

Disclosed herein are processes which include contacting a catalyst system, ethylene, and optionally hydrogen to form an oligomer product in a reaction zone, wherein the catalyst system comprises: a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and an aluminoxane; wherein the aluminoxane (e.g., a modified methylaluminoxane) can be characterized by 400 MHz proton NMR in which: (a) the ratio of peaks found in the range of −0.86 ppm to −0.74 ppm to peaks found in a range of −0.03 ppm to 0.07 ppm can be less than or equal to 2.8:1; (b) the ratio of peaks found in the range of −0.03 ppm to 0.025 ppm to peaks found in a range of 0.025 ppm to 0.07 ppm can be less than or equal to 15:1; (c) the ratio of peaks found in the range of −0.86 ppm to −0.78 ppm to peaks found in the range of −0.78 ppm to −0.74 ppm can be less than or equal to 6.5:1; or any combination thereof.

Further disclosed are processes which include contacting a catalyst system, ethylene, and optionally hydrogen to form an oligomer product in a reaction zone, wherein the catalyst system comprises a chromium component comprising an $N^2$-phosphinyl amidine chromium compound complex, an $N^2$-phosphinyl formamidine chromium compound complex, an $N^2$-phosphinyl guanidine chromium compound complex, or any combination thereof and an aluminoxane, wherein the aluminoxane comprises MMAO-20.

Further disclosed are processes which include contacting ethylene, an aluminoxane, a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and optionally hydrogen to form an oligomer product in a reaction zone, wherein the aluminoxane (e.g., a modified methylaluminoxane) is characterized by 400 MHz proton NMR in which: (a) the ratio of peaks found in the range of −0.86 ppm to −0.74 ppm to peaks found in a range of −0.03 ppm to 0.07 ppm can be less than or equal to 2.8:1; (b) the ratio of peaks found in the range of −0.03 ppm to 0.025 ppm to peaks found in a range of 0.025 ppm to 0.07 ppm can be less than or equal to 15:1; (c) the ratio of peaks found in the range of −0.86 ppm to −0.78 ppm to peaks found in the range of −0.78 ppm to −0.74 ppm can be less than or equal to 6.5:1; or any combination thereof.

Further disclosed are processes which include contacting ethylene, an aluminoxane, a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and optionally hydrogen to form an oligomer product in a reaction zone, wherein the aluminoxane comprises MMAO-20.

BRIEF DESCRIPTION OF THE DRAWINGS

For a detailed description, reference will now be made to the accompanying drawings.

DETAILED DESCRIPTION

Figure 1A:
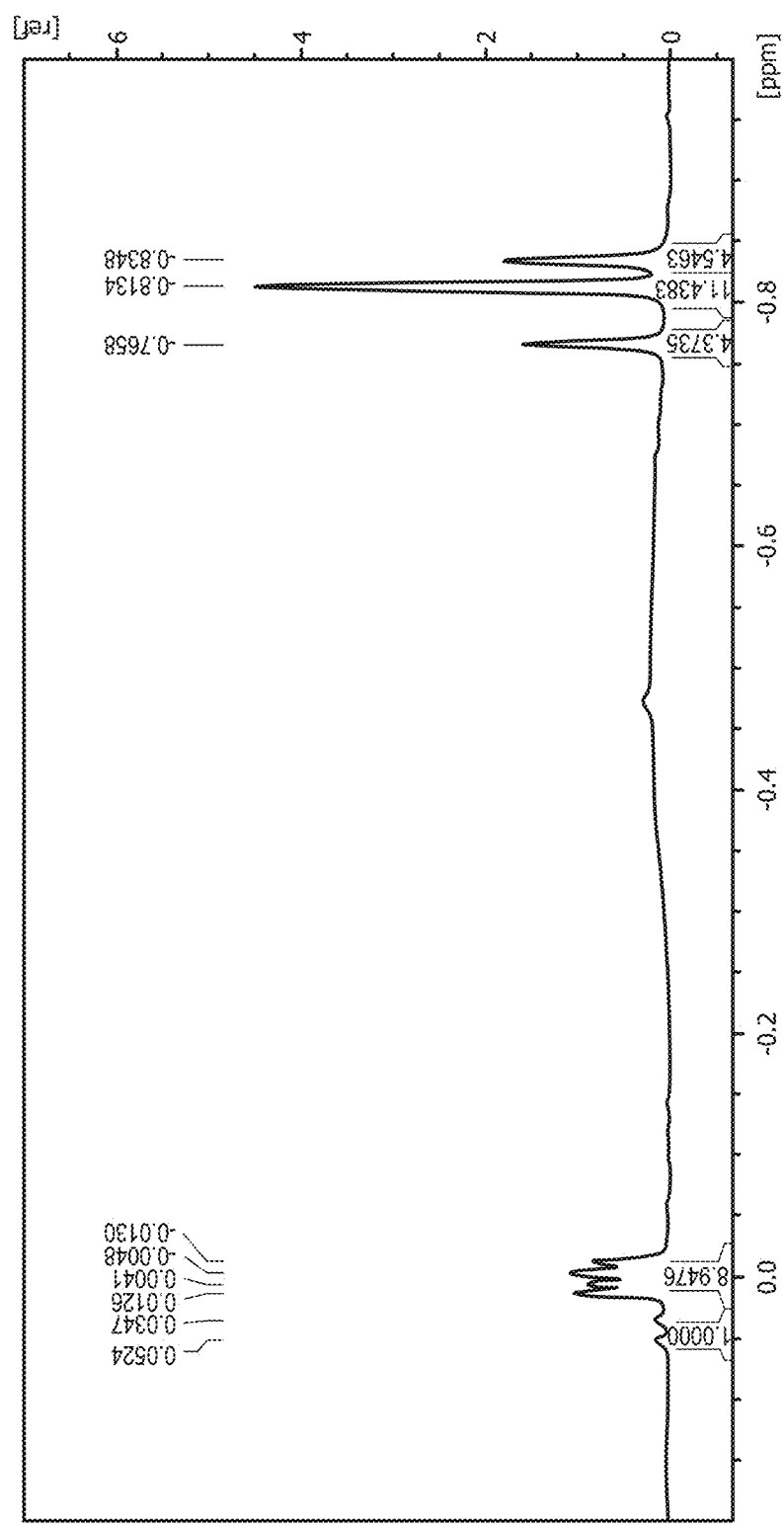
FIG. 1A shows $^1$H NMR (400 MHz) spectra for MMAO-20.

In the description, various ranges and/or numerical limitations can be expressly stated herein. It should be recognized that unless stated otherwise, it is intended that endpoints are to be interchangeable. Further, any ranges include iterative ranges of like magnitude falling within the expressly stated ranges or limitations.

Furthermore, various modifications can be made within the scope of the invention(s) as herein intended, and embodiments of the invention can include combinations of features other than those expressly claimed. In particular, flow arrangements other than those expressly described herein are within the scope of the invention(s). Additionally, aspects and/or embodiments can be combined to describe further inventions which are fully contemplated by the present disclosure.

Unless otherwise specified, the terms "contact" and "combine," and their derivatives, can refer to any addition sequence, order, or concentration for contacting or combining two or more components of the disclosed aspects and/or embodiments. Combining or contacting of oligomerization components can occur in one or more reaction zones under suitable contact conditions such as temperature, pressure, contact time, flow rates, etc.

Regarding claim transitional terms or phrases, the transitional term "comprising", which is synonymous with "including," "containing," "having" or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter composition or method to which the term is applied. For example, a feedstock consisting of a material A can include impurities typically present in a commercially produced or commercially available sample of material A. When a claim includes different features and/or feature classes (for example, a method step, feedstock features, and/or product features, among other possibilities), the transitional terms comprising, consisting essentially of, and consisting of apply only to the feature class that is utilized and it is possible to have different transitional terms or phrases utilized with different features within a claim. For example, a method can comprise several recited steps (and other non-recited steps) but utilize a catalyst system preparation consisting of specific steps can utilize a catalyst system comprising recited components and other non-recited components.

Within this specification, use of "comprising" or an equivalent expression contemplates the use of the phrase "consisting essentially of," "consists essentially of," or equivalent expressions as alternative embodiments to the open-ended expression. Additionally, use of "comprising" or an equivalent expression or use of "consisting essentially of" in the specification contemplates the use of the phrase "consisting of," "consists of," or equivalent expressions as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

While compositions and methods are described in terms of "comprising" various components or steps, the compositions and methods can also "consist essentially of or" consist of the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

Unless otherwise indicated, the definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in *Chemical and Engineering News,* 63(5), 27, 1985. In some instances, a group of elements can be indicated using a common name assigned to the group; for example, alkali metals for Group 1 elements, alkaline earth metals (or alkaline metals) for Group 2 elements, transition metals for Groups 3-12 elements, and halogens for Group 17 elements.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to hexene includes 1-hexene, 2-hexene, 3-hexene, and any other hydrocarbon having 6 carbon atoms (linear, branched or cyclic) and a single carbon-carbon double bond. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials that have three or more hydrogen atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group in an $N^2$-phosphinyl amidine can be an inert functional group because a single metal compound cannot complex with both the para ether group and the $N^2$-phosphinyl amidine group in a single metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc. . . . such multiple bonds can be identified by use of the term "mono," "di," "tri," etc. . . . within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms and additional double bonds.

The term "reaction zone effluent," and it derivatives generally refers to all materials which exit the reaction zone through a reaction zone outlet which discharges a reaction mixture and can include reaction system feed(s) (e.g., ethylene, catalyst system or catalyst system components, and/or organic reaction medium), and/or reaction product(s) (e.g., oligomer product including oligomers and non-oligomers). The term "reaction zone effluent" and its derivatives can be qualified to refer to certain portions by use of additional qualifying terms. For example, while reaction zone effluent refers to all material which exits the reaction system through the reaction zone outlet/discharge, a reaction zone oligomer product effluent refers to only the oligomer product within the reaction zone effluent.

The terms "room temperature" or "ambient temperature" are used herein to describe any temperature from 15° C. to 35° C. wherein no external heat or cooling source is directly applied. Accordingly, the terms "room temperature" and "ambient temperature" encompass the individual temperatures and any and all ranges, subranges, and combinations of subranges of temperatures from 15° C. to 35° C. wherein no external heating or cooling source is directly applied. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" for the feature disclosed herein.

Within this disclosure the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. References to compounds or groups having substitution at positions in addition to the indicated position can be referenced using comprising or some other alternative language. For example, a reference to a phenyl group comprising a substituent at the 4 position refers to a phenyl group having a non-hydrogen substituent group at the 4 position and hydrogen or any non-hydrogen group at the 2, 3, 5, and 6 positions.

Use of the term "optionally" with respect to any element of a claim is intended to mean that the subject element is required, or alternatively, is not required. Both alternatives are intended to be within the scope of the claim.

Processes described herein can utilize steps, features, compounds and/or equipment which are independently described herein. The processes described herein may or may not utilize step identifiers (e.g., 1), 2), etc., a), b), etc., i), ii), etc., or first, second etc., among others), feature identifiers (e.g., 1), 2), etc., a), b), etc., i), ii), etc., or first, second etc., among others), and/or compound and/or composition identifiers (e.g., 1), 2), etc., a), b), etc., i), ii), etc., or first, second etc., among others). However, it should be noted that processes described herein can have multiple steps, features (e.g. reagent ratios, formation conditions, among other considerations), and/or multiple compounds and/or composition using no descriptor or sometimes having the same general identifier. Consequently, it should be noted that the processes described herein can be modified to use an appropriate step or feature identifier (e.g., 1), 2), etc., a), b), etc., i), ii), etc., or first, second etc., among others), feature identifier (e.g., 1), 2), etc., a), b), etc., i), ii), etc., or first, second etc., among others), and/or compound identifier (e.g., first, second, etc.) regardless of step, feature, and/or compound identifier utilized in the a particular aspect and/or embodiment described herein and that step or feature identifiers can be added and/or modified to indicate individual different steps/features/compounds utilized within the processes without detracting from the general disclosure.

Processes for forming oligomer products are described herein. Such processes generally comprise contacting ethylene and a catalyst system to form an oligomer product under oligomerization conditions. As used herein, the term "oligomerization" and its derivatives, refers to processes which produce a mixture of products containing at least 70 weight percent products containing from 2 to 30 ethylene units. Similarly, as used herein, an "oligomer" is a product that contains from 2 to 30 ethylene units while an "oligomer product" includes all products made by the process including the "oligomers" and products which are not "oligomers" (e.g., products which contain more than 30 monomer units). Further the terms "oligomer product" and "oligomerization product" can be used interchangeably.

As used herein, the term "trimerization," and it derivatives, refers to a process which produces a mixture of products containing at least 70 weight percent products containing three and only three ethylene units. As used herein a "trimer" is a product which contains three and only three ethylene units while a "trimerization product" includes all products made by the trimerization process including trimer and product which are not trimers (e.g. dimers or tetramers). Generally, a "trimerization" process using ethylene produces an oligomer product containing at least 70 weight percent hexene(s).

As used herein, the term "tetramerization," and its derivatives, refers to a process which produces a mixture of products containing at least 70 weight percent products containing four and only four ethylene units. As used herein a "tetramer" is a product which contains four and only four ethylene units while a "tetramerization product" includes all products made by the tetramerization process including tetramer and products which are not tetramers (e.g. dimers or trimer). Generally, a "tetramerization" process using ethylene produces an oligomer product containing at least 70 weight percent octene(s).

As used herein, the term "trimerization and tetramerization," and it derivatives, refers to a process which produces an oligomer product containing at least 70 weight percent products containing three and/or four and only three and/or four ethylene units. As used herein a "trimerization and tetramerization product" includes all products made by the "trimerization and tetramerization" process including trimer, tetramer, and products which are not trimers or tetramers (e.g. dimers). Generally, a "trimerization and tetramerization" process using ethylene produces an oligomer product containing at least 70 weight percent hexene(s) and/or octene(s).

Aspects disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

Disclosed herein are processes for the oligomerization of ethylene to form an oligomer product. In an embodiment, the oligomer product can comprise normal alpha olefins (NAO). In particular, the processes described herein can selectively trimerize, tetramerize, or trimerize and tetramerize ethylene to produce an oligomer product containing hexenes (e.g., 1-hexene) and/or octenes (e.g., 1-octene).

In an embodiment, the processes disclosed herein can comprise contacting a catalyst system, ethylene, and optionally hydrogen to form an oligomer product in a reaction zone, wherein the catalyst system comprises: a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and an aluminoxane. In other embodiments, the processes disclosed herein can comprise contacting ethylene, an aluminoxane, a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and optionally hydrogen to form an oligomer product in a reaction zone. Aspects and embodiments of the herein described processes can utilize a catalyst system comprising i) a chromium component comprising an $N^2$-phosphinyl formamidine chromium compound complex, an $N^2$-phosphinyl amidine chromium compound complex, an $N^2$-phosphinyl guanidine chromium compound complex, or any combination thereof, and ii) an aluminoxane. In some embodiments, the catalyst system can comprise i) a chromium component comprising an $N^2$-phosphinyl formamidine chromium compound complex and ii) an aluminoxane; alternatively, i) a chromium component comprising an $N^2$-phosphinyl amidine chromium compound complex and ii) an aluminoxane; or alternatively, i) a chromium component comprising an $N^2$-phosphinyl guanidine chromium compound complex and ii) an aluminoxane. In an embodiment, the process can further include contacting an organic reaction medium with the catalyst system, ethylene, and optionally hydrogen; or alternatively, the chromium component, the aluminoxane, ethylene, and optionally hydrogen. Generally, the $N^2$-phosphinyl amidine chromium compound complex, the $N^2$-phosphinyl formamidine chromium compound complex, the $N^2$-phosphinyl guanidine chromium compound complex, the aluminoxane, the organic reaction medium, and any other element of the catalyst system described herein are independent elements of the catalyst systems. These catalyst system elements are independently described herein and can be utilized without limitation, and in any combination, to further describe a catalyst system utilized in aspects and/or embodiments of the processes described herein.

Aluminoxane

Generally, the aluminoxane utilized in the catalyst systems and/or the processes described herein can be any aluminoxane which can, in conjunction with the $N^2$-phosphinyl formamidine chromium compound complex, the $N^2$-phosphinyl amidine chromium compound complex, and/ or the $N^2$-phosphinyl guanidine chromium compound complex, catalyze the formation of an oligomer product. In a non-limiting embodiment, the aluminoxane can have a repeating unit characterized by the Formula I:

Formula I wherein R' is a linear or branched alkyl group. Alkyl groups for the aluminoxanes are independently described herein and can be utilized without limitation to further describe the aluminoxanes having Formula I. Generally, n of Formula I can be greater than 1; or alternatively, greater than 2. In an embodiment, n can range from 2 to 15; or alternatively, range from 3 to 10.

In an aspect, each alkyl group of the aluminoxane independently can be, comprise, or consist essentially of, a $C_1$ to $C_{20}$ alkyl group; alternatively, a $C_1$ to $C_{10}$ alkyl group; or alternatively, a $C_1$ to $C_6$ alkyl group. In an embodiment, each alkyl group of the aluminoxane independently can be, comprise, or consist essentially of, a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some embodiments, each alkyl group or the aluminoxane independently can be, comprise, or consist essentially of, a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In a non-limiting embodiment, the aluminoxane can be, comprise, or consist essentially of, methylaluminoxane (MAO), ethylaluminoxane, a modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-pentylaluminoxane, 3-pentyl-aluminoxane, iso-pentyl-aluminoxane, neopentylaluminoxane, or mixtures thereof. In some non-limiting embodiments, the aluminoxane can be, comprise, or consist essentially of, methylaluminoxane (MAO), a modified methylaluminoxane (MMAO), isobutyl aluminoxane, t-butyl aluminoxane, or mixtures thereof. In other non-limiting embodiments, the aluminoxane can be, comprise, or consist essentially of, methylaluminoxane (MAO); alternatively, ethylaluminoxane; alternatively, a modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentylaluminoxane. In an embodiment, the aluminoxane can comprise, or consist essentially of MMAO-20.

In an embodiment, the aluminoxane (e.g., a modified methylaluminoxane) can be characterized by 400 MHz proton NMR. In some embodiments, the aluminoxane (e.g., methylaluminoxane) can have (a) a specified ratio of peaks found in a range of −0.86 ppm to −0.74 ppm to peaks found in a range of −0.03 ppm to 0.07 ppm, (b) a specified ratio of peaks found in a range of −0.03 ppm to 0.025 ppm to peaks found in a range of 0.025 ppm to 0.07 ppm, (c) a specified ratio of peaks found in a range of −0.86 ppm to −0.78 ppm to peaks found in the range of −0.78 ppm to −0.74 ppm, or (d) any combination thereof; or alternatively, (a) a specified ratio of peaks found in a range of −0.86 ppm to −0.74 ppm to peaks found in a range of −0.03 ppm to 0.07 ppm, (b) a specified ratio of peaks found in a range of −0.03 ppm to 0.025 ppm to peaks found in a range of 0.025 ppm to 0.07 ppm, and (c) a specified ratio of peaks found in a range of −0.86 ppm to −0.78 ppm to peaks found in the range of −0.78 ppm to −0.74 ppm. In some embodiments the ratio of peaks found in the range of −0.86 ppm to −0.74 ppm to peaks found in a range of −0.03 ppm to 0.07 ppm can be less than or equal to 2.8:1, less than or equal to 2.6:1, less than or equal to 2.4:1, in the range or 0.4:1 to 2.8:1, in the range of 0.6:1 to 2.6:1, or in the range from 0.8:1 to 2.4:1. In some embodiments, the ratio of peaks found in the range of −0.03 ppm to 0.025 ppm to peaks found in a range of 0.025 ppm to 0.07 ppm can be less than or equal to 15:1, less than or equal to 13:1, less than or equal to 11:1, in the range of 1:1 to 15:1, in the range of 2:1 to 13:1, or in the range of 3:1 to 11:1. In some embodiments, the ratio of peaks found in the range of −0.86 ppm to −0.78 ppm to peaks found in the range of −0.78 ppm to −0.74 ppm is less than or equal to 6.5:1, less than or equal to 6:1, less than or equal to 5.5:1, in the range of 0.5:1 to 6.5:1, in the range of 1:1 to 6:1, or in a range from 1.5:1 to 5.5:1. The ratios of peaks are determined as the ratios of the peak areas (i.e. area ratio) of the peak ranges described herein. Generally, the 400 MHz proton NMR peak positions are determined by using the downfield residual proton resonance of deuterated tetrahydrofuran as the internal standard where the downfield residual proton resonance quintet of deuterated tetrahydrofuran peak position was set at 3.62 ppm. One such aluminoxane (e.g., methylaluminoxane) that can have the desired 400 MHz proton NMR characteristics is MMAO-20, available from AkzoNobel Functional Chemicals B.V., Netherlands. The Product Data Sheet for MMAO-20, OMS 61685.01/December 2014, provides the product description and compositional information about MMAO-20 provided in Table 1 below. This product description and composition information can be utilized in any aspect or embodiment disclosed herein to further describe the aluminoxane (e.g., a modified methylaluminoxane) having the desired 400 MHz proton NMR characteristics described herein.

TABLE 1

Composition and Product Description for an Aluminoxane
(e.g., Modified Methylaluminoxane)
having Desired 400 MHz Proton NMR Characteristics

| Product Description | | Composition[a] | |
|---|---|---|---|
| Approx. Molecular Formula | $[(CH_3)_{0.7}(isoC_4H_9)_{0.3}AlO]_n$ | Methane, molar %[b] | 62.0-78.0 |
| Process Route | hydrolytic | Isobutane, molar %[b] | 22.0-38.0 |
| Approx. Molecular Weight | 70.7 | Hydrogen, molar %[b] | 3.0 max |
| CAS No. | 146905-79-5 | Others, molar %[b, c] | 3.0 max |
| EINECS/ELINCS no. | 931-024-8 | Aluminum, wt. %[d] | 6.0-8.0 |
| | | Active Al[e] | 36-48 |

[a]Data for heptane solution containing 7 wt. % aluminum.
[b]Calculated by gas chromatography of hydrocarbons and hydrogen obtained upon hydrolysis of aluminoxane.
[c]Other components include ethane, propane, isobutylene, and n-butane
[d]Determined by titration of aqueous hydrolyzate.
[e]Determined by pyridine titration method.

In an embodiment, the $N^2$-phosphinyl formamidine chromium compound complex utilized in the catalyst systems described herein can comprise, can consist essentially of, or can be, an $N^2$-phosphinyl formamidine chromium compound complex having the Structure NPFCr1. In an embodiment, the $N^2$-phosphinyl amidine chromium compound complex utilized in the catalyst systems described herein can comprise, can consist essentially of, of can be, an $N^2$-phosphinyl amidine chromium compound complex having the Structure NPACr1 or Structure NPACr2; alternatively, Structure NPACr1; or alternatively Structure NPACr2. In an embodiment, the $N^2$-phosphinyl guanidine chromium compound complex utilized in the catalyst systems described herein can comprise, can consist essentially of, or can be, an $N^2$-phosphinyl guanidine chromium compound complex having the Structure GuCr1, GuCr2, GuCr3, GuCr4, or GuCr5; alternatively, an $N^2$-phosphinyl guanidine chromium compound complex having the Structure GuCr1; alternatively, an $N^2$-phosphinyl guanidine chromium compound complex having the Structure GuCr2; alternatively, an $N^2$-phosphinyl guanidine chromium compound complex having the Structure GuCr3; alternatively, an $N^2$-phosphinyl guanidine chromium compound complex having the Structure GuCr4; or alternatively, an $N^2$-phosphinyl guanidine chromium compound complex having the Structure GuCr5.

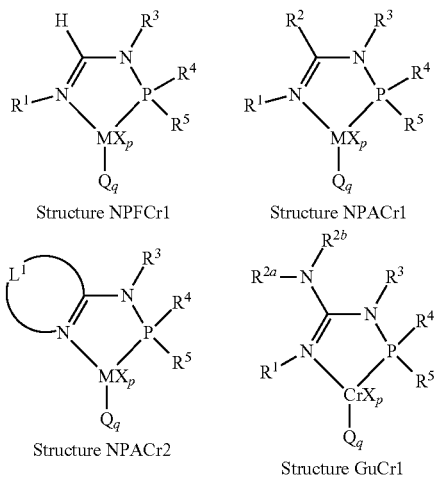

Structure NPFCr1

Structure NPACr1

Structure NPACr2

Structure GuCr1

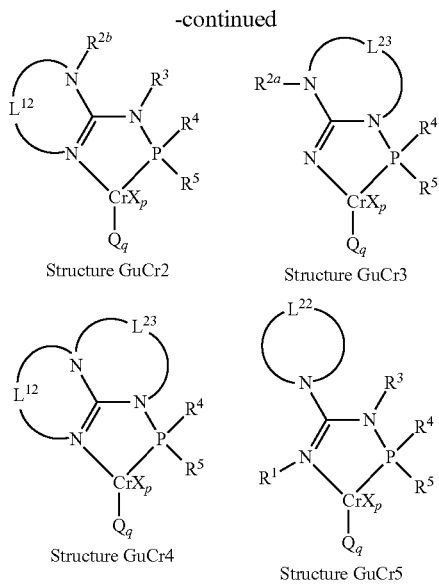

Structure GuCr2

Structure GuCr3

Structure GuCr4

Structure GuCr5

Within the $N^2$-phosphinyl formamidine chromium compound complexes and the $N^2$-phosphinyl amidine chromium compound complexes, the nitrogen participating in a double bond with the central carbon atom is referred to as the $N^1$ nitrogen and the nitrogen atom participating in a single bond with the central carbon atom is referred to as the $N^2$ nitrogen. Similarly, within the $N^2$-phosphinyl guanidine chromium compound complexes, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that the guanidine group of the guanidine in the $N^2$-phosphinyl guanidine transition metal complexes can be a portion of a larger group which does not contain guanidine in its name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having a guanidine group) since it contains the defined general structure of the guanidine compound.

$R^1$, $R^3$, $R^4$, and/or $R^5$ within the $N^2$-phosphinyl formamidine chromium compound complexes having Structure NPFCr1 are independently described herein and can be utilized without limitation to further describe the $N^2$-phosphinyl formamidine chromium compound complexes having Structure NPFCr1. Similarly, $R^1$, $R^2$ $R^3$, $R^4$, and/or $R^5$ within the $N^2$-phosphinyl amidine chromium compound complexes having Structure NPACr1 are independently described herein and can be utilized without limitation to further describe the $N^2$-phosphinyl amidine chromium compound complexes having Structure NPACr1. Similarly, L1, $R^3$, $R^4$, and/or $R^5$ within the $N^2$-phosphinyl amidine chromium compound complexes having Structure NPACr2 are independently described herein and can be utilized without limitation to further describe the $N^2$-phosphinyl amidine chromium compound complexes having Structure NPACr2. Similarly, $R^1$, $R^{2a}$, $R^{2b}$, $R^3$, $R^4$, $R^5$, $L^{12}$, $L^{22}$, and/or $L^{23}$ within the respective $N^2$-phosphinyl guanidine chromium compound complexes having the Structures GuCr1, GuCr2, GuCr3, GuCr4, or GuCr5 which have an $R^1$, $R^{2a}$, $R^{2b}$, $R^3$, $R^4$, $R^5$, $L^{12}$, $L^{22}$, and $L^{23}$ are independently described herein and can be utilized without limitation to further describe the respective $N^2$-phosphinyl guanidine chromium compound complexes having the Structures GuCr1, GuCr2, GuCr3, GuCr4, and/or GuCr5 which have an $R^1$, $R^{2a}$, $R^{2b}$, $R^3$, $R^4$, $R^5$, $L^{12}$, $L^{22}$, and $L^{23}$. $MX_p$, Q, and q of the $N^2$-phosphinyl formamidine chromium compound complexes, the $N^2$-phosphinyl amidine chromium compound complexes, and the $N^2$-phosphinyl guanidine chromium compound complexes are independently described herein and can be utilized in any combination, and without limitation, to further describe the $N^2$-phosphinyl formamidine chromium compound complexes, the $N^2$-phosphinyl amidine chromium compound complexes, and the $N^2$-phosphinyl guanidine chromium compound complexes. Additionally, $MX_p$, Q, and q can be combined, without limitation, with the independently described $R^1$, $R^2$, $R^{2a}$, $R^{2b}$, $R^3$, $R^4$, $R^5$, $L^1$, $L^{12}$, $L^{22}$, and $L^{23}$ to further describe the appropriate $N^2$-phosphinyl formamidine chromium compound complexes, the appropriate $N^2$-phosphinyl amidine chromium compound complexes, and the appropriate $N^2$-phosphinyl guanidine chromium compound complexes described herein which have an $R^1$, $R^2$, $R^{2a}$, $R^{2b}$, $R^3$, $R^4$, $R^5$, $L^1$, $L^{12}$, $L^{22}$, and/or $L^{23}$.

Generally, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an organyl group; alternatively, an organyl group consisting essentially of inert functional groups; or alternatively, a hydrocarbyl group. In an embodiment, the $R^1$ organyl group of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ organyl group. In an embodiment, the $R^1$ organyl group consisting essentially of inert functional groups of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the $R^1$ hydrocarbyl group of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ hydrocarbyl group.

In an embodiment, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group, a substituted alkyl group, a cycloalkyl group, a substituted cycloalkyl group, an aryl group, a substituted aryl group, an aralkyl group, or a substituted aralkyl group. In some embodiments, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, the alkyl group which can be utilized as $R^1$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^1$ can be a $C_1$ to $C_{20}$, a $C_1$ to $C_{10}$, or a $C_1$ to $C_5$ substituted alkyl group. In any aspect or embodiment disclosed herein, the cycloalkyl group which can be utilized as $R^1$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^1$ can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^1$ can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^1$ can be a $C_6$ to $C_{20}$, a $C_6$ to $C_{15}$, or a $C_6$ to $C_{10}$ substituted aryl group. In any aspect or embodiment disclosed herein, the aralkyl group which can be utilized as $R^1$ can be a $C_7$ to $C_{20}$, a $C_7$ to $C_{15}$, or a $C_7$ to $C_{10}$ aralkyl group. In any aspect or embodiment disclosed herein, the substituted aralkyl group which can be utilized as $R^1$ can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^1$.

In an embodiment, $R^1$ can be a methyl group, an ethyl group, a propyl group, a butyl group, a pentyl group, a hexyl group, a heptyl group, or an octyl group. In some embodiments, $R^1$ can be a methyl group, an ethyl group, a n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^1$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^1$.

In an embodiment, $R^1$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized as $R^1$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; alternatively, a 2,6-disubstituted cyclohexyl group or a 2,5-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,5-disubstituted cyclopentyl group. In an embodiment, one or more substituents of a multi-substituted cycloalkyl group utilized as $R^1$ can be the same or different; alternatively, all the substituents of a multi-substituted cycloalkyl group can be the same; or alternatively, all the substituents of a multi-substituted cycloalkyl group can be different. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group (general or specific) which can be utilized as $R^1$.

In a non-limiting embodiment, $R^1$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, or a 2,5-dialkylcyclopentyl group. Alkyl substituent groups (general and specific) are independently described herein and these alkyl substituent groups can be utilized, without limitation, to further describe alkylcyclohexyl groups (general and specific), dialkylcyclohexyl groups (general and specific), alkylcyclopentyl groups (general or specific), and/or dialkylcyclopentyl groups (general and specific) which can be utilized as $R^1$. Generally, the alkyl substituents of a dialkylcyclohexyl group or a dialkylcyclopentyl group can be the same; or alternatively, the alkyl substituents of a dialkylcyclohexyl group or a dialkylcyclopentyl group can be different. In some non-limiting embodiments, $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, $R^1$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^1$ can be a phenyl group, a substituted phenyl group; alternatively, a phenyl group; or alternatively, a substituted phenyl group. In an embodiment, the substituted phenyl group, which can be utilized as $R^1$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^1$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^1$.

In a non-limiting embodiment, $R^1$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^1$. Generally, the alkyl substituents of a dialkylphenyl group (general or specific) or a trialkylphenyl group (general or specific) can be the same; or alternatively, the alkyl substituents of a dialkylphenyl group or trialkylphenyl group can be different. In some non-limiting embodiments, $R^1$ can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In an embodiment, $R^1$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^1$.

Generally, $R^2$ of the $N^2$-phosphinyl amidine chromium compound complexes can be an organyl group; alternatively, an organyl group consisting essentially of inert functional groups; or alternatively, a hydrocarbyl group. In an embodiment, $R^2$ organyl group of the $N^2$-phosphinyl amidine chromium compound complexes can be a $C_1$ to $C_{20}$, a $C_1$ to $C_{15}$, a $C_1$ to $C_{10}$, or a $C_1$ to $C_5$ organyl group. In an embodiment, $R^2$ organyl group consisting essentially of inert functional groups of the $N^2$-phosphinyl amidine chromium compound complexes can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, $R^2$ hydrocarbyl group of the $N^2$-phosphinyl amidine chromium compound complexes can be a $C_1$ to $C_{20}$, a $C_1$ to $C_{15}$, a $C_1$ to $C_{10}$, or a $C_1$ to $C_5$ hydrocarbyl group.

In an embodiment, $R^2$ of the $N^2$-phosphinyl amidine chromium compound complexes can be an alkyl group, a substituted alkyl group, a cycloalkyl group, a substituted cycloalkyl group, an aryl group, a substituted aryl group, an aralkyl group, or a substituted aralkyl group. In some embodiments, $R^2$ of the $N^2$-phosphinyl amidine chromium compound complexes can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^2$ of the $N^2$-phosphinyl amidine chromium compound complexes can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, the alkyl group which can be utilized as $R^2$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^2$ can be a $C_1$ to $C_{20}$, a $C_1$ to $C_{10}$, or a $C_1$ to $C_5$ substituted alkyl group. In any aspect or embodiment disclosed herein, the cycloalkyl group which can be utilized as $R^2$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^2$ can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^2$ can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^2$ can be a $C_6$ to $C_{20}$, a $C_6$ to $C_{15}$, or a $C_6$ to $C_{10}$ substituted aryl group. In any aspect or embodiment disclosed herein, the aralkyl group which can be utilized as $R^2$ can be a $C_7$ to $C_{20}$, a $C_7$ to $C_{15}$, or a $C_7$ to $C_{10}$ aralkyl group. In any aspect or embodiment disclosed herein, the substituted aryl group which can be utilized as $R^2$ can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^2$.

In an embodiment, $R^2$ can be a methyl group, an ethyl group, a propyl group, a butyl group, a pentyl group, a hexyl group, a heptyl group, or an octyl group. In some embodiments, $R^2$ can be a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^2$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^2$.

In an embodiment, $R^2$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized as $R^2$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; alternatively, a 2,6-disubstituted cyclohexyl group or a 2,5-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,5-disubstituted cyclopentyl group. In an embodiment, one or more substituents of a multi-substituted cycloalkyl group utilized as $R^2$ can be the same or different; alternatively, all the substituents of a multi-substituted cycloalkyl group can be the same; or alternatively, all the substituents of a multi-substituted cycloalkyl group can be different. Each substituent of a cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^2$.

In a non-limiting embodiment, $R^2$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^2$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting embodiments, $R^2$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, $R^2$ can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^2$ can be a phenyl group, a substituted phenyl group; alternatively, a phenyl group; or alternatively, a substituted phenyl group. In an embodiment, the substituted phenyl group, which can be utilized as $R^2$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^2$ can be the same or different; alternatively, all the substituents of a multi-substituted cycloalkyl group can be the same; or alternatively, all the substituents of a multi-substituted cycloalkyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^2$.

In a non-limiting embodiment, $R^2$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4- dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^2$. Generally, the alkyl substituents of a dialkylphenyl group (general or specific) or trialkylphenyl group (general or specific) can be the same; or alternatively, the alkyl substituents of a dialkylphenyl group or trialkylphenyl group can be different. In some non-limiting embodiments, $R^2$ can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, $R^2$ can be a phenyl group, a 2-alkoxyphenyl group, or a 4-alkoxyphenyl group. In some non-limiting embodiments, $R^2$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiment, $R^2$ can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some embodiments, $R^2$ can be a phenyl group, a 2-fluorophenyl group, a 4-fluorophenyl group, or a 2,6-difluorophenyl group.

In an embodiment, $R^2$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group which can be utilized as $R^2$.

Generally, $R^{2a}$ and/or $R^{2b}$, of the $N^2$-phosphinyl guanidine chromium compound complexes which have an $R^{2a}$ and/or $R^{2b}$ group, independently can be hydrogen or an organyl group; alternatively, hydrogen; or alternatively, an organyl group. In another aspect, $R^{2a}$ and/or $R^{2b}$, of the $N^2$-phosphinyl guanidine chromium compound complexes which have an $R^{2a}$ and/or $R^{2b}$ group, independently can be hydrogen or an organyl group consisting essentially of inert functional groups; alternatively, hydrogen; or alternatively, an organyl group consisting essentially of inert functional groups. In an aspect, $R^{2a}$ and/or $R^{2b}$, of the $N^2$-phosphinyl guanidine chromium compound complexes which have an $R^{2a}$ and/or $R^{2b}$ group, independently can be hydrogen or a hydrocarbyl group; alternatively, hydrogen; or alternatively, a hydrocarbyl group. In an embodiment, the $R^{2a}$ and $R^{2b}$ organyl groups of the $N^2$-phosphinyl guanidine chromium compound complexes which have an $R^{2a}$ and/or $R^{2b}$ organyl group, independently can be a $C_1$ to $C_{20}$, a $C_1$ to $C_{15}$, a $C_1$ to $C_{10}$, or a $C_1$ to $C_5$ organyl group. In some embodiments, the $R^{2a}$ and/or $R^{2b}$ organyl groups consisting of inert functional groups, of the $N^2$-phosphinyl guanidine chromium compound complexes which have an $R^{2a}$ and/or $R^{2b}$ organyl consisting of inert functional groups, independently can be a $C_1$ to $C_{20}$, a $C_1$ to $C_{15}$, a $C_1$ to $C_{10}$, or a $C_1$ to $C_5$ organyl group consisting essentially of inert functional groups. In other embodiments, the $R^{2a}$ and/or $R^{2b}$ hydrocarbyl groups, of the $N^2$-phosphinyl guanidine chromium compound complexes which have an $R^{2a}$ and/or $R^{2b}$ hydrocarbyl group, independently can be a $C_1$ to $C_{20}$, a $C_1$ to $C_{15}$, a $C_1$ to $C_{10}$, or a $C_1$ to $C_5$ hydrocarbyl group.

In an embodiment, $R^{2a}$ and $R^{2b}$, of the $N^2$-phosphinyl guanidine chromium compound complexes which have an $R^{2a}$ and/or $R^{2b}$, independently can be an alkyl group, a substituted alkyl group, a cycloalkyl group, a substituted cycloalkyl group, an aryl group, a substituted aryl group, an aralkyl group, or a substituted aralkyl group. In some embodiments, $R^{2a}$ and $R^{2b}$, of the $N^2$-phosphinyl guanidine chromium compound complexes which have an $R^{2a}$ and/or $R^{2b}$, independently can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^{2a}$ and $R^{2b}$, of the $N^2$-phosphinyl guanidine chromium compound complexes which have an $R^{2a}$ and/or $R^{2b}$, independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, $R^{2a}$ and/or $R^{2b}$ independently can be a $C_1$ to $C_{20}$, a $C_1$ to $C_{10}$, or a $C_1$ to $C_5$ alkyl group. In any aspect or embodiment disclosed herein, the alkyl group which can be utilized as $R^{2a}$ and/or $R^{2b}$ independently can be a $C_1$ to $C_{20}$, a $C_1$ to $C_{10}$, or a $C_1$ to $C_5$ substituted alkyl group. In any aspect or embodiment disclosed herein, the cycloalkyl group which can be utilized as $R^{2a}$ and/or $R^{2b}$ independently can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^{2a}$ and/or $R^{2b}$ independently can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^{2a}$ and/or $R^{2b}$ independently can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^{2a}$ and/or $R^{2b}$ independently can be a $C_6$ to $C_{20}$, a $C_6$ to $C_{15}$, or a $C_6$ to $C_{10}$ substituted aryl group. Each substituent of a substituted cycloalkyl group (general or specific) and/or a substituted aryl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^{2a}$ and/or $R^{2b}$.

In an aspect, $R^1$ and $R^2$ of the $N^2$-phosphinyl amidine chromium compound complexes can be joined to form a group, $L^1$, wherein $L^1$, the $N^1$ nitrogen atom, and the central carbon atom of the can form a ring or a ring system, as described in U.S. patent application Ser. No. 15/171,170 filed on Jun. 2, 2016. In such embodiments, the $N^2$-phosphinyl amidine chromium compound complexes can have Structure NPACr2. In an embodiment, $L^1$ of the $N^2$-phosphinyl amidine chromium compound complexes having Structure NPACr2 can be an organylene group; alternatively, an organylene group consisting of inert functional groups; or alternatively, a hydrocarbylene group. The organylene group which can be utilized as $L^1$ of the $N^2$-phosphinyl amidine chromium compound complexes having Structure NPACr2 can be a $C_3$ to $C_{30}$, $C_3$ to $C_{20}$, a $C_3$ to $C_{15}$, a $C_3$ to $C_{10}$, or a $C_3$ to $C_5$ organylene group. The organylene group consisting of inert functional groups which can be utilized as $L^1$ of the $N^2$-phosphinyl amidine chromium compound complexes having Structure NPACr2 can be a $C_3$ to $C_{30}$, $C_3$ to $C_{20}$, a $C_3$ to $C_{15}$, a $C_3$ to $C_{10}$, or a $C_3$ to $C_5$ organylene group consisting of inert functional groups. The hydrocarbylene group which can be utilized as $L^1$ of the $N^2$-phosphinyl amidine chromium compound complexes having Structure NPACr2 can be a $C_3$ to $C_{30}$, $C_3$ to $C_{20}$, a $C_3$ to $C_{15}$, a $C_3$ to $C_{10}$, or a $C_3$ to $C_5$ hydrocarbylene group.

In an embodiment, $L^1$ of the $N^2$-phosphinyl amidine chromium compound complexes having Structure NPACr2 can have any structure provided in Table 2. In some embodiments, $L^1$ can have Structure 1L, Structure 2L, Structure 3L, Structure 4L, Structure 5L, or Structure 6L. In some embodiments, $L^1$ can have Structure 2L or Structure 3L; or alternatively, Structure 5L or Structure 6L. In other embodiments, $L^1$ can have Structure 1L; alternatively, Structure 2L; alternatively, Structure 3L; alternatively, Structure 4L; alternatively, Structure 5L; or alternatively, Structure 6L.

TABLE 2

Structures for Linking Groups L1.

| | |
|---|---|
| $-(CR^{L60}R^{L61})_m-$ | Structure 1L |
| $-CR^{L62}R^{L63}-CR^{L66}R^{L67}-CR^{L64}R^{L65}-$ | Structure 2L |
| $-CR^{L62}R^{L63}-CR^{L66}R^{L67}-CR^{L68}R^{L69}-CR^{L64}R^{L65}-$ | Structure 3L |
| (aromatic ring structure with $R^{L73}$, $R^{L74}$, $R^{L75}$, $R^{L76}$, and $(CR^{L77}R^{L78})_n$) | Structure 4L |
| $-CR^{L80}R^{L81}-CR^{L82}=CR^{L83}-$ | Structure 5L |
| $-CR^{L84}=CR^{L85}-CR^{L86}=CR^{L87}-$ | Structure 6L |

Within the structures of Table 2, the undesignated valences represent the points at which the $L^1$ linking group attach to the respective nitrogen and central carbon atom of the amidine group of the $N^2$-phosphinyl amidine chromium compound complex. Generally, m of the $L^1$ linking group having Structure 1L can be an integer ranging from 2 to 5; alternatively, m can be 3 or 4; alternatively, m can be 3; or alternatively, m can be 4. Generally, n of the $L^1$ linking group having Structure 4L can be an integer ranging from 1 to 3; alternatively, n can be 1 or 2; alternatively, n can be 1; or alternatively, n can be 2. In any aspect or embodiment described herein, $R^{L60}$ and $R^{L61}$ of the $L^1$ linking group having Structure 1L, $R^{L62}$, $R^{L63}$, $R^{L64}$, $R^{L65}$, $R^{L66}$, and $R^{L67}$ of the $L^1$ linking group having Structure 2L, $R^{L62}$, $R^{L63}$, $R^{L64}$, $R^{L65}$, $R^{L66}$, $R^{L67}$, $R^{L68}$, and $R^{L69}$, of the $L^1$ linking group having Structure 3L, $R^{L73}$, $R^{L74}$, $R^{L75}$, $R^{L76}$, $R^{L77}$, and $R^{L78}$ of the $L^1$ linking group having Structure 4L, $R^{L80}$, $R^{L81}$, $R^{L82}$, and $R^{L83}$ of the $L^1$ linking group having Structure 5L, $R^{L84}$, $R^{L85}$, $R^{L86}$, and $R^{L87}$ of the $L^1$ linking group having Structure 6L independently can be a hydrogen or a non-hydrogen substituent group; or alternatively, hydrogen. Non-hydrogen substituent groups (general and specific) are independently disclosed herein and can be utilized without limitation to further describe the $L^1$ linking group having Structure 1L, Structure 2L, Structure 3L, Structure 4L, and/or Structure 5L. In an embodiment, $L^1$ can be a prop-1,3-ylene group ($-CH_2CH_2CH_2-$), a but-1,3-ylene group ($-CH_2CH_2CH(CH_3)-$), a but-1,4-ylene group ($-CH_2CH_2CH_2CH_2-$), a pent-1,4-ylene group ($-CH_2CH_2CH_2CH(CH_3)-$), a 2-methylenephen-1-ylene group, or a 2-(ethylene)phen-1-ylene group. In some non-limiting embodiments, $L^1$ can be a prop-1,3-ylene group ($-CH_2CH_2CH_2-$), a but-1,3-ylene group ($-CH_2CH_2CH(CH_3)-$), a but-1,4-ylene group ($-CH_2CH_2CH_2CH_2-$), or a pent-1,4-ylene group ($-CH_2CH_2CH_2CH(CH_3)-$); alternatively, a prop-1,3-ylene group ($-CH_2CH_2CH_2-$) or a but-1,4-ylene group ($-CH_2CH_2CH_2CH_2-$); alternatively, a but-1,3-ylene group ($-CH_2CH_2CH(CH_3)-$) or a pent-1,4-ylene group ($-CH_2CH_2CH_2CH(CH_3)-$); or alternatively, a 2-methylenephen-1-ylene group or a 2-(ethylene)phen-1-ylene group. In other non-limiting embodiments, $L^1$ can be a prop-1,3-ylene group ($-CH_2CH_2CH_2-$); alternatively, a but-1,3-ylene group ($-CH_2CH_2CH(CH_3)-$);

alternatively, a but-1,4-ylene group (—CH$_2$CH$_2$CH$_2$CH$_2$—); alternatively, a pent-1,4-ylene group (—CH$_2$CH$_2$CH$_2$CH(CH$_3$)—); alternatively, a 2-methylenephen-1-ylene group; or alternatively, a 2-(ethylene)phen-1-ylene group.

In an aspect, R$^1$ and R$^{2a}$ of the N$^2$-phosphinyl guanidine chromium compound complexes can be joined to form a group, L$^{12}$, wherein L$^{12}$, the N$^1$ nitrogen atom, and the N$^3$ nitrogen atom can form a ring or a ring system. In another aspect, R$^3$ and R$^{2b}$ of the N$^2$-phosphinyl guanidine chromium compound complexes can be joined to form a group, L$^{23}$, wherein L$^{23}$, the N$^2$ nitrogen atom, and the N$^3$ nitrogen atom can form a ring or a ring system. In an embodiment, L$^{12}$ and/or L$^{23}$, of the N$^2$-phosphinyl guanidine chromium compound complexes which have an L$^{12}$ group and/or an L$^{23}$ group, independently can be an organylene group; alternatively, an organylene group consisting of inert functional groups; or alternatively, a hydrocarbylene group. The organylene group which can be utilized as L$^{12}$ and/or L$^{23}$ of the N$^2$-phosphinyl guanidine chromium compound complexes which have an L$^{12}$ group and/or an L$^{23}$ group independently can be a C$_2$ to C$_{20}$, a C$_2$ to C$_{15}$, a C$_2$ to C$_{10}$, or a C$_2$ to C$_5$ organylene group. The organylene group consisting of inert functional groups which can be utilized as L$^{12}$ and/or L$^{23}$ of the N$^2$-phosphinyl guanidine chromium compound complexes which have an L$^{12}$ group and/or an L$^{23}$ group independently can be a C$_2$ to C$_{20}$, a C$_2$ to C$_{15}$, a C$_2$ to C$_{10}$, or a C$_2$ to C$_5$ organylene group consisting of inert functional groups. The hydrocarbylene group which can be utilized as L$^{12}$ and/or L$^{23}$ of the N$^2$-phosphinyl guanidine chromium compound complexes which have an L$^{12}$ group and/or an L$^{23}$ group independently can be a C$_2$ to C$_{20}$, a C$_2$ to C$_{15}$, a C$_2$ to C$_{10}$, or a C$_2$ to C$_5$ hydrocarbylene group.

In an embodiment, L$^{12}$ and/or L$^{23}$ can have any structure provided in Table 3. In some embodiments, L$^{12}$ and/or L$^{23}$ can have Structure 21L, Structure 22L, Structure 23L, Structure 24L or Structure 25L. In some embodiments, L$^{12}$ and/or L$^{23}$ can have Structure 22L or Structure 23L; alternatively, Structure 24L or Structure 25L. In other embodiments, L$^{12}$ and/or L$^{23}$ can have Structure 21L; alternatively, Structure 22L; alternatively, Structure 23L; alternatively, Structure 24L; or alternatively, Structure 25L. In some embodiments, L$^{12}$ and/or L$^{23}$ can have Structure 26L. It should be noted that when L$^{12}$ has Structure 26L the corresponding R$^{2b}$ is null because of the double bond link (depicted as real but can be delocalized through aromatic resonance) with the N$^3$ nitrogen atom of the N$^2$-phosphinyl guanidine metal complex.

TABLE 3

Structures for Linking Groups L$^{12}$ and/or L$^{23}$.

| | |
|---|---|
| —(CR$^{L1}$R$^{L2}$)$_m$— | Structure 21L |
| —CR$^{L3}$R$^{L4}$—CR$^{L5}$—R$^{L6}$— | Structure 22L |
| —CR$^{L3}$R$^{L4}$—CR$^{L7}$R$^{L8}$—CR$^{L5}$R$^{L6}$— | Structure 23L |
| —CR$^{11L}$=CR$^{12L}$— | Structure 24L |
| 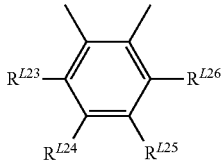 | Structure 25L |
| =CR$^{27}$—CR$^{28}$=CR$^{29}$— | Structure 26L |

Within the structures of Table 3, the undesignated valences represent the points at which L$^{12}$ and/or L$^{23}$, when present, attach to the respective nitrogen atoms of the N$^2$-phosphinyl guanidine chromium compound complex. Generally, m can be an integer ranging from 2 to 5. In further embodiments, m can be 2 or 3; alternatively, m can be 2; or alternatively, m can be 3. R$^{L1}$ and R$^{L2}$ of the linking group having Structure 21L, R$^{L3}$, R$^{L4}$, R$^{L5}$, and R$^{L6}$ of the linking group having Structure 22L, R$^{L3}$, R$^{L4}$, R$^{L5}$, R$^{L6}$, R$^{L7}$, and R$^{L8}$, of the linking group having Structure 23L, R$^{L11}$ and R$^{L12}$ of the linking group having Structure 24L, R$^{L23}$, R$^{L24}$, R$^{L25}$, and R$^{L26}$ of the linking group having Structure 25L, R$^{L27}$, R$^{L28}$, and R$^{L29}$ of the linking group having Structure 26L independently can be a hydrogen or a non-hydrogen substituent group; or alternatively, hydrogen. Non-hydrogen substituent groups (general and specific) are independently disclosed herein and can be utilized without limitation to further describe the linking group having Structure 21L, Structure 22L, Structure 23L, Structure 24L, and/or Structure 25L. In an embodiment, L$^{12}$ and/or L$^{23}$ can be an eth-1,2-ylene group (—CH$_2$CH$_2$—), an ethen-1,2-ylene group (—CH=CH—), a prop-1,3-ylene group (—CH$_2$CH$_2$CH$_2$—), a 1-methylethen-1,2-ylene group (—C(CH$_3$)=CH—), a but-1,3-ylene group (—CH$_2$CH$_2$CH(CH$_3$)—), a 3-methylbut-1,3-ylene group (—CH$_2$CH$_2$C(CH$_3$)$_2$—), or a phen-1,2-ylene group. In some non-limiting embodiments, L$^{12}$ and/or L$^{23}$ be an eth-1,2-ylene group (—CH$_2$CH$_2$—), a prop-1,3-ylene group (—CH$_2$CH$_2$CH$_2$—), a 1-methylethen-1,2-ylene group (—C(CH$_3$)=CH—), a but-1,3-ylene group (—CH$_2$CH$_2$CH(CH$_3$)—), or a 3-methylbut-1,3-ylene group (—CH$_2$CH$_2$C(CH$_3$)$_2$—); alternatively, an eth-1,2-ylene group (—CH$_2$CH$_2$—), an ethen-1,2-ylene group (—CH=CH—), a prop-1,3-ylene group (—CH$_2$CH$_2$CH$_2$—), or a phen-1,2-ylene group; alternatively, an eth-1,2-ylene group (—CH$_2$CH$_2$—) or a prop-1,3-ylene group (—CH$_2$CH$_2$CH$_2$—); alternatively, an ethen-1,2-ylene group (—CH=CH—) or a phen-1,2-ylene group. In other embodiments, L$^{12}$ and/or L$^{23}$ can be an eth-1,2-ylene group (—CH$_2$CH$_2$—); alternatively, an ethen-1,2-ylene group (—CH=CH—); alternatively, a prop-1,3-ylene group (—CH$_2$CH$_2$CH$_2$—); alternatively, a 1-methylethen-1,2-ylene group (—C(CH$_3$)=CH—); alternatively, a but-,3-lene group (—CH$_2$CH$_2$CH(CH$_3$)—); alternatively, a 3-methylbut-1,3-ylene group (—CH$_2$CH$_2$C(CH$_3$)$_2$—); or alternatively, a phen-1,2-ylene group. In some embodiments, L$^{12}$ and/or L$^{23}$ can be a —CH=CH—CH=group.

In an embodiment, L$^{12}$ can have a structure that can comprise at least one substituent located on the carbon atom attached to the N$^1$ nitrogen atom of the N$^2$-phosphinyl guanidine chromium compound complex; alternatively, can comprise only one substituent located on the carbon atom attached to the N$^1$ nitrogen atom of the N$^2$-phosphinyl guanidine chromium compound complex; or alternatively, can comprise two substituents located on the carbon atom attached to the N$^1$ nitrogen atom of the N$^2$-phosphinyl guanidine chromium compound complex. In another embodiment, L$^{12}$ can have a structure that can consist of one substituent located on the carbon atom attached to the N$^1$ nitrogen atom of the N$^2$-phosphinyl guanidine chromium compound complex; or alternatively, can consist of two substituents located on the carbon atom attached to the N$^1$ nitrogen atom of the N$^2$-phosphinyl guanidine chromium compound complex.

In an embodiment, R$^{2a}$ and R$^{2b}$ of the N$^2$-phosphinyl guanidine chromium compound complexes can be joined to form a group, L$^{22}$, wherein R$^{2a}$, R$^{2b}$, and the N$^3$ nitrogen (or $L^{22}$ and the $N^3$ nitrogen) form a ring or ring system. In an embodiment, $L^{22}$ of the $N^2$-phosphinyl guanidine chromium compound complexes having an $L^{22}$ group can be an organylene group; alternatively, an organylene group consisting of inert functional groups; or alternatively, a hydrocarbylene group. The organylene group which can be utilized as $L^{22}$ of the $N^2$-phosphinyl guanidine chromium compound complexes having an $L^{22}$ group can be a $C_3$ to $C_{20}$, a $C_3$ to $C_{15}$, or a $C_3$ to $C_{10}$ organylene group. The organylene group consisting of inert functional groups which can be utilized as $L^{22}$ of the $N^2$-phosphinyl guanidine chromium compound complexes having an $L^{22}$ group can be a $C_3$ to $C_{20}$, a $C_3$ to $C_{15}$, or a $C_3$ to $C_{10}$ organylene group consisting of inert functional groups. The hydrocarbylene group which can be utilized as $L^{22}$ of the $N^2$-phosphinyl guanidine chromium compound complexes having an $L^{22}$ group can be a $C_4$ to $C_{20}$, a $C_4$ to $C_{15}$, or a $C_4$ to $C_{10}$ hydrocarbylene group.

In an embodiment, $L^{22}$ can have any structure provided in Table 4. In some embodiments, $L^{22}$ can have Structure 11L, Structure 12L, Structure 13L, Structure 14L, Structure 15L; or Structure 16L. In other embodiments, $L^{22}$ can have Structure 11L; alternatively, Structure 12L; alternatively, Structure 13L; alternatively, Structure 14L; or alternatively, Structure 15L.

TABLE 4

Structures for Linking Groups $L^{22}$.

| | |
|---|---|
| —$(CR^{L31}R^{L32})_n$— | —$CR^{L41}R^{L42}$—$CR^{L45}R^{L46}$ $CR^{L47}R^{L48}$ $CR^{L43}R^{L44}$— |
| Structure 11L | Structure 12L |
| —$CR^{L41}R^{L42}$—$CR^{L45}R^{L46}$—$CR^{L49}R^{L50}$—$CR^{L47}R^{L48}$—$CR^{L43}R^{L44}$— | |
| Structure 13L | |
| —$CR^{L41}R^{L42}$—$CR^{L45}R^{L46}$—O—$CR^{L47}R^{L48}$—$CR^{L43}R^{L44}$— | —$CR^{L51}$=$CR^{L53}$—$CR^{L54}$=$CR^{L52}$— |
| Structure 14L | Structure 15L |

Within the structures of Table 4, the undesignated valences represent the points at which $L^{22}$ of the $N^2$-phosphinyl guanidine chromium compound complexes, when present, attach to the $N^3$ nitrogen atom of the $N^2$-phosphinyl guanidine chromium compound complex. Generally, n can be an integer ranging from 4 to 7. In further embodiments, n can be 4 or 5; alternatively, n can be 4; or alternatively, n can be 5. $R^{L31}$ and $R^{L32}$ of the linking group having Structure 11L, $R^{L41}$, $R^{L42}$, $R^{L43}$, $R^{L44}$, $R^{L45}$, $R^{L46}$, $R^{L47}$, and $R^{L48}$ of the linking group having Structure 12L, $R^{L41}$, $R^{L42}$, $R^{L43}$, $R^{L44}$, $R^{L45}$, $R^{L46}$, $R^{L47}$, $R^{L48}$, $R^{L49}$, and $R^{L50}$ of the linking group having Structure 13L, $R^{L41}$, $R^{L42}$, $R^{L43}$, $R^{L44}$, $R^{L45}$, $R^{L46}$, $R^{L47}$, and $R^{L48}$ of the linking group having Structure 14L, and $R^{L41}$, $R^{L42}$, $R^{L43}$, $R^{L44}$, $R^{L45}$, $R^{L46}$, $R^{L47}$, and $R^{L48}$ of the linking group having Structure 15L independently can be a hydrogen or a non-hydrogen substituent group; alternatively, hydrogen. Non-hydrogen substituent groups are independently disclosed herein and can be utilized without limitation to further describe the linking group having Structure 11L, Structure 12L, Structure 13L, Structure 14L, and/or Structure 15L. In an embodiment, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; alternatively, a but-1,4-ylene group, a pent-1,5-ylene group, or a bis(eth-2-yl)ether group; alternatively, a but-1,4-ylene group; alternatively, a pent-1,5-ylene group; alternatively, a buta-1,3-dien-1,4-ylene group; or alternatively, a bis(eth-2-yl)ether group.

Generally, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be hydrogen or an organyl group; hydrogen or an organyl group consisting essentially of inert functional group; alternatively, hydrogen or a hydrocarbyl group; alternatively, hydrogen; alternatively, an organyl group; alternatively, an organyl group consisting essentially of inert functional group; or alternatively, a hydrocarbyl group. In an embodiment, the organyl group which can be utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a $C_1$ to $C_{20}$, a $C_1$ to $C_{15}$, a $C_1$ to $C_{10}$, or a $C_1$ to $C_5$ organyl group. In an embodiment, the organyl group consisting essentially of inert functional groups which can utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the hydrocarbyl group which can be utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a, a $C_1$ to $C_{20}$, a $C_1$ to $C_{15}$, a $C_1$ to $C_{10}$, or a $C_1$ to $C_5$ hydrocarbyl group. In other embodiments, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a $C_1$ to $C_{30}$, a $C_1$ to $C_{20}$, a $C_1$ to $C_{15}$, a $C_1$ to $C_{10}$, or a $C_1$ to $C_5$ alkyl group. In yet other embodiments, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. Substituent groups (general and specific) are provided herein and these substituent groups can be utilized to further describe the substituted phenyl groups which can be utilized as $R^3$ of any of the $N^2$-phosphinyl formamidine chromium compound complexes, the $N^2$-phosphinyl amidine chromium compound complexes, and/or the $N^2$-phosphinyl guanidine chromium compound complexes having a non-hydrogen $R^3$ group.

Generally, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an organyl group; alternatively, an organyl group consisting essentially of inert functional groups; or alternatively, a hydrocarbyl group. In an embodiment, the $R^4$ and/or $R^5$ organyl groups of the $N^2$-phosphinyl formamidine chromium compound complexes, the $N^2$-phosphinyl amidine chromium compound complexes, and/or the $N^2$-phosphinyl guanidine chromium compound complexes independently can be a $C_1$ to $C_{20}$, a $C_1$ to $C_{15}$, a $C_1$ to $C_{10}$, or a $C_1$ to $C_5$ organyl group. In an embodiment, the $R^4$ and/or $R^5$ organyl groups consisting essentially of inert functional groups of the $N^2$-phosphinyl formamidine chromium compound complexes, the $N^2$-phosphinyl amidine chromium compound complexes, and/or the $N^2$-phosphinyl guanidine chromium compound complexes independently can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the $R^4$ and/or $R^5$ hydrocarbyl groups of the $N^2$-phosphinyl formamidine chromium compound complexes, the $N^2$-phosphinyl amidine chromium compound complexes, and/or the $N^2$-phosphinyl guanidine chromium compound complexes independently can be a $C_1$ to $C_{20}$, a $C_1$ to $C_{15}$, a $C_1$ to $C_{10}$, or a $C_1$ to $C_5$ hydrocarbyl group. In further embodiments, $R^4$ and $R^5$ of the $N^2$-phosphinyl formamidine chromium compound complexes, the $N^2$-phosphinyl amidine chromium compound complexes, and/or the $N^2$-phosphinyl guanidine chromium compound complexes can be joined to form a ring or a ring system (regardless of particular type of group organyl, organyl consisting of inert functional groups, or hydrocarbyl group, including any species, sub-species, or individuals contained therein and/or described herein) containing the phosphorus atom of the $N^2$-phosphinyl formamidine chromium compound complexes, the $N^2$-phosphinyl amidine chromium compound complexes, and/or the $N^2$-phosphinyl guanidine chromium compound complexes disclosed herein.

In an embodiment, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group, a substituted alkyl group, a cycloalkyl group, a substituted cycloalkyl group, an aryl group, a substituted aryl group, an aralkyl group, or a substituted aralkyl group. In some embodiments, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, each alkyl group which can be utilized as $R^4$ and/or $R^5$ independently can be a $C_1$ to $C_{20}$, a $C_1$ to $C_{10}$, or a $C_1$ to $C_5$ alkyl group. In any aspect or embodiment disclosed herein, each substituted alkyl group which can be utilized as $R^4$ and/or $R^5$ independently can be a $C_1$ to $C_{20}$, a $C_1$ to $C_{10}$, or $C_1$ to $C_5$ substituted alkyl group. In any aspect or embodiment disclosed herein, each cycloalkyl group which can be utilized as $R^4$ and/or $R^5$ independently can be a $C_4$ to $C_{20}$, a $C_4$ to $C_{15}$, or a $C_4$ to $C_{10}$ cycloalkyl group. In any aspect or embodiment disclosed herein, each substituted cycloalkyl group which can be utilized as $R^4$ and/or $R^5$ independently can be a $C_4$ to $C_{20}$, a $C_4$ to $C_{15}$, or a $C_4$ to $C_{10}$ substituted cycloalkyl group. In any aspect or embodiment disclosed herein, each aryl group which can be utilized as $R^4$ and/or $R^5$ independently can be a $C_6$ to $C_{20}$, a $C_6$ to $C_{15}$, or a $C_6$ to $C_{10}$ aryl group. In any aspect or embodiment disclosed herein, each substituted aryl group which can be utilized as $R^4$ and/or $R^5$ independently can be a $C_6$ to $C_{20}$, a $C_6$ to $C_{15}$, or a $C_6$ to $C_{10}$ substituted aryl group. In any aspect or embodiment disclosed herein, each aralkyl group which can be utilized $R^4$ and/or $R^5$ independently can be a $C_7$ to $C_{20}$, a $C_7$ to $C_{15}$, or a $C_7$ to $C_{10}$ aralkyl group. In any aspect or embodiment disclosed herein, each substituted aryl group which can be utilized as $R^4$ and/or $R^5$ independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^4$ and/or $R^5$.

In an embodiment, $R^4$ and $R^5$ independently can be a methyl group, an ethyl group, a propyl group, a butyl group, a pentyl group, a hexyl group, a heptyl group, or an octyl group. In some embodiments, $R^4$ and $R^5$ independently can be a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Substituent halogens and substituent hydrocarboxy (general and specific) groups are independently disclosed herein. These substituent halogens and substituent hydrocarboxy groups can be utilized without limitation to further describe a substituted alkyl group which can be utilized as $R^4$ and/or $R^5$ independently.

In an embodiment, $R^4$ and $R^5$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized for $R^4$ and/or $R^5$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; alternatively, a 2,6-disubstituted cyclohexyl group or a 2,5-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,5-disubstituted cyclopentyl group. In an embodiment where the substituted cycloalkyl group (general or specific) has more the one substituent, the substituents can be the same or different; alternatively, the same; or alternatively, different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^4$ and/or $R^5$.

In a non-limiting embodiment, $R^4$ and $R^5$ independently can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, or 2,5-dialkylcyclopentyl group. Alkyl substituent groups (general and specific) are independently described herein and these alkyl substituent groups can be utilized, without limitation, to further described alkylcyclohexyl groups (general or specific), dialkylcyclohexyl groups (general or specific), alkylcyclopentyl groups (general or specific), and/or dialkylcyclopentyl groups (general or specific) which can be utilized as $R^4$ and/or $R^5$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting embodiments, $R^4$ and $R^5$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, $R^4$ and $R^5$ independently can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^4$ and $R^5$ independently can be a phenyl group, a substituted phenyl group; alternatively, a phenyl group; or alternatively, a substituted phenyl group. In an embodiment, the substituted phenyl group, which can be utilized for $R^4$ and/or $R^5$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^4$ and/or $R^5$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^4$ and/or $R^5$.

In a non-limiting embodiment, $R^4$ and $R^5$ independently can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^4$ and/or $R^5$. Generally, the alkyl substituents of a dialkylphenyl group (general or specific) or a trialkylphenyl group (general or specific) can be the same; or alternatively, the alkyl substituents of a dialkylphenyl group (general or specific) or a trialkyl phenyl group (general or specific) can be different. In some non-limiting embodiments, $R^4$ and $R^5$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, $R^4$ and $R^5$ can be a phenyl group, a 2-alkoxyphenyl group, or a 4-alkoxyphenyl group. In some non-limiting embodiments, $R^4$ and/or $R^5$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiment, $R^4$ and $R^5$ independently can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some embodiments, $R^4$ and $R^5$ independently can be a phenyl group, a 2-fluorophenyl group, 4-fluorophenyl group, or a 2,6-difluorophenyl group.

In an embodiment, $R^4$ and $R^5$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^4$ and/or $R^5$.

Generally, the chromium compound of the $N^2$-phosphinyl formamidine chromium compound complexes, the $N^2$-phosphinyl amidine chromium compound complexes, and/or the $N^2$-phosphinyl guanidine chromium compound complexes described herein can have the formula $CrX_p$ where X represents a monoanionic ligand, and p represents the number of monoanionic ligands (and the oxidation state of the chromium in the chromium compound). The monoanionic ligand (X) and p are independent elements of the chromium compound and are independently described herein. The independent descriptions of the monoanionic ligand (X) and p can be utilized without limitation, and in any combination, to further describe the chromium compound of the $N^2$-phosphinyl formamidine chromium compound complexes, the $N^2$-phosphinyl amidine chromium compound complexes, and/or the $N^2$-phosphinyl guanidine chromium compound complexes.

Generally, the chromium atom of the chromium compound ($CrX_p$) can have any positive oxidation state available to a chromium atom. In an embodiment, the chromium atom can have an oxidation state of from +2 to +6; alternatively, from +2 to +4; or alternatively, from +2 to +3. In some embodiments, the chromium atom of the chromium compound ($CrX_p$) can have an oxidation state of +2; alternatively, +3; or alternatively, +4.

The monoanion, X, of the chromium compound can be any monoanion. In an embodiment, the monoanion, X, can be a halide, a carboxylate, a β-diketonate, a hydrocarboxide, a nitrate, or a chlorate. In some embodiments, the monoanion, X, can be a halide, a carboxylate, a β-diketonate, or a hydrocarboxide. In any aspect or embodiment, the hydrocarboxide can be an alkoxide, an aryloxide, or an aralkoxide. Generally, hydrocarboxide (and subdivisions of hydrocarboxide) are the anion analogues of the hydrocarboxy group. In other embodiments, the monoanion, X, can be a halide, a carboxylate, a β-diketonate, or an alkoxide; or alternatively, a halide or a β-diketonate. In other embodiments, the monoanion, X, can be a halide; alternatively, a carboxylate; alternatively, a β-diketonate; alternatively, a hydrocarboxide; alternatively, an alkoxide; or alternatively, an aryloxide. Generally, the number, p, of monoanions can equal the oxidation state of the metal atom. In an embodiment, the number, p, of monoanions, X, can be an integer from 2 to 6; alternatively, an integer from 2 to 4; alternatively, an integer from 2 to 3; alternatively, 2; alternatively, 3; or alternatively, 4.

Generally, each halide monoanion, X, of the chromium compound independently can be fluorine, chlorine, bromine, or iodine; or alternatively, chlorine, bromine, or iodine. In an embodiment, each halide monoanion, X, of the chromium compound can be chlorine; alternatively, bromine; or alternatively, iodine.

Generally, each carboxylate monoanion of the chromium compound independently can be a $C_1$ to $C_{20}$ carboxylate; or alternatively, a $C_1$ to $C_{10}$ carboxylate. In an embodiment, each carboxylate monoanion of the chromium compound independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some embodiments, each carboxylate monoanion of the chromium compound independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some embodiments, the carboxylate monoanion of the chromium compound can be triflate (trifluoroacetate).

Generally, each β-diketonate monoanion of the chromium compound independently can be any $C_1$ to $C_{20}$ a β-diketonate; or alternatively, any $C_1$ to $C_{10}$ β-diketonate. In an embodiment, each β-diketonate monoanion of the chromium compound independently can be acetylacetonate (i.e., 2,4-pentanedionate), hexafluoroacetylacetone (i.e., 1,1,1,5,5,5-hexafluoro-2,4-pentanedionate), or benzoylacetonate; alternatively, acetylacetonate; alternatively, hexafluoroacetylacetone; or alternatively, benzoylacetonate.

Generally, each hydrocarboxide monoanion of the chromium compound independently can be any $C_1$ to $C_{20}$ hydrocarboxide; or alternatively, any $C_1$ to $C_{10}$ hydrocarboxide. In an embodiment, each hydrocarboxide monoanion of the chromium compound independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an embodiment, each alkoxide monoanion of the chromium compound independently can be methoxide, ethoxide, a propoxide, or a butoxide. In some embodiments, each alkoxide monoanion of the chromium compound independently can be methoxide, ethoxide, isopropoxide, or tert-butoxide; alternatively, methoxide; alternatively, an ethoxide; alternatively, an iso-propoxide; or alternatively, a tert-butoxide. In an aspect, the aryloxide can be phenoxide.

In a non-limiting embodiment, the chromium compound of any of the $N^2$-phosphinyl formamidine chromium compound complexes, $N^2$-phosphinyl amidine chromium compound complexes, and/or the $N^2$-phosphinyl guanidine chromium compound complexes described herein can comprise, can consist essentially of, or consist of, a chromium(II) halide, a chromium(III) halide, a chromium(II) carboxylate, chromium(III) carboxylate, a chromium(II) β-diketonate, or a chromium(III) β-diketonate. In some non-limiting embodiments, the chromium compound of any of the $N^2$-phosphinyl formamidine chromium compound complexes, $N^2$-phosphinyl amidine chromium compound complexes, and/or the $N^2$-phosphinyl guanidine chromium compound complexes described herein can comprise, can consist essentially of, or consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting embodiments, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, a chromium(II) halide; alternatively, a chromium(III) halide; alternatively, a chromium (II) carboxylate; alternatively, a chromium(III) carboxylate; alternatively, a chromium(II) β-diketonate; or alternatively, a chromium(III) β-diketonate.

In a non-limiting embodiment, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, chromium(II) chloride, chromium(III) chloride, chromium(II) fluoride, chromium(III) fluoride, chromium(II) bromide, chromium(III) bromide, chromium(II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium(II) acetylacetonate, chromium(III) acetylacetonate, chromium(II) hexafluoracetylacetonate, chromium(III) hexafluoracetylacetonate, chromium (III) benzoylacetonate, or chromium(III) benzoylacetonate. In some non-limiting embodiments, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, chromium(III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium (III) acetylacetonate, chromium(III) hexafluoracetylacetonate, or chromium(III) benzoylacetonate. In further embodiments, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can be chromium(III) chloride or chromium(III) acetylacetonate; alternatively, chromium(III) chloride; or alternatively, chromium(III) acetylacetonate.

Generally, the neutral ligand, Q, of any of the $N^2$-phosphinyl formamidine chromium compound complexes, the $N^2$-phosphinyl amidine chromium compound complexes, and/or the $N^2$-phosphinyl guanidine chromium compound complexes described herein, if present, independently can be any neutral ligand that forms an isolatable compound with the $N^2$-phosphinyl formamidine chromium compound complex, the $N^2$-phosphinyl amidine chromium compound complex, and/or the $N^2$-phosphinyl guanidine chromium compound complex. In an aspect, each neutral ligand independently can be a nitrile or an ether; alternatively, a nitrile; or alternatively, an ether. The number of neutral ligands, q, can be any number that forms an isolatable compound with the $N^2$-phosphinyl formamidine chromium compound complexes, the $N^2$-phosphinyl amidine chromium compound complexes, and/or the $N^2$-phosphinyl guanidine chromium compound complexes. In an aspect, the number of neutral ligands of any of the $N^2$-phosphinyl formamidine chromium compound complexes, the $N^2$-phosphinyl amidine chromium compound complexes, and/or the $N^2$-phosphinyl guanidine chromium compound complexes described herein can range from 0 to 6; alternatively, range from 0 to 3; alternatively, can be 0; alternatively, can be 1; alternatively, can be 2; alternatively, can be 3; or alternatively, can be 4.

Generally, each nitrile ligand independently can be a $C_2$ to $C_{20}$ nitrile; or alternatively, a $C_2$ to $C_{10}$ nitrile. In an embodiment, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some embodiments, each nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an embodiment, each aliphatic nitrile independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each ether ligand independently can be a $C_2$ to $C_{40}$ ether; alternatively, a $C_2$ to $C_{30}$ ether; or alternatively, a $C_2$ to $C_{20}$ ether. In an embodiment, each ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some embodiments, each ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other embodiments, each ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some embodiments, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

In a non-limiting embodiment, the $N^2$-phosphinyl formamidine chromium compound complex can be any one or more of NPFCr I, NPFCr II, NPFCr III, NPFCr IV, NPFCr V, and NPFCr VI. In a non-limiting embodiment, the $N^2$-phosphinyl amidine chromium compound complex can be any one or more of NPACr I, NPACr II, NPACr III, NPACr IV, NPACr V, NPACr VI, NPACr VII, NPACr VIII, NPACr IX, NPACr X, NPACr XI, NPACr XII, NPACr XIII, NPACr XIV, NPACr XV, NPACr XVI, NPACr XVII, NPACr XVIII, and NPACr XIX. In a non-limiting embodiment, the $N^2$-phosphinyl guanidine chromium compound complex can be any one or more of GuCr I, GuCr II, GuCr III, GuCr IV, GuCr V, GuCr VI, and GuCr VII. In non-limiting embodiments, the chromium compound, $CrX_3$, of any of NPFCr I, NPFCr II, NPFCr III, NPFCr IV, NPFCr V, NPFCr VI, NPACr I, NPACr II, NPACr III, NPACr IV, NPACr V, NPACr VI, NPACr VII, NPACr VIII, NPACr IX, NPACr X, NPACr XI, NPACr XII, NPACr XIII, NPACr XIV, NPACr XV, NPACr XVI, NPACr XVII, NPACr XVIII, NPACr XIX, GuCr I, GuCr II, GuCr III, GuCr IV, GuCr V, GuCr VI, and GuCr VII can be chromium(III) chloride or chromium(III) acetylacetonate; alternatively, chromium(III) chloride; or alternatively, chromium(III) acetylacetonate.

NPFCr I

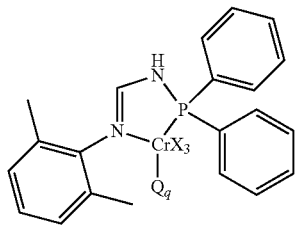

NPFCr II

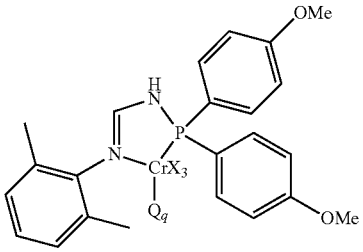

NPFCr III

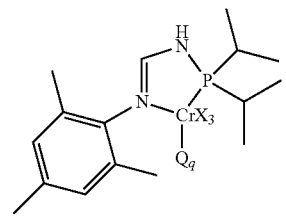

NPFCr IV

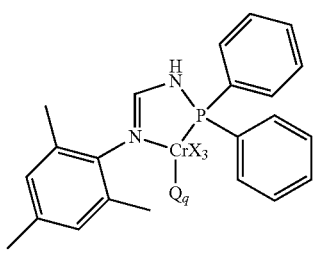

NPFCr V

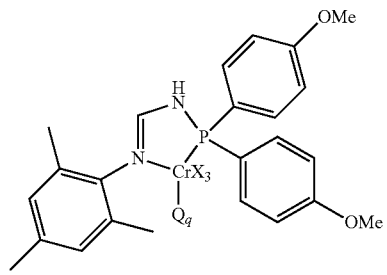

NPFCr VI

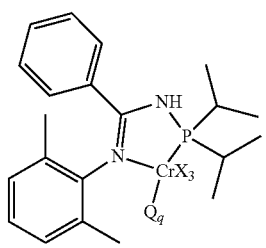

NPACr I

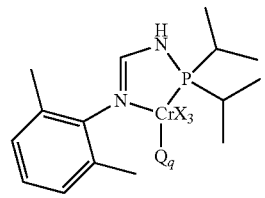

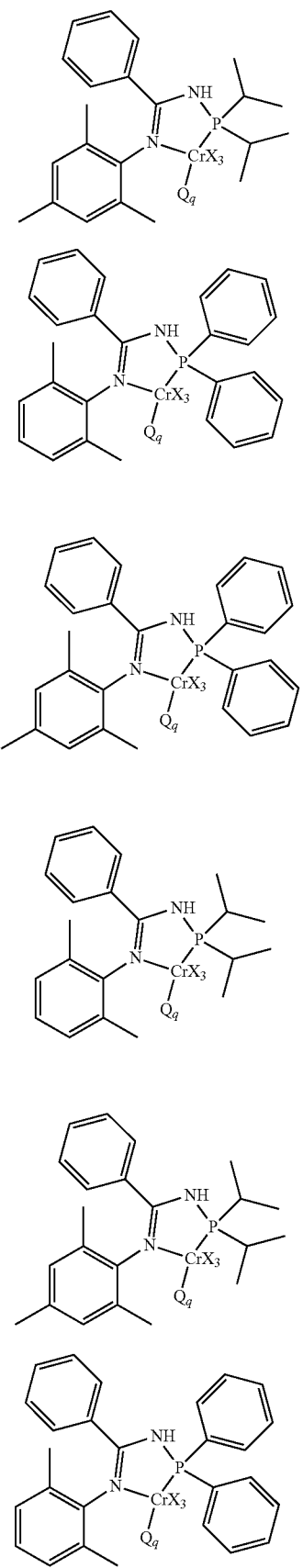
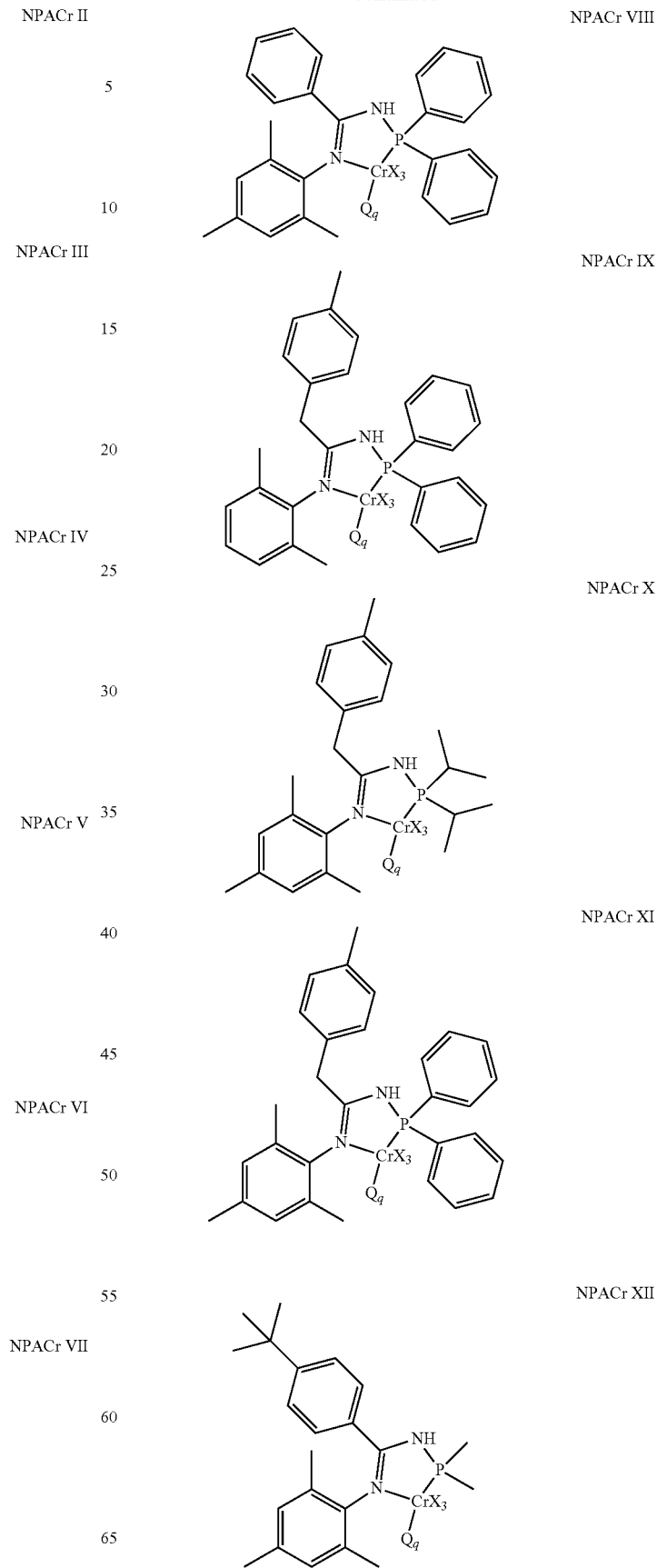

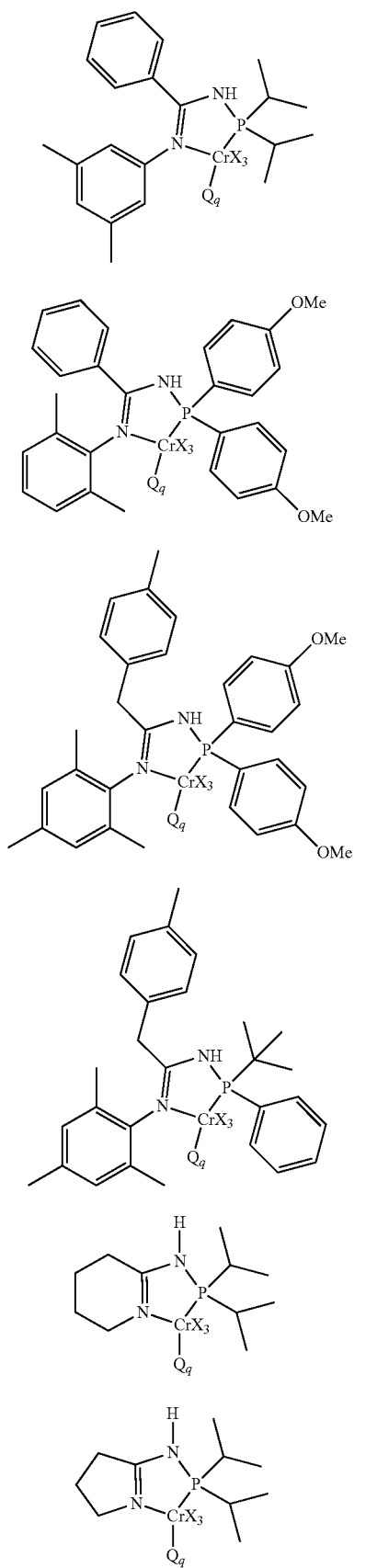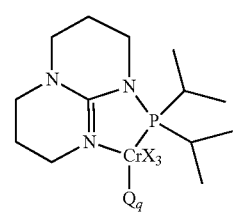

NPACr XIX

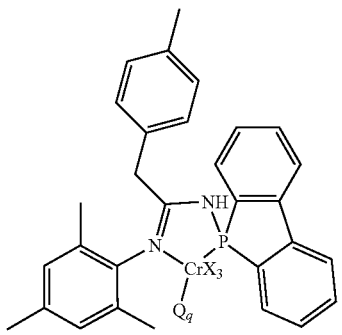

Any process described herein can further comprise preparing the catalyst system. In an embodiment, the catalyst system can be prepared by 1) contacting the chromium component (any described herein) and the aluminoxane compound (any described herein) to form a catalyst system mixture, and 2) aging the catalyst system mixture in the substantial absence of ethylene to form an aged catalyst system mixture. In an embodiment, the catalyst system mixture can be aged for a period of time. Typically, the minimum catalyst system mixture aging time can be 5 seconds, 10 seconds, 30 seconds, 1 minute, 5 minutes, 10 minutes, or 20 minutes; additionally or alternatively, the maximum aging time can be 48 hours, 36 hours, 24 hours, 18 hours, 12 hours, 6 hours, 4 hours, or 2 hours. Generally, the aging time can be in a range from any minimum time disclosed herein to any maximum time disclosed herein. Accordingly, suitable non-limiting ranges for the catalyst system mixture aging time can range from 5 minutes to 6 hours, from 10 minutes to 4 hours, from 10 minutes to 2 hours, from 15 minutes to 2 hours, from 20 minutes to 2 hours, from 20 minutes to one hour, from 5 seconds to 48 hours, from 10 seconds to 36 hours, from 30 seconds to 24 hours, from 1 minute to 18 hours, from 5 minutes to 6 hours, from 10 minutes to 4 hours, or from 20 minutes to 2 hours. Other appropriate ranges for the catalyst system mixture aging time are readily apparent from this disclosure. In a non-limiting embodiment, a substantial absence of ethylene can be a maximum molar ratio of ethylene to chromium of the chromium component of 5:1, 4:1, 3:1, 2:1, 1:1, 0.5:1, 0.25:1, or 0.1:1. In some non-limiting embodiments, the substantial absence of ethylene can be a maximum ethylene partial pressure 10 psi (69 kPa), 5 psi (34 kPa), 4 psi (28 kPa), 3 psi (21 kPa), 2 psi (14 kPa), 1 psi (7 kPa), or 0.5 psi (3.4 kPa).

In aspects and/or embodiments, the catalyst system mixture aging time provided via a process according to this disclosure utilizing an aluminoxane (e.g., modified methylaluminoxane) having the desired 400 MHz proton NMR characteristics can be reduced relative to the same process utilizing an aluminoxane (e.g., a modified methylaluminoxane) which does not have the desired 400 MHz proton NMR characteristics. In embodiments, the catalyst system mixture aging time is reduced by at least 5, 10, 15, 20, or 25% relative to a process not utilizing the specific aluminoxane (e.g., a process using MMAO-3A). Characteristics of the different aluminoxane (e.g., a different modified methylaluminoxane) which does not have the desired 400 MHz proton NMR characteristics are described herein and can be utilized in any aspect or embodiment calling for the different aluminoxane (e.g., a different modified methylaluminoxane).

In further embodiments, the catalyst system mixture can be aged at any suitable temperature, ranging from sub-ambient temperatures, to ambient temperature (approximately 25° C.), to elevated temperatures. While not being limited thereto, the catalyst system mixture can be aged at a temperature in a range from 0° C. to 100° C., from 10° C. to 75° C., from 15° C. to 60° C., or from 20° C. to 50° C. In these and other embodiments, these temperature ranges also are meant to encompass circumstances where the catalyst system mixture can be aged at a series of different temperatures, instead of at a single fixed temperature, falling within the respective ranges.

In an embodiment, the catalyst system can be formed by contacting an organic liquid medium with the chromium component (any described herein) and the aluminoxane (any described herein). In an embodiment, the organic liquid medium can be any organic reaction medium described herein. In embodiments where the catalyst system can be formed by contacting an organic liquid medium with the chromium component (any described herein) and the aluminoxane, the chromium component to organic liquid medium weight ratio can range from 1:100 to 1:15,000, or 1:150 to 1:10,000.

In some embodiments, the process can further comprise removing a reaction zone effluent comprising the oligomer product from the reaction zone. In some embodiments, the reaction zone effluent can be treated with a catalyst system deactivating agent to produce a catalyst system deactivated reaction zone effluent. In further embodiments, all or a portion of the oligomer product can be recovered from the reaction zone effluent or deactivated reaction zone effluent. Generally, the all or a portion of the oligomer product (e.g., hexenes and/or octenes) can be recovered from the reaction zone effluent or deactivated reaction zone effluent via techniques known in the art with the aid of this disclosure (e.g., distillation, flashing, absorption, stripping), by-product separation and/or isolation, and/or any steps which can facilitate the handling of the reaction zone effluent and the isolation of the desired ethylene oligomers.

In any aspect and/or embodiment, ethylene, the catalyst system, and optionally, hydrogen can be periodically or continuously introduced into the reaction zone, and a reaction zone effluent comprising the oligomer product can be periodically or continuously removed from the reaction zone.

The reaction zone of any process described herein can comprise any reactor which can oligomerize ethylene to an oligomer product. In an embodiment, the reaction zone of any process, system, or reaction system described herein can comprise a stirred tank reactor, a plug flow reactor, or any combination thereof; alternatively, a stirred tank reactor; or alternatively, a plug flow reactor. In an embodiment, the reaction zone of any process, system, or reaction system described herein can comprise an autoclave reactor, continuous stirred tank reactor, a loop reactor, a gas phase reactor, a solution reactor, a tubular reactor, a recycle reactor, a bubble reactor, or any combination thereof; alternatively, autoclave reactor; alternatively, stirred tank reactor; alternatively, a loop reactor; alternatively, a gas phase reactor; alternatively, a solution reactor; alternatively, a tubular reactor; alternatively, a recycle reactor; or alternatively, a bubble reactor. In some embodiments, the reaction zone can comprise multiple reactors; or alternatively, only on reactor. When multiple reactors are present, each of the reactors can be the same or different types of reactors. The reaction zone can comprise single or multiple reactors of any of the types disclosed herein operating in batch or continuous mode; or alternatively, in continuous mode.

Generally, the oligomer product that can be produced using the processes described herein can be formed at conditions (or alternatively, the reaction zone can have any conditions) which can 1) facilitate oligomer product formation, 2) provide a desired oligomer product formation rate, 3) provide acceptable catalyst system productivity, 4) provide acceptable oligomer selectivity, and/or 5) provide acceptable polymer formation. In an embodiment, conditions under which the oligomer product can be formed (or alternatively, the reaction zone can have conditions) that can include one or more of catalyst system component ratios, chromium concentration, pressure, ethylene partial pressure, ethylene concentration, presence of hydrogen (and its partial pressure, hydrogen to ethylene mass ratio, and/or hydrogen to chromium mass ratio), temperature, reaction time, single pass ethylene conversion, and catalyst system productivity. Catalyst system component ratios, chromium concentration, pressure, ethylene partial pressure, ethylene concentration, presence of hydrogen (and its partial pressure and/or hydrogen to ethylene weight ratio), temperature, reaction time, single pass ethylene conversion, and catalyst system productivity are independently described herein and these independent descriptions can be used without limitation, and in any combination, to describe the process and/or reaction zone conditions at which the oligomer product can be formed for any of the processes described herein.

The selective ethylene oligomerization processes using the catalyst systems disclosed herein may be sensitive to specific reactor feed conditions. For example, polymer can form with use of the disclosed selective ethylene oligomerization catalyst systems when concentrated portions of ethylene are contacted with a catalyst system. The contacting of a high concentration of ethylene with the selective ethylene oligomerization catalyst system can make polymer plugging and/or fouling of reaction zone components a significant limiting factor in oligomer production. It has also been found that the amount of polymer in the reaction zone during operation of a selective olefin oligomerization reaction can be reduced, the hexenes and/or octenes productivity and/or production increased, and fouling and/or plugging of reaction zone and/or reaction system components avoided by contacting ethylene with an organic reaction medium to form an ethylene feedstock mixture prior to ethylene contacting the catalyst system, as described in U.S. patent application Ser. No. 15/166,991, filed May 27, 2016.

In the disclosed processes, ethylene can be contacted with at least a portion of the organic reaction medium to form an ethylene feedstock mixture prior to contacting ethylene with the catalyst system. In these processes, the catalyst system and the ethylene feedstock mixture can be contacted prior to entering the reaction zone or the catalyst system can be introduced into the reaction zone separately from the ethylene feedstock mixture; alternatively, the catalyst system and the ethylene feedstock mixture can be contacted prior to entering the reaction zone; or alternatively, the catalyst system can be introduced into the reaction zone separately from the ethylene feedstock mixture. In an embodiment of the processes disclosed herein, substantially all of the ethylene can be contacted with the catalyst system and/or introduced/fed to the reaction zone via the ethylene feedstock mixture; or alternatively, substantially all of the ethylene can be contacted with at least a portion of the organic reaction medium prior to the ethylene contacting the catalyst system. For example, the catalyst system can be introduced into the reaction zone separately from the ethylene feedstock mixture. Alternatively, the catalyst system and the ethylene feedstock mixture can be contacted prior to entering the reaction zone. By "substantially all" it is meant that at least 95, 97, 99, 99.5, 99.75, or 99.9 mol % of the ethylene fed to the reaction zone in the process described herein is the ethylene feedstock mixture (or alternatively, contacts the at least a portion of the organic reaction medium prior to contacting the catalyst system).

As described herein, aspects and embodiments of the herein disclosed processes can include combining ethylene and organic reaction medium to form an ethylene feedstock mixture. The minimum ethylene concentration in the ethylene feedstock mixture can be 4 mass %, 10 mass %, 25 mass %, 35 mass %, or 40 mass %, based upon the total mass in the ethylene feedstock mixture; alternatively or additionally, at a maximum ethylene concentration of the ethylene feedstock mixture of 65 mass %, 60 mass %, 55 mass %, 50 mass %, or 48 mass %, based upon the total mass in the ethylene feedstock mixture. In an embodiment, ethylene concentration in the ethylene feedstock mixture can be from any minimum ethylene concentration in the ethylene feedstock mixture disclosed herein to any maximum ethylene concentration in the ethylene feedstock mixture disclosed herein. In some non-limiting embodiments, the ethylene concentration in the ethylene feedstock mixture can be in a range of from 4 mass % to 60 mass %, from 10 mass % to 60 mass %, from 25 mass % to 55 mass %, from 35 mass % to 50 mass %, or from 40 mass % to 48 mass %, based upon the total mass in the ethylene feedstock mixture. Other ethylene concentrations in the ethylene feedstock mixture ranges that can be utilized are readily apparent to those skilled in the art with the aid of this disclosure.

The ethylene feedstock mixture can be contacted with the catalyst system prior to introduction of the ethylene feedstock mixture into the reaction zone. The separately fed ethylene feedstock mixture can be substantially free of the catalyst system. By "substantially free" it is meant that the ethylene feedstock mixture has equal to or less than 1.0, 0.9, 0.8, 0.7, 0.6, 0.5, 0.4, 0.3, 0.2, or 0.1 wt. % of the catalyst system present based on the total weight of the catalyst system entering the reaction zone.

In an embodiment, the oligomer product can be formed (or the reaction zone can operate) at a minimum aluminum of the aluminoxane to chromium of the chromium component (e.g., $N^2$-phosphinyl formamidine chromium compound complex, the $N^2$-phosphinyl amidine chromium compound complex, and/or the $N^2$-phosphinyl guanidine chromium compound complex) molar ratio (i.e., minimum Al to Cr molar ratio) of 10:1, 50:1, 75:1, or 100:1; alternatively or additionally, at a maximum aluminum of the aluminoxane to chromium of the chromium component (e.g., $N^2$-phosphinyl formamidine chromium compound complex, the $N^2$-phosphinyl amidine chromium compound complex, and/or the $N^2$-phosphinyl guanidine chromium compound complex) molar ratio (i.e., maximum Al to Cr molar ratio) of 5,000:1, 3,000:1, 2,000:1, 1,500:1, or 1,000:1. In an embodiment, the oligomer product can be formed (or the reaction zone can operate) at an Al to Cr molar ratio ranging from any minimum Al to Cr molar ratio disclosed herein to any maximum Al to Cr molar ratio disclosed herein. In a non-limiting embodiment, the Al to Cr molar ratio can range from 10:1 to 5,000:1, from 50:1 to 3,000:1, from 50:1 to 3,000:1, from 75:1 to 2,000:1, from 100:1 to 2,000:1, of from 100:1 to 1,000:1. Other Al to Cr molar ratio ranges that can be utilized are readily apparent to those skilled in the art with the aid of this disclosure.

In an embodiment, the oligomer product can be formed (or the reaction zone can operate) at a minimum reaction zone chromium concentration of the chromium component (e.g., $N^2$-phosphinyl formamidine chromium compound complex, the $N^2$-phosphinyl amidine chromium compound complex, and/or the $N^2$-phosphinyl guanidine chromium compound complex) concentration (i.e., minimum chromium concentration) of $1 \times 10^{-6}$ Cr equivalents/liter, $1 \times 10^{-5}$ Cr equivalents/liter, or $5 \times 10^{-4}$ Cr equivalents/liter; alternatively or additionally, at a maximum reaction zone chromium concentration of the chromium component (e.g., $N^2$-phosphinyl formamidine chromium compound complex, the $N^2$-phosphinyl amidine chromium compound complex, and/or the $N^2$-phosphinyl guanidine chromium compound complex) concentration (i.e., maximum chromium concentration) of 1 Cr equivalents/liter, $5 \times 10^{-1}$ Cr equivalents/liter, or $1 \times 10^{-1}$ Cr equivalents/liter. In an embodiment, the oligomer product can be formed (or the reaction zone can operate) at a reaction zone chromium concentration ranging from any minimum chromium concentration disclosed herein to any maximum chromium concentration disclosed herein. In a non-limiting embodiment, the reaction zone chromium concentration can range from $1 \times 10^{-6}$ Cr equivalents/liter to 1 Cr equivalents/liter, from $1 \times 10^{-5}$ Cr equivalents/liter to $5 \times 10^{-1}$ Cr equivalents/liter, from $5 \times 10^{-4}$ Cr equivalents/liter to $1 \times 10^{-1}$ Cr equivalents/liter. Other chromium concentration ranges that can be utilized are readily apparent to those skilled in the art with the aid of this disclosure.

In an embodiment, the oligomer product can be formed (or the reaction zone can operate) at a minimum pressure of 5 psi (34.5 kPa), 50 psi (345 kPa); 100 psi (689 kPa), 150 psi (1.03 MPa), 250 psi (1.72 MPa), 500 psi (3.5 MPa), or 600 psi (4.1 MPa); alternatively of additionally, at a maximum pressure of 2,500 psi (17.2 MPa), 2,000 psi (13.8 MPa), 1,500 psi (10.3 MPa), 1400 psi (9.65 MPa), 1250 psi (8.62 MPa), or 1000 psi (6.89 MPa). In an embodiment, the oligomer product can be formed (or the reaction zone can operate) at a pressure ranging from any minimum pressure disclosed herein to any maximum pressure disclosed herein. In some non-limiting embodiments, the oligomer product can be formed (or the reaction zone can operate) at a pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 500 psi (3.5 MPa) to 1500 psi (10.3 MPa), from 150 psi (1.03 MPa) to 1250 psi (8.62 MPa), from 250 psi (1.72 MPa) to 1000 psi (6.89 MPa), or from 600 psi (4.1 MPa) to 1400 psi (9.65 MPa). Other pressure ranges that can be utilized are readily apparent to those skilled in the art with the aid of this disclosure.

In an embodiment, the oligomer product can be formed (or the reaction zone can operate) at a minimum ethylene partial pressure of 5 psi (34.5 kPa), 50 psi (345 kPa); 100 psi (689 kPa), 150 psi (1.03 MPa), 250 psi (1.72 MPa), or 500 psi (3.5 MPa); alternatively or additionally, at a maximum ethylene partial pressure of 2,500 psi (17.2 MPa), 2,000 psi (13.8 MPa), 1,500 psi (10.3 MPa), 1250 psi (8.62 MPa), or 1000 psi (6.89 MPa). In an embodiment, the oligomer product can be formed (or the reaction zone can operate) at an ethylene partial pressure ranging from any minimum ethylene partial pressure disclosed herein to any maximum ethylene partial pressure disclosed herein. In some non-limiting embodiments, the oligomer product can be formed (or the reaction zone can operate) at an ethylene partial pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 500 psi (3.5 MPa) to 1500 psi (10.3 MPa), from 150 psi (1.03 MPa) to 1250 psi (8.62 MPa), from 150 psi (1.03 MPa) to 1250 psi (8.62 MPa), or from 250 psi (1.72 MPa) to 1000 psi (6.89 MPa). Other ethylene partial pressure ranges are readily apparent to those skilled in the art with the aid of this disclosure.

In an embodiment, the oligomer product can be formed (or the reaction zone can operate) at a minimum ethylene concentration of 4 mass %, 10 mass %, 25 mass %, 35 mass %, or 40 mass % based upon the total mass in the reaction zone; alternatively or additionally, at a maximum ethylene concentration of 70 mass %, 65 mass %, 60 mass %, 55 mass %, 50 mass %, 48 mass % based upon the total mass in the reaction zone. In an embodiment, the oligomer product can be formed (or the reaction zone can operate) at an ethylene concentration ranging from any minimum ethylene concentration disclosed herein to any maximum ethylene concentration disclosed herein. In some non-limiting embodiments, the oligomer product can be formed (or the reaction zone can operate) at an ethylene concentration from 4 mass % to 70 mass %, from 4 mass % to 60 mass %, from 10 mass % to 60 mass %, from 25 mass % to 55 mass %, 35 mass % to 50 mass %, or 40 mass % to 48 mass % based upon the total mass in the reaction zone. Other ethylene concentration ranges that can be utilized are readily apparent to those skilled in the art with the aid of this disclosure.

In an embodiment, the oligomer product can be formed (or the reaction zone can operate) at a minimum ethylene:chromium mass ratio of 50,000:1, 150,000:1, 250,000:1, or 400,000:1; alternatively, or additionally, at a maximum ethylene:chromium mass ratio of 5,000,000:1, 2,500,000:1, 1,500,000:1, or 1,000,000:1. In an embodiment, the oligomer product can be formed (or the reaction zone can operate) at an ethylene:chromium mass ratio ranging from any minimum ethylene:chromium mass ratio disclosed herein to any maximum ethylene:chromium mass ratio disclosed herein. In some non-limiting embodiments, the oligomer product can be formed (or the reaction zone can operate) at an ethylene:chromium mass ratio from 50,000:1 to 5,000,000:1, 150,000:1 to 2,500,000:1, 250,000:1 to 1,500,000:1, or 400,000:1 to 1,000,000:1. Other ethylene:chromium mass ratio ranges that can be utilized are readily apparent to those skilled in the art with the aid of this disclosure.

In an embodiment wherein hydrogen is utilized, the oligomer product can be formed (or the reaction zone can operate) at a minimum hydrogen partial pressure of 1 psi (6.9 kPa), 2 psi (14 kPa); 5 psi (34 kPa), 10 psi (69 kPa), or 15 psi (103 kPa); alternatively or additionally at a maximum hydrogen partial pressure of 200 psi (1.4 MPa), 150 psi (1.03 MPa), 100 psi (689 kPa), 75 psi (517 kPa), or 50 psi (345 kPa). In an embodiment, the oligomer product can be formed (or the reaction zone can operate) at a hydrogen partial pressure ranging from any minimum hydrogen partial pressure disclosed herein to any maximum hydrogen partial pressure disclosed herein. In some non-limiting embodiments wherein hydrogen is utilized, the oligomer product can be formed (or the reaction zone can operate) at a hydrogen partial pressure from 1 psi (6.9 kPa) to 200 psi (1.4 MPa), from 5 psi (34 kPa) to 150 psi (1.03 MPa), from 10 psi (69 kPa) to 100 psi (689 kPa), or from 15 psi (100 kPa) to 75 psi (517 kPa). Other hydrogen partial pressure ranges that can be utilized are readily apparent to those skilled in the art with the aid of this disclosure.

In an embodiment wherein hydrogen is utilized, the oligomer product can be formed (or the reaction zone can operate) at a minimum hydrogen to ethylene mass ratio of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); alternatively or additionally, at a maximum hydrogen to ethylene mass ratio can be (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). In an embodiment, the oligomer product can be formed (or the reaction zone can operate) at a hydrogen to ethylene mass ratio ranging from any minimum hydrogen to ethylene mass ratio disclosed herein to any maximum hydrogen to ethylene mass ratio disclosed herein. In some non-limiting embodiments, the oligomer product can be formed (or the reaction zone can operate) at a hydrogen to ethylene mass ratio from (0.05 g hydrogen)/(kg ethylene) to (5 g hydrogen)/(kg ethylene), from (0.25 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), or from (0.5 g hydrogen)/(kg ethylene) to (2 g hydrogen)/(kg ethylene). Other hydrogen to ethylene mass ratio ranges that can be utilized are readily apparent to those skilled in the art with the aid of this disclosure.

In an embodiment, the oligomer product can be formed (or the reaction zone can operate) at a minimum hydrogen:chromium mass ratio of 1:1, 50:1, 100:1, or 200:1; alternatively or additionally, at a maximum hydrogen:chromium mass ratio of 100,000:1, 50,000:1, 10,000:1, or 3,000:1. In an embodiment, the oligomer product can be formed (or the reaction zone can operate) at a hydrogen:chromium mass ratio ranging from any minimum hydrogen:chromium mass ratio disclosed herein to any maximum hydrogen:chromium mass ratio disclosed herein. In some non-limiting embodiments, the oligomer product can be formed (or the reaction zone can operate) at a hydrogen:chromium mass ratio from 1:1 to 100,000:1, 50:1 to 50,000:1, 100:1 to 10,000:1, or 200:1 to 3,000:1. Other hydrogen:chromium mass ratio ranges that can be utilized are readily apparent to those skilled in the art with the aid of this disclosure.

In an embodiment, the oligomer product can be formed (or the reaction zone can operate) at a minimum temperature of 0° C., 25° C., 40° C., or 50° C.; alternatively, or additionally, at a maximum temperature of 200° C., 150° C., 100° C., or 90° C. In an embodiment, the oligomer product can be formed (or the reaction zone can operate) at a temperature ranging from any minimum temperature disclosed herein to any maximum temperature disclosed herein. In some non-limiting embodiments, the oligomer product can be formed (or the reaction zone can operate) at a temperature from 0° C. to 200° C., from 25° C. to 150° C., from 40° C. to 100° C., from 50° C. to 100° C., or from 50° C. to 90° C. Other temperature ranges that can be utilized are readily apparent to those skilled in the art with the aid of this disclosure.

The reaction time (or residence time) in the reaction zone can comprise any time that can produce the desired quantity of oligomer product; alternatively, any reaction time (or residence time) that can provide a desired catalyst system productivity; alternatively, any reaction time (or residence time) that can provide a desired ethylene conversion. Relating to forming the oligomer product, the oligomer product can be formed over a period of time (or an average period of time time) that can produce the desired quantity of olefin product or polymer product, provide a desired catalyst system productivity, and/or provide a desired conversion of monomer. In some embodiments, the time (or average time) can range from 1 minute to 5 hours; alternatively, ranges from 5 minutes to 2.5 hours; alternatively, ranges from 10 minutes to 2 hours; or alternatively, ranges from 15 minutes to 1.5 hours. In some embodiments (in continuous process embodiments), the reaction time (or residence time) can be stated as an average reaction time (or average residence time) and can range from 1 minute to 5 hours; alternatively, ranges from 5 minutes to 2.5 hours; alternatively, ranges from 10 minutes to 2 hours; or alternatively, ranges from 15 minutes to 1.5 hours.

In an embodiment, the processes described herein can have an ethylene conversion of at least 30%, 35%, 40%, or 45%.

Depending upon the catalyst system utilized, the processes described herein can be an ethylene oligomerization process, an ethylene trimerization process, an ethylene tetramerization process, or an ethylene trimerization and tetramerization process; alternatively, an ethylene oligomerization process; alternatively, an ethylene trimerization process; alternatively, an ethylene tetramerization process; or alternatively an ethylene trimerization and tetramerization process. In ethylene trimerization aspects and/or embodiments, the oligomer product can comprise at least 70 wt. % hexenes, at least 75 wt. % hexenes, at least 80 wt. % hexenes, at least 85 wt. % hexenes, or at least 90 wt. % hexenes based upon the weight of the oligomer product. In some ethylene trimerization aspects and/or embodiments, the oligomer product can comprise from 70 wt. % to 99.8 wt. % hexenes, from 75 wt. % to 99.7 wt. % hexenes, or from 80 wt. % to 99.6 wt. % hexenes based upon the weight of the oligomer product. In ethylene tetramerization aspects and/or embodiments, the oligomer product can comprise at least 70 wt. % octenes, at least 75 wt. % octenes, at least 80 wt. % octenes, at least 85 wt. % octenes, or at least 90 wt. % octenes based upon the weight of the oligomer product. In some ethylene tetramerization aspects and/or embodiments, the oligomer product can comprise from 70 wt. % to 99.8 wt. % octenes, from 75 wt. % to 99.7 wt. % octenes, or from 80 wt. % to 99.6 wt. % octenes based upon the weight of the oligomer product. In ethylene trimerization and tetramerization aspects and/or embodiments, the oligomer product can comprise at least 70 wt. % hexenes and octenes, at least 75 wt. % hexenes and octenes, at least 80 wt. % hexenes and octenes, at least 85 wt. % hexenes and octenes, or at least 90 wt. % hexenes and octenes based upon the weight of the oligomer product. In some ethylene trimerization and tetramerization aspects and/or embodiments, the oligomer product can comprise from 70 wt. % to 99.8 wt. % hexenes and octenes, from 75 wt. % to 99.7 wt. % hexenes and octenes, or from 80 wt. % to 99.6 wt. % hexenes and octenes based upon the weight of the oligomer product.

In ethylene oligomerization, ethylene trimerization, or ethylene trimerization and tetramerization aspects and/or embodiments, the ethylene trimer (or $C_6$ portion of the oligomer product) can comprise at least 85 wt. % 1-hexene; alternatively, at least 87.5 wt. % 1-hexene; alternatively, at least 90 wt. % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene by weight of the ethylene trimer (or $C_6$ portion of the oligomer product). In some ethylene oligomerization, ethylene trimerization, or ethylene trimerization and tetramerization aspects and/or embodiments, the ethylene trimer (or $C_6$ portion of the oligomer product) can comprise from 85 wt. % to 99.9 wt. % 1-hexene; alternatively, from 87.5 wt. % to 99.9 wt. % 1-hexene; alternatively, from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. % 1-hexene; or alternatively, from 98 wt. % to 99.9 wt. % 1-hexene by weight of the ethylene trimer (or $C_6$ portion of the oligomer product).

In ethylene oligomerization, ethylene tetramerization, or ethylene trimerization and/or tetramerization aspects and/or embodiments, the ethylene tetramer (or $C_8$ portion of the oligomer product) can comprise at least 85 wt. % 1-octene; alternatively, at least 87.5 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively at least 98 wt. % 1-octene by weight of the ethylene tetramer (or $C_8$ portion of the oligomer product). In some ethylene oligomerization, ethylene tetramerization, or ethylene trimerization and/or tetramerization aspects and/or embodiments, the ethylene tetramer (or $C_8$ portion of the oligomer product) can comprise from 85 wt. % to 99.9 wt. % 1-octene; alternatively, from 87.5 wt. % to 99.9 wt. % 1-octene; alternatively, from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; or alternatively, from 98 wt. % to 99.9 wt. % 1-octene by weight of the ethylene tetramer (or $C_8$ portion of the oligomer product).

The processes described herein can provide various advantages. In aspects and/or embodiments, such advantages can include, without limitation, increased catalyst system productivity (defined as g ($C_6+C_8$)/g Cr or g ($C_6+C_8$)/g Al)), reduced activation time, reduced $C_{10}$ to $C_{18}$ oligomer production, reduced polymer production, reduced polymer Mw, a reduced Mw maximum peak of the polymer, or any combination thereof. Thus, in embodiments, relative to the same process utilizing an aluminoxane (e.g., a modified methylaluminoxane) which does not have the desired 400 MHz proton NMR characteristics described herein: (a) a catalyst system ($C_6+C_8$) productivity [defined as g ($C_6+C_8$)/g Cr or g ($C_6+C_8$)/g Al] can be increased; (b) a liquid oligomer portion of the oligomer product can comprise a reduced amount of $C_{10}$ to $C_{18}$ oligomers; (c) the oligomer product can comprise a polymer having a lower Mw; (d) a Mw maximum peak of the polymer can be reduced; (e) a quantity of polymer in the oligomer product can be reduced; and/or (f) any combination thereof.

In some aspects and/or embodiments (but not necessarily all aspects and/or embodiments), the processes utilizing an aluminoxane (e.g., modified methylaluminoxane) having the desired 400 MHz proton NMR properties described herein (e.g., MMAO-20) can have a higher catalyst system productivity relative to the same processes which utilize an aluminoxane (e.g., a modified methylaluminoxane) which does not have the desired 400 MHz proton NMR characteristics described herein. Generally, catalyst system productivity is defined as a mass of a liquid oligomer product (e.g., $C_6$ product, $C_8$ product, ($C_6+C_8$) product, or total liquid product) formed per mass of chromium or aluminum. In some embodiments, the processes utilizing the aluminoxane (e.g., modified methylaluminoxane) having the desired 400 MHz proton NMR properties described herein (e.g., MMAO-20) can have a catalyst system productivity of greater than 10,000, 50,000, 100,000, 150,000, 200,000, 300,000, or 400,000 g ($C_6+C_8$)/g Cr. In some embodiments (but not necessarily all embodiments), the processes utilizing the aluminoxane (e.g., modified methylaluminoxane) having the 400 MHz proton NMR properties described herein (e.g., MMAO-20) can have a higher catalyst system productivity relative to the same processes which utilize an aluminoxane (e.g., modified methylaluminoxane) which does not have the desired 400 MHz proton NMR characteristics described herein. In an embodiment (but not necessarily all embodiments), the catalyst system productivity can be increased by at least 5%, 7.5%, 10%, or 12.5%. In some embodiments, there can be at least a 10, 20, or 30% increase in the catalyst system $C_6+C_8$ productivity.

In some aspects and/or embodiments (but not necessarily all aspects and/or embodiments), the processes utilizing the aluminoxane (e.g., modified methylaluminoxane) having the desired 400 MHz proton NMR characteristic described herein (e.g., MMAO-20) can produce a liquid oligomer portion of the oligomer product that can comprise a reduced amount of $C_{10}$ to $C_{18}$ oligomers relative to the same processes which utilize an aluminoxane (e.g., a modified methylaluminoxane) which does not have the desired 400 MHz proton NMR characteristics described herein. In embodiments, the processes utilizing the aluminoxane (e.g., modified methylaluminoxane) having the desired 400 MHz proton NMR characteristics described herein (e.g., MMAO-20) can have at least a 5, 10, 15, or 20% reduction in the $C_{10}$ to $C_{18}$ oligomers in the liquid oligomer product.

In some aspects and/or embodiments (but not necessarily all aspects and/or embodiments), the processes utilizing the aluminoxane (e.g., modified methylaluminoxane) having the desired 400 MHz proton NMR characteristics described herein (e.g., MMAO-20) can have a reduced quantity of polymer (mass of polymer per gram of oligomer product) relative to the same processes which utilize an aluminoxane (e.g., a modified methylaluminoxane) which does not have the desired 400 MHz proton NMR characteristics described herein. In an embodiment (but not all embodiments), the quantity of polymer (mass of polymer per mass of oligomer product) can be reduced by at least 10%, 25%, 30%, 40%, 50%, 60%, 70%, or 80%.

In some aspects and/or embodiments (but not necessarily all aspects and/or embodiments), the polymer produced via the processes utilizing the aluminoxane (e.g., modified methylaluminoxane) having the desired 400 MHz proton NMR properties described herein (e.g., MMAO-20) can have a reduced Mw maximum peak in the molecular weight relative to polymer produced and/or a reduction in the polymer Mw relative to the same processes which utilize an aluminoxane (e.g., a modified methylaluminoxane) which does not have the desired 400 MHz proton NMR characteristics described herein. In aspects and/or embodiments, there can be at least a 10, 15, 20, or 25% reduction in the molecular weight of the Mw maximum peak of the polymer. In other aspects and/or embodiments, there can be at least a 10, 15, 20, or 25% a reduction in the polymer Mw.

In embodiments, relative to the same process utilizing an aluminoxane (e.g., modified methylaluminoxane) which does not have the desired 400 MHz proton NMR characteristics described herein, a reaction zone on-line time can be increased, an amount of 1-hexene in the $C_6$ fraction of the oligomer product can be increased, a hexene selectivity can be increased, a ($C_6+C_8$) selectivity can be increased, or any combination thereof. Thus, the processes utilizing the aluminoxane (e.g., modified methylaluminoxane) having the desired 400 MHz proton NMR characteristics described herein (e.g., MMAO-20) can have an increased reaction zone on-line time, an increased amount of 1-hexene in the $C_6$ fraction of the oligomer product, an increased hexene selectivity, and/or an increased $(C_6+C_8)$ selectivity relative to the same process utilizing an aluminoxane (e.g., modified methylaluminoxane) which does not have the desired 400 MHz proton NMR characteristics described herein. In some aspects and/or embodiments (but not necessarily all aspects and/or embodiments), relative to the same process utilizing an aluminoxane (e.g., modified methyl aluminoxane) which does not have the desired 400 MHz proton NMR characteristics described herein, a reaction zone on-line time can be increased by at least 10%, 25%, 50%, 100%, 200%, 300%, 400%, 500%. In some aspects and/or embodiments (but not necessarily all aspects and/or embodiments), relative to the same process utilizing an aluminoxane (e.g., modified methyl aluminoxane) which does not have the desired 400 MHz proton NMR characteristics described herein, an amount of 1-hexene in the $C_6$ fraction of the oligomer product can be increased by 0.2, 0.3, 0.4, 0.5, or 0.6%. In some aspects and/or embodiments (but not necessarily all aspects and/or embodiments), relative to the same process utilizing an aluminoxane (e.g., modified methyl aluminoxane) which does not have the desired 400 MHz proton NMR characteristics described herein, a hexene selectivity can be increased by 1, 2, 3, or 4%. The hexene selectivity is defined as the mass percent of hexene in the liquid oligomer product. In some aspects and/or embodiments (but not necessarily all aspects and/or embodiments), relative to the same process utilizing an aluminoxane (e.g., modified methyl aluminoxane) which does not have the desired 400 MHz proton NMR characteristics described herein, a $(C_6+C_8)$ selectivity can be increased by 0.2, 0.3, 0.4, 0.5, or 0.6%. The $(C_6+C_8)$ selectivity is defined as the mass percent of hexenes and octenes in the liquid oligomer product.

In any embodiments, wherein features of the processes utilizing an aluminoxane (e.g., modified methylaluminoxane) having the desired 400 MHz proton NMR properties described herein (e.g., MMAO-20) are described as relative to the same processes which utilize an aluminoxane (e.g., a modified methylaluminoxane) which does not have the desired 400 MHz proton NMR characteristics, the aluminoxane (e.g., a modified methylaluminoxane) which does not have the desired 400 MHz proton NMR characteristics can comprise, can consist essentially of, or can be, an aluminoxane (e.g., a modified methylaluminoxane having (a) a ratio of peaks found in the range of −0.86 ppm to −0.74 ppm to peaks found in a range of −0.03 ppm to 0.07 ppm greater than 2.85; (b) a ratio of peaks found in the range of −0.03 ppm to 0.025 ppm to peaks found in a range of 0.025 ppm to 0.07 ppm greater than 16:1; (c) the ratio of peaks found in the range of −0.86 ppm to −0.78 ppm to peaks found in the range of −0.78 ppm to −0.74 ppm greater than 6.7:1; or any combination thereof; or alternatively, a modified methylaluminoxane having (a) a ratio of peaks found in the range of −0.86 ppm to −0.74 ppm to peaks found in a range of −0.03 ppm to 0.07 ppm greater than 2.85; (b) a ratio of peaks found in the range of −0.03 ppm to 0.025 ppm to peaks found in a range of 0.025 ppm to 0.07 ppm greater than 16:1; and (c) the ratio of peaks found in the range of −0.86 ppm to −0.78 ppm to peaks found in the range of −0.78 ppm to −0.74 ppm greater than 6.7:1). In some embodiments, the aluminoxane (e.g., a modified methylaluminoxane) which does not have the desired 400 MHz proton NMR characteristics can comprise, can consist essentially of, or can be, MMAO-3A, available from AkzoNobel Functional Chemicals B.V., Netherlands. The Product Data Sheet for MMAO-3A, OMS 66721.12/December 2014, provides the product description and compositional information about MMAO-3A provided in Table 5 below. This product description and composition information can be utilized in any aspect or embodiment disclosed herein to further describe the aluminoxane (e.g., a modified methylaluminoxane) that does not have the desired 400 MHz proton NMR characteristics described herewith.

TABLE 5

Composition and Product Description for an Aluminoxane (e.g., Modified Methylaluminoxane) not having Desired 400 MHz Proton NMR Characteristics

| Product Description | | Composition[a] | |
|---|---|---|---|
| Approx. Molecular Formula | $[(CH_3)_{0.7}(isoC_4H_9)_{0.3}AlO]_n$ | Methane, molar %[b] | 62.0-78.0 |
| Process Route | hydrolytic | Isobutane, molar %[b] | 22.0-38.0 |
| Approx. Molecular Weight | 70.7 | Hydrogen, molar %[b] | 3.0 max |
| CAS No. | 146905-79-5 | Others, molar %[b, c] | 3.0 max |
| EINECS/ELINCS no. | 931-024-8 | Aluminum, wt. %[d] | 6.0-8.0 |
| | | Active Al[e] | 36-48 |

[a]Data for heptane solution containing 7 wt. % aluminum.
[b]Calculated by gas chromatography of Hydrocarbons and hydrogen obtained upon hydrolysis of aluminoxane.
[c]Other components include ethane, propane, isobutylene, and n-butane
[d]Determined by titration of aqueous hydrolyzate.
[e]Determined by pyridine titration method.

The processes described herein can use an organic liquid medium and/or an organic reaction medium. Generally, the organic liquid medium and/or organic reaction medium can act as a solvent and/or a diluent in the processes described herein. In some embodiments, the organic liquid medium and the organic reaction medium can be the same; in some embodiments, the organic liquid medium and the organic reaction medium can be different. In an aspect, the organic liquid medium and/or the organic reaction medium can be a hydrocarbon, a halogenated hydrocarbon, or a combination thereof. Hydrocarbons and halogenated hydrocarbons which can be used as an organic liquid medium and/or organic reaction medium can include aliphatic hydrocarbons, aromatic hydrocarbons, petroleum distillates, halogenated aliphatic hydrocarbons, halogenated aromatic hydrocarbons, or combinations thereof. Aliphatic hydrocarbons which can be useful as an organic liquid medium and/or organic reaction medium include $C_3$ to $C_{20}$ aliphatic hydrocarbons, or $C_4$ to $C_{15}$ aliphatic hydrocarbons, or $C_5$ to $C_{10}$ aliphatic hydrocarbons. The aliphatic hydrocarbons which can be used as an organic liquid medium and/or organic reaction medium can be cyclic or acyclic and/or can be linear or branched, unless otherwise specified. Non-limiting examples of suitable acyclic aliphatic hydrocarbon organic liquid mediums and/or organic reaction mediums that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), or combinations thereof. Non-limiting examples of suitable cyclic aliphatic hydrocarbons which can be used as an organic liquid medium and/or organic reaction medium include cyclohexane, and methyl cyclohexane. Aromatic hydrocarbons which can be useful as an organic liquid medium and/or organic reaction medium include $C_6$ to $C_{10}$ aromatic hydrocarbons. Non-limiting examples of suitable aromatic hydrocarbons that can be utilized singly or in any combination as an organic liquid medium and/or organic reaction medium include benzene, toluene, xylene (including ortho-xylene, meta-xylene, para-xylene, or mixtures thereof), ethylbenzene, or combinations thereof. Halogenated aliphatic hydrocarbons which can be useful as an organic liquid medium and/or organic reaction medium include $C_1$ to $C_{15}$ halogenated aliphatic hydrocarbons, $C_1$ to $C_{10}$ halogenated aliphatic hydrocarbons, or $C_1$ to $C_5$ halogenated aliphatic hydrocarbons. The halogenated aliphatic hydrocarbons which can be used as an organic liquid medium and/or organic reaction medium can be cyclic or acyclic and/or can be linear or branched, unless otherwise specified. Non-limiting examples of suitable halogenated aliphatic hydrocarbons which can be utilized as an organic liquid medium and/or organic reaction medium include methylene chloride, chloroform, carbon tetrachloride, dichloroethane, trichloroethane, and combinations thereof. Halogenated aromatic hydrocarbons which can be useful as an organic liquid medium and/or organic reaction medium include $C_6$ to $C_{20}$ halogenated aromatic hydrocarbons, or $C_6$ to $C_{10}$ halogenated aromatic hydrocarbons. Non-limiting examples of suitable halogenated aromatic hydrocarbons which can be used as a solvent include chlorobenzene, dichlorobenzene, or combinations thereof.

The choice of organic liquid medium and/or organic reaction medium can be made on the basis of convenience in processing. For example, isobutane can be chosen to be compatible with solvents and diluents used in processes using the product(s) of the process described herein (e.g., using the product for the formation of polymer in a subsequent processing step). In some embodiments, the organic liquid medium and/or organic reaction medium can be chosen to be easily separable from the one or more of the oligomer in the oligomer product. In some embodiments, an oligomer of the oligomer product can be utilized as the reaction system solvent. For example, when 1-hexene is an oligomer of an ethylene trimerization process, 1-hexene can be chosen as the reaction system solvent to decrease the need for separation.

Various aspects and embodiments described herein can refer to a substituted group or compound. In an embodiment, each substituent of any aspect or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl substituent can be a $C_1$ to $C_{10}$ hydrocarbyl group; or alternatively, a $C_1$ to $C_5$ hydrocarbyl group. In an embodiment, each hydrocarboxy group can be a $C_1$ to $C_{10}$ hydrocarboxy group; or alternatively, a $C_1$ to $C_5$ hydrocarboxy group.

In an embodiment, any halide substituent of any aspect or embodiment calling for a substituent can be a fluoride, chloride, bromide, or iodide; alternatively, a fluoride or chloride. In some embodiments, any halide substituent of any aspect or embodiment calling for a substituent can be a fluoride; alternatively, a chloride; alternatively, a bromide; or alternatively, an iodide.

In an embodiment, any hydrocarbyl substituent of any aspect or embodiment calling for a substituent can be an alkyl group, an aryl group, or an aralkyl group; alternatively, an alkyl group; alternatively, an aryl group; or alternatively, an aralkyl group. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; alternatively, an aryloxy group, or an aralkoxy group. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of any aspect or embodiment calling for a substituent can be benzoxy group.

EXAMPLES

The subject matter having been generally described, the following examples are given as particular aspects of the disclosure and to demonstrate the practice and advantages thereof. It is understood that the examples are given by way of illustration and are not intended to limit the specification or the claims in any manner.

Complex A and Complex B were prepared according to the procedures described in United States patent application publication US 2012/0309965 A1 and United States patent application publication US 2013/0331629 A1, respectively.

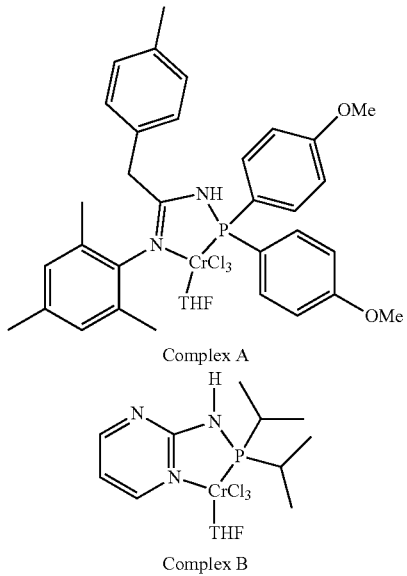

Complex A

Complex B

MMAO-20, 7 wt. % aluminum in heptanes and MMAO-3A (7 wt. % aluminum) were utilized as obtained from AkzoNobel Functional Chemicals B.V.

Anhydrous grade deuterated THF purchased from Aldrich was degassed by nitrogen purge and dried over 5A molecular sieves for 72 hours and the stored in an inert atmosphere glovebox. Ethylbenzene, anhydrous, was obtained from Sigma-Aldrich and stored over 13x molecular sieves ('mol sieves') until utilized. The first source of methylcyclohexane, anhydrous methylcyclohexane from Sigma-Aldrich, was stored over 13x mol sieves until utilized. The second source of methylcyclohexane, methylcyclohexane from Chemical Point, dried by passing it through a 13x mol sieve/reduced Cu bed and then stored over 13x mol sieves until utilized. Cyclohexane, anhydrous, was obtained from Sigma-Aldrich, passed through a 13x mol sieve/reduced Cu bed, and then stored over 13x mol sieves until utilized.

Ethylene, ultra high purity, was purified through a four bed custom built purification skid (3A Mol Sieve, SELEX-SORB® CD, SELEXSORB® COS, and PURISTAR® RG-16) to local storage, and then passed through a 13x mol sieve/reduced Cu bed prior to entering the ethylene oligomerization reactor.

Example 1: 400 MHz Proton NMR of Methylaluminoxanes

According to the supplier (Akzo Nobel) product data sheets, product description and compositional information for MMAO-20 and MMAO-3A are the same. However, differences in the performance of catalyst systems using MMAO-20 or MMAO-3A indicate that there a difference between the two aluminoxanes that is not reflected in the product data sheets. A 400 MHz proton NMR analysis of MMAO-20 and MMAO-3A was performed to determine whether there were observable differences in the 400 MHz proton NMRs of MMAO-20 and MMAO-3A.

Figure 1B:
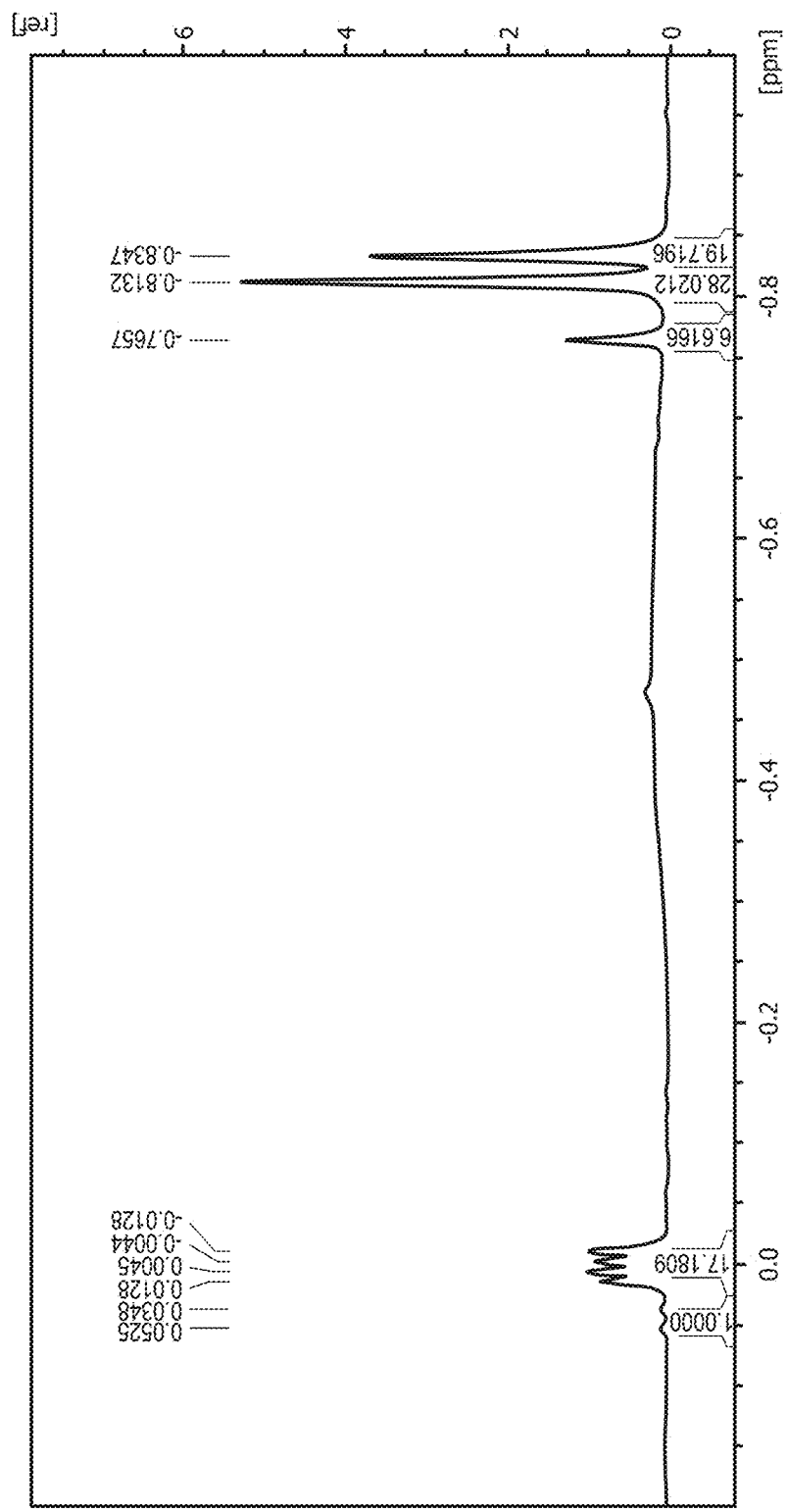
FIG. 1B shows $^1$H NMR (400 MHz) spectra for MMAO-3A.

A WILMAD® brand 5 mm-diameter NMR tube was dried in an oven at 100° C. for 24 hours and brought into an inert atmosphere glovebox. The dry 5 mm-diameter NMR tube was charged the aluminoxane, 0.5 mL of the 7 wt. % aluminum solution, and deuterated tetrahydrofuran (THF-$d_8$), 1 mL, capped with a J-Young valve, inverted several times to mix the solutions. The NMR tube was then removed from the glove box and taken to the 400 MHz NMR for NMR spectra acquisition on a Bruker 400 MHz NMR. The 400 MHz proton NMR acquisition parameters utilized are provided in Table 6. FIGS. 1A and 1B provide the 400 MHz proton NMR for MMAO-20 and MMAO-3A, respectively. Table 7 provides the peak integrations for the pertinent peaks in the range of −1.0 ppm to 0.2 ppm from the 400 MHz proton NMR of MMAO-20 and MMAO-3A.

As can be seen in Table 7, there are distinctive differences in the ratios of the peaks found in the range of −0.8 ppm to 0.1 ppm for MMAO-20 and MMAO-3A. Specifically, the ratios of the peaks in the range of −0.03 ppm to 0.025 ppm to peaks found in a range of 0.025 ppm to 0.07 ppm, the ratio of peaks in the range of −0.86 ppm to −0.78 ppm to peaks found in the range of −0.78 ppm to −0.74 ppm, and the ratio of peaks in the range of −0.86 ppm to −0.74 ppm to peaks found in a range of −0.03 ppm to 0.07 ppm are significantly less for MMAO-20 than MMAO-3A. Without being limited by theory, it is believed that the differences in these ratios reflect differences between MMAO-20 and MMAO-3A that are related to the differences observed for ethylene oligomerizations the catalyst systems comprising a chromium compound complex and MMAO-20.

TABLE 6

400 MHz proton NMR Acquisition and Processing Parameters

| Acquisition Parameters | | | | Processing Parameters | | | |
|---|---|---|---|---|---|---|---|
| Pulse Program | zg30 | HDDUTY, % | 20.0 | SI | 65536 | ABSL | 3 |
| Acquisition Mode | DQD | HDRATE | 1 | SF, MHz | 400.1299646 | AZFW, ppm | 0.10000 |
| Size of FID | 65536 | PCPD, μsec | 0 | OFFET, ppm | 16.27670 | AZFE, ppm | 0.10000 |
| Dummy Scans | 2 | V9, % | 5.00 | SR, Hz | −35.42 | ISEN | 128 |
| Number of Scans | 16 | PLW, W | 0 | HZpPT, Hz | 0.122266 | INTSCL | 1 |
| SW, ppm | 20.0254 | PL, -dbW | 1000 | LB, Hz | 0.30 | INTBC | Yes |
| SWH, Hz | 8012.820 | PLSTRT, db | −6 | GB | 0 | ASSFACI | 0 |
| AQ, seconds | 4.0894465 | PLSTEP | 0.1 | SSB | 0 | MI, rel | 0 |
| FIDRES, Hz | 0.244532 | SHAPE | 0 | TM1 | 0 | MAX, rel | 1000.00 |
| FW, Hz | 125000.000 | GRADIENT | 0 | TM2 | 0 | PC | 1.00 |
| ACQT0, μsec | −2.10084 | CAGPASS | 0 | PHC0, degrees | 144.961 | PSIGN | pos |
| RG | 5.6 | AMP, % | 100 | PHC1, degrees | −21.558 | PSCAL | global |

TABLE 6-continued

400 MHz proton NMR Acquisition and Processing Parameters

| Acquisition Parameters | | | | Processing Parameters | | | |
|---|---|---|---|---|---|---|---|
| DW, μsec | 62.400 | 0PROBHD | 5 mm PABBI 1H/D-BB Z-GRD Z828281/0148 | PH__mod | no | SREGLST | 1H.CDCl3 |
| DWOV, μsec | 0.025 | | 0 | ABSG, ppm | 5 | ASSFAC | 0 |
| DECIM | 2496 | QNP | 0 | ABSF1, ppm | 10.00000 | ASSFACX | 0 |
| DSPFIRM | Sharp (standard) | RO, Hz | 4200 | ABSF2, ppm | 0 | ASSWD | 0 |
| GRPDLY | 67.9842 | MASR, Hz | 0 | BCFM, ppm | 1.00000 | F1P, ppm | 0 |
| DIGTYP | DRU | SPINCT | 298.5 | COROFFS, Hz | 0 | F2P, ppm | 0 |
| DIGMOD | digital | TE, K | 1 | BC__ mod, quad | quad | CY [rel] | 15 |
| DR | 22 | PQSCALE | 0 | TDeff | 0 | DATMOD | Proc |
| DDR | 10 | PQPHASE, degree | 4.0000000 | STSR | 0 | DC | 2 |
| DE, μsec | 6.5 | WBSW, MHz | 1024 | STSI | 0 | ALPHA | 0 |
| HPPRGN | normal | WBST | 2H | ME__mod | no | GAMMA | 1 |
| PRGAIN | High | LOCNUC | TRUE | NCOEF | 0 | SIGF1, ppm | 0 |
| DQDMODE | Add | LOCSHIFT | −38 | LPBIN | 0 | SIGF2, ppm | 0 |
| PH__ref, degree | 0 | LOCKPOW, db | 0.1 | TDoff | 0 | F2P, ppm | 0 |
| OVERFLOW | ignore | LTIME, sec | 200 | REVERSE | False | CY [rel] | 15 |
| NOVFLOW | 0 | LFILTER, Hz | −2 | FCOR | 0.5 | ANUMP | proc__1d |
| FRQLO3, Hz | 1.24448e+006 | LGAIN, db | TRUE | PKNL | TRUE | PYNMP | proc.py |
| FRQLO3N | 0 | LOCKED | 1.730 | FT__mod | Fsc | DATMOD | proc |
| NUC1 | 1H | LOCKPPM, ppm | THF | Mdd__mod | Mdd | NOISF1, ppm | 0 |
| O1, Hz | 2470.97 | SOLVENT | au__zg | MddEXP | FALSE | NOISF2, ppm | 0 |
| O1P, ppm | 6.175 | AUNM | PROTON | MddCT__SP | FALSE | SINO | 0 |
| SFO1, MHz | 400.1324710 | EXP | little | MddF180 | FALSE | NSP | 1 |
| BF1, MHz | 400.1300000 | BYTORDA | int | MddNCOMP | 0 | NZP | 0 |
| P, μsec | 10 | YMAX__a | 4.41321e+006 | MddPhase | 0 | | |
| D, sec | 0 | YMIN__a | −5.04402e+006 | MddSRSIZE, ppm | 0 | | |
| IN, sec | 0 | | | | | | |
| INP, μsec | 0 | | | | | | |

TABLE 7

400 MHz proton NMR Integration and Integration Ratios

| | MMAO-20 | MMAO-3A |
|---|---|---|
| NMR Shift Range | | |
| 0.025 ppm to 0.07 ppm, A | 1.0000 | 1.0000 |
| −0.03 ppm to 0.025 ppm, B | 8.9476 | 17.1809 |
| −0.03 ppm to 0.07 ppm, A + B | 9.9476 | 18.1809 |
| −0.78 ppm to −0.74 ppm, C | 4.3735 | 6.6186 |
| −0.86 ppm to −0.78 ppm, D | 15.9846 | 47.7408 |
| −0.86 ppm to −0.74 ppm, C + D | 20.3581 | 54.3594 |
| NMR Shift Ratios | | |
| B:A | 8.9476 | 17.1809 |
| D:C | 3.6548 | 7.2131 |
| (C + D):(A + B) | 2.0465 | 2.9899 |

Example 2: Ethylene Oligomerizations Using Complex A and MMAO-20 or MMAO-3A

Ethylene oligomerizations were performed using Complex A and MMAO-20 or MMAO-3A using the following procedure. In a dry box, a 20 mL glass vial was charged with ethylbenzene (1 g), Complex A (0.0047 mmol), the desired aluminoxane to provide an Al:Cr molar ratio of 702. This solution was then aged for 60 minutes at 50° C. to provide an aged catalyst system mixture. The aged catalyst system mixture was then added to 0.5 L glass charger containing cyclohexane (200 mL).

The glass charger was removed from the dry box and charged into an evacuated 0.5 L stainless steel reactor having an internal temperature of 70° C. Hydrogen was charged to the stainless steel reactor to provide a pressure of 50 psig. Ethylene was then charged to the stainless steel reactor to provide a pressure of 875 psig. The reaction was allowed to proceed for 20 minutes with ethylene being fed on demand to maintain a 875 psig pressure.

At reaction completion, water cooling was applied to the 0.5 L stainless steel reactor using the internal cooling coils. When the stainless steel reactor contents reached 35° C., the unreacted ethylene and hydrogen gas were vented from the stainless steel reactor. A 2 mL sample of the liquid sample was collected, filtered, and analyzed by GC-FID. The stainless steel reactor solids were collected by filtering the liquid solution and cleaning the reactor walls and internal cooling coils. Table 8 provides the MMAOs utilized and the analysis of the oligomer product of the ethylene oligomerization and the calculated productivities and activity of the catalyst systems tested in the ethylene oligomerization runs of Example 2.

TABLE 8

Analysis of Oligomer Product for Example 2

| Run # | 1 | 2 | 3 |
|---|---|---|---|
| Activator | MMAO-20 | MMAO-20 | MMAO-3A |
| Polymer, mass % | 0.03 | 0.09 | 0.02 |
| Liq. NAO Product, g | 108 | 107 | 83 |
| $C_6$, % | 75.1 | 76.3 | 75.4 |
| Trimer Purity, 1-Hexene, % | 98.17 | 98.13 | 98.09 |
| Methylcyclopentane, % | 0.85 | 0.84 | 0.89 |
| Methylenecyclopentane, % | 0.58 | 0.57 | 0.60 |
| $C_8$, % | 21.5 | 20.2 | 21.9 |
| Tetramer Purity, 1-octene % | 98.98 | 99.30 | 98.93 |
| $C_{10}$, % | 2.5 | 2.5 | 1.9 |
| $C_{12+}$, % | 0.9 | 0.9 | 0.8 |
| ($C_6$ + $C_8$) % | 96.5 | 96.6 | 97.3 |
| g ($C_6$ + $C_8$)/g Cr | 425,582 | 422,475 | 327,236 |
| g ($C_6$ + $C_8$)/g Al | 1171 | 1163 | 901 |

As seen in Table 8, productivities of the catalyst system using Complex A and MMAO-20 as an activator exceed 420,000 g $(C_6+C_8)$/g Cr while the catalyst system using Complex A and MMAO-3A as the activator achieved a productivity of approximately 327,000 g $(C_6+C_8)$/g Cr.

Example 3: CSTR Ethylene Oligomerizations with Complex A and MMAO-20 and/or MMAO-3A Continuous stirred tank reactor (CSTR) ethylene oligomerizations were conducted in a 500 mL autoclave reactor using MMAO-3A (ethylene oligomerization run 4), MMAO-20 (ethylene oligomerization run 6), and 50:50 mixture, by mass, of MMAO-3A and MMAO-20 (ethylene oligomerization 5). The catalyst solutions were prepared by charging 75 mg of Complex A to a 40 mL glass vial containing a magnetic stir bar. To the 40 mL glass vial, 10 mL of anhydrous ethylbenzene was added to dissolve Complex A and yield a light blue solution. To this solution, 20 mL of the modified methylaluminoxane (MMAO-20 for run 5 and 6 or MMAO-3A for run 4) was added. The glass vial was then placed on a hot plate and heated for 2 hours at 45° C. with stirring. To a first glass charger was added 155 mL methylcyclohexane and 20 mL the modified methylaluminoxane (MMAO-20 for run 6 or MMAO-3A for run 4 and 5). Note that in the 50:50, by mass, split with MMAO-20 and MMAO-3A run (run 4) the MMAO-20 was added to the 45 mL vial containing Complex A while the MMAO-3A was added to the first glass charger containing 155 mL of methylcyclohexane. The Complex A solution was then added to a glass charger containing methylcyclohexane and the aluminoxane to provide a Complex A solution having a Al:Cr ratio of 700:1. A reactor wash solution was prepared by adding 5 mL of ethylbenzene, 5 mL of neat triethylaluminum, and 68 mL of methylcyclohexane to a second glass charger. The two glass chargers were sealed and removed from the dry box and charged to two separate ISCO syringe pumps attached to a 500 mL autoclave reactor. The Complex A solution was charged to the catalyst system ISCO syringe pump of the reaction system and the reactor wash solution was charged to the reactor wash ISCO syringe pump. A separate ISCO pump also attached to the 500 mL autoclave reactor was charged with dry organic reaction medium, cyclohexane.

The 500 mL autoclave reactor was prepared by first cycling the reactor with three pressure and then vent cycles to 800 psig with dry $N_2$. After the three pressure and vent cycles, an organic liquid medium, cyclohexane, transfer line was connected to the autoclave reactor and the autoclave reactor was filled with dry cyclohexane. The ISCO syringe pump containing the organic reaction medium was then brought online and used to bring the reactor up to a run pressure of 800 psig at a flowrate of 600 grams/hour cyclohexane. The 500 mL autoclave heater/chiller unit was then activated and the autoclave reactor temperature was brought to 70° C. by means of an external oil circulation jacket. Once the desired temperature had been reached, hydrogen flow into the reactor was initiated at 40 sccm via a hydrogen supply line. The 500 mL autoclave reactor was then treated with the reactor wash solution by charging an initial slug of 20 mL of the reactor wash solution to the autoclave reactor. The reactor wash ISCO pump then was set to deliver the reactor pre-wash solution to the reactor at a rate 20 mL/hour for one hour while maintaining the cyclohexane fed rate. The reactor pre-wash solution ISCO pump wash then turned off and the catalyst system ISCO pump was turned on and catalyst system solution was fed to the reactor at a rate of 20 mL/hour. After feeding the catalyst system into the autoclave reactor for 30 minutes, ethylene feed was initiated to the reactor at a rate of 150 grams/hour. The ethylene feed rate was then increased to 350 grams/hour at a rate of 75 grams/hour and then allowed to run at steady state for the duration of the ethylene oligomerization.

The feed rates to the autoclave reactor results in a catalyst system steady state concentration of approximately 0.5 ppm chromium by mass and an aluminoxane steady state concentration of approximately 200 ppm aluminum by mass. Samples of the autoclave reactor effluent were taken every 30 minutes and analyzed by gas-chromatography using a flame ionization detector against the ethylbenzene internal standard. The ethylene oligomerization was terminated by stopping ethylene and catalyst flows to the reactor. The autoclave reactor was then purged with cyclohexane for several minutes, cooled, and depressurized. The polymer samples from inside the reactor were then collected and retained for analysis as fouling polymer. Table 9 provides the catalyst system activation parameters and an analysis of the oligomer product for the ethylene oligomerization runs 4-6 of Example 3.

TABLE 9

Catalyst System Activation Parameters and Oligomer Product Analysis of Ethylene Oligomerization Runs 4-5 of Example 3

| Run # | 4 | 5 | 6 |
|---|---|---|---|
| Activation Temp., ° C. | 50 | 45 | 45 |
| Activation Time, h | 1 | 2 | 2 |
| Activator | MMAO-3A | MMAO-20/3A | MMAO-20 |
| Polymer, g | 1.92 | 0.321 | 0.779 |
| PE, mass % | 0.107 | 0.016 | 0.039 |
| Selectivity, mass % | 89.8 | 90.8 | 92.1 |
| Ethylene Conversion, mass % | 47.7 | 55.6 | 57.8 |
| Trimer Purity-1-Hexene, mass % | 97.1 | 97.5 | 97.9 |
| Tetramer Purity-1-Octene, mass % | 98.5 | 97.2 | 98.5 |
| Cat. Prod., g NAO/g Cr | 214,666 | 310,732 | 332,080 |
| Co-Cat. Prod., g NAO/g Al | 587 | 850 | 909 |
| 1-hexene, mass % | 68.2 | 69.3 | 71.5 |
| 1-octene, mass % | 21.6 | 21.4 | 20.6 |
| $C_{10+}$ Liquid Oligomer Product, mass % | 7.2 | 6.4 | 5.6 |

The data in Table 9 shows that, when the catalyst system is activated with MMAO-20, there is an increase in the ethylene conversion. Without being limited to theory, it is believed that the use of MMAO-20 leads to improved activation of the catalyst system and in turns leads to improved ethylene conversion as compared to the catalyst system using MMAO-3A as the aluminoxane.

Figure 2:
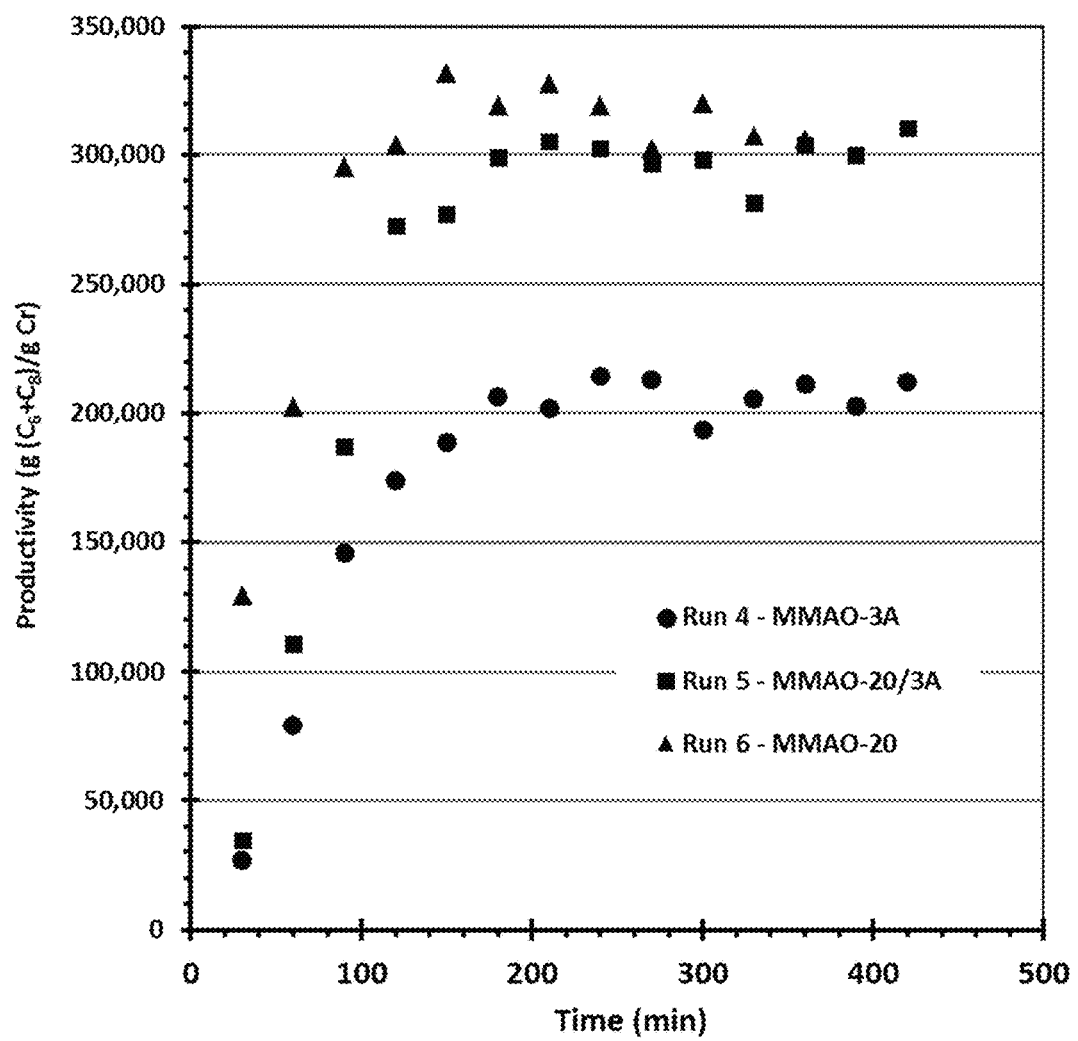
FIG. 2 is a graph of productivity as a function of time for ethylene oligomerization runs 4, 5, and 6 of Example 3.

FIG. 2 provides a graph of the on-line productivity $(g(C_6+C_8)$/g Cr) as a function of time for ethylene oligomerization runs 4, 5, and 6. The graph shows that the productivity of the catalyst system increased when MMAO-20 was utilized as the aluminoxane combined with Complex A.

Figure 3:
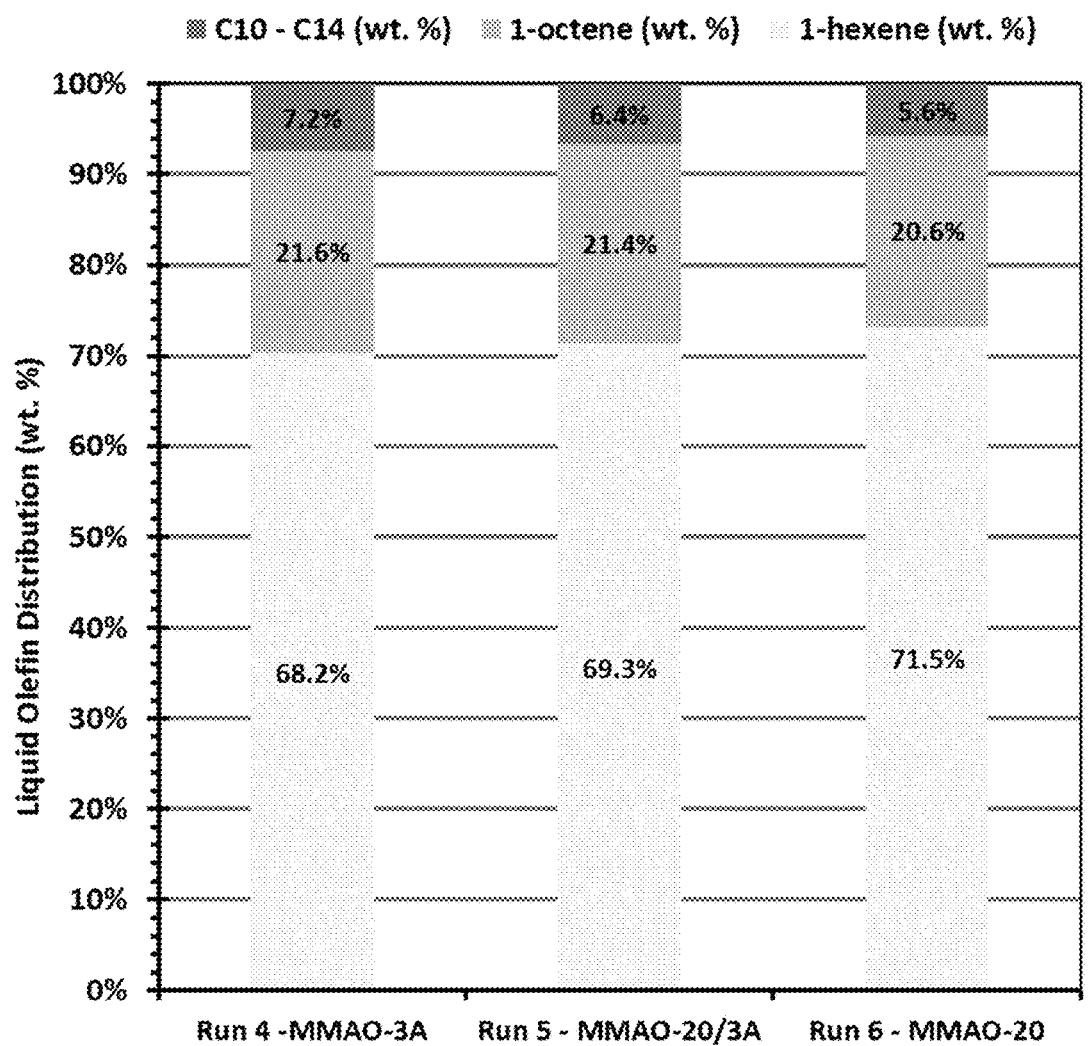
FIG. 3 is a graph of liquid oligomer product carbon number distribution for ethylene oligomerization runs 4, 5, and 6 of Example 3.

FIG. 3 is a graph of the composition of the liquid oligomer product for ethylene oligomerization runs 4, 5, and 6. The comparative catalyst system of Run 4 using MMAO-3A as the aluminoxane has a higher 1-octene production at ~22 mass % yield. However, the increased octene yield comes at the expense of 7 mass % of ethylene feed being converted to the undesirable $C_{10+}$ fraction. In contrast, in Run 6 utilizing MMAO-20 as the aluminoxane, there was a decrease in octene yield, an increase in hexene yield, and a decrease the quantity of $C_{10+}$ produced.

The solids isolated from the reactor on completion of the ethylene oligomerizations, fouling polymer, were analyzed by gel permeation chromatography (GPC) using HDPE polyethylene resin, MARLEX® BHB5003, available from Chevron Phillips Chemicals Company, as the broad molecular weight standard. Calibration samples of MARLEX® BHB5003 can be obtained from Chevron Phillips Chemicals Company, LP.

Figure 4:
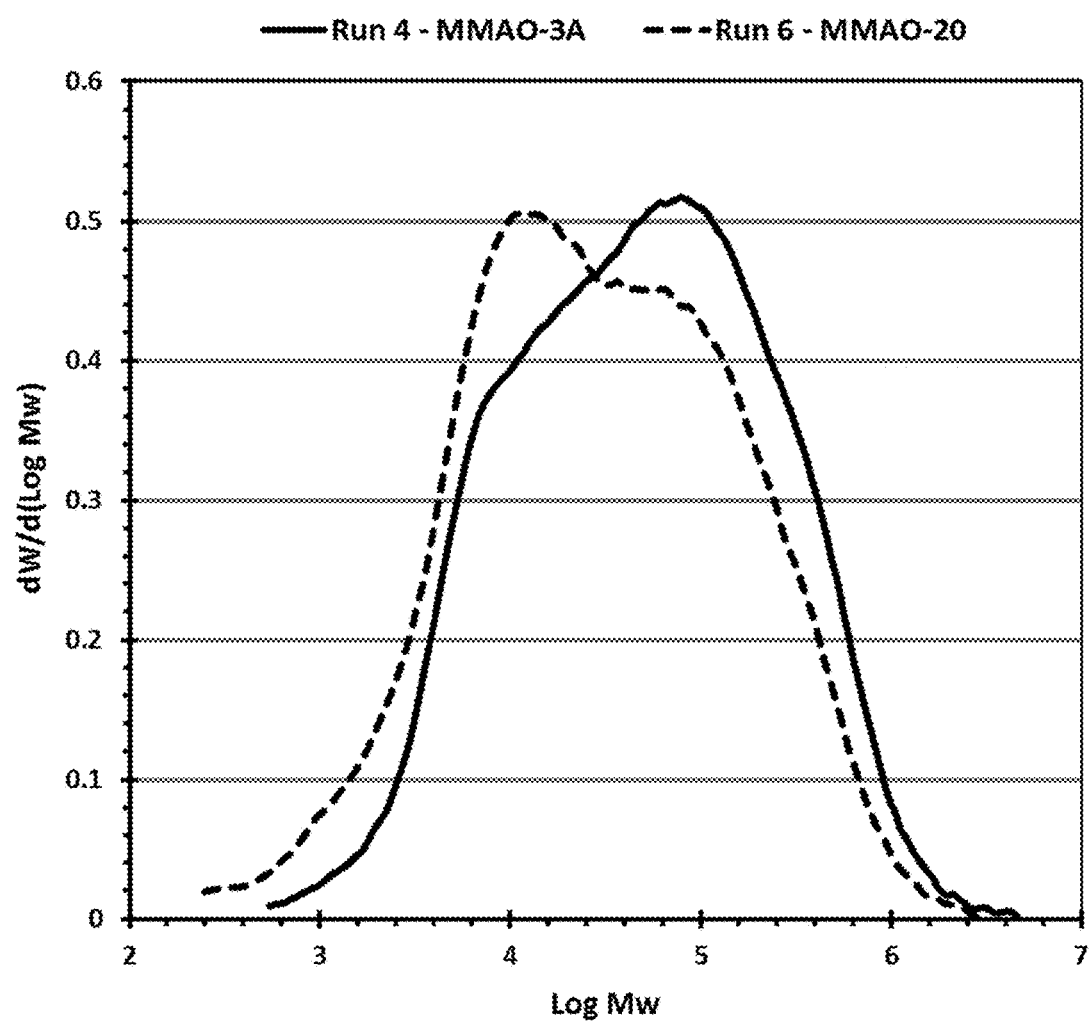
FIG. 4 provides the Mw molecular weight distribution of polymer produced in the ethylene oligomerizations of runs 4 and 6 of Example 3.

The utilization of MMAO-20 as the aluminoxane resulted in a reduction in observed fouling polymer. There was nearly an order of magnitude reduction in fouling polymer when utilizing MMAO-20 as the aluminoxane of the catalyst system as compared to utilizing MMAO-3A as the aluminoxane of the catalyst system: 0.039 and 0.016 mass % fouling polyethylene when using MMAO-20 (Run 6) versus 0.107 mass % fouling polymer under similar conditions when using MMAO-3A (Run 4). FIG. 4 provides a graph of the Mw distribution of the fouling polymer as analyzed by gel permeation chromatography (GPC). FIG. 4 and the data in Table 9 show that the reduction in fouling polymer also coincides with a reduction in the Mw distribution of the fouling polymer (e.g., in the $10^5$-$10^6$ MW range) and a reduction in maximum Mw peak of the fouling polymer. The use of MMAO-20 rather than MMAO-3A in the catalyst system preparation significantly extended run times in continuous stirred tank reactor oligomerization of ethylene.

Example 4: Ethylene Oligomerizations Using Complex A and MMAO-20 or MMAO-3A

Continuous stirred tank reactor (CSTR) ethylene oligomerizations were conducted in a 300 mL autoclave reactor using MMAO-3A or MMAO-20. The catalyst system solutions were prepared by charging 25-30 mg of Complex A to a 40 mL glass vial containing a magnetic stir bar. To the 40 mL glass vial was added 6 mL of anhydrous ethylbenzene to dissolve Complex A. To this solution, was added modified methylaluminoxane (MMAO-20 or MMAO-3A) to provide Complex A solution having an Al:Cr molar ratio of 800:1. The Complex A solution was then placed on a hot plate and heated at the desired temperature for the desired time with stirring. The Complex A solution was added to a glass charger containing the appropriate quantity of methylcyclohexane to obtain a catalyst system solution having a chromium concentration of approximately 0.25 mg/mL. The catalyst system solution was then removed from the drybox and charged to a catalyst system syringe pump attached to the autoclave reactor.

The 300 mL autoclave reactor was prepared for the ethylene oligomerization by pressure testing the reactor with dry nitrogen and then purging the autoclave reactor with dry nitrogen to minimize the presence of air and moisture. Anhydrous cyclohexane (or methylcyclohexane), treated by flow through a molecular sieve and reduced copper oxide bed, was then fed, via a syringe pump, to the autoclave reactor at a rate of 400 grams/hour and the autoclave reactor pressure was allowed to increase to the desired operating pressure in the range of 800 psig to 900 psig. Once the desired pressure was established, the internal autoclave reactor temperature was slowly increased, via an external oil circulation jacket, to the desired temperature in the range of 45° C. to 90° C. Once the desired temperature was established, hydrogen flow into the reactor, via a hydrogen supply line, was initiated and the flow rate was established to obtain the desired hydrogen to chromium molar ratio in the range of 5,000:1 to 20,000:1. A quantity of catalyst solution corresponding to the amount of catalyst added to the reactor in one hour, typically 15.7 mL, was then quickly introduced into the autoclave reactor after which the catalyst system solution was to fed, via the catalyst system syringe pump, to autoclave reactor at a rate of 15.7 mL/hr. After feeding the catalyst system solution into the autoclave reactor for 30 minutes, ethylene feed was initiated to the reactor at a rate of 50 grams/hour. The ethylene fed rate was then increased at a rate of 50 grams/hour per 15 minutes to a target ethylene flow rate of 200 grams/hour and then allowed to run at steady state for the duration of the ethylene oligomerization. Samples of the autoclave reactor effluent were taken every 30 minutes and analyzed by gas-chromatography using a flame ionization detector. The ethylene oligomerization was terminated by stopping ethylene and catalyst flows to the reactor. The autoclave reactor was then purged with cyclohexane for several minutes, cooled, and depressurized. The polymer samples from inside the reactor were then collected and retained for analysis as fouling polymer. Table 10 provides the catalyst system activation parameters and an analysis of the oligomer product for the ethylene oligomerization runs 7-25 of Example 4.

TABLE 10

| Run | 7 | 8 | 9 | 10 | 11 |
|---|---|---|---|---|---|
| Catalyst System Preparation | | | | | |
| MMAO Type | 3A | 3A | 3A | 3A | 3A |
| Activation Temperature, ° C. | 60 | 60 | 60† | 1140 | 2640 |
| Activation Time, Minutes | 60 | | 50† | 23 | 23 |
| Ethylene Oligomerization Run Conditions | | | | | |
| pressure, psig | 875 | 900 | 900 | 900 | 844 |
| Hydrogen Flow Rate, sccm | 9,347 | 9,939 | 9,369 | 6,435 | 8,428 |
| Chromium Conc., ppm by mass | 0.43 | 0.56 | 0.57 | 0.81 | 0.78 |
| Temperature, ° C. | 73.8 | 69.8 | 71.0 | 69.5 | 70.1 |
| Average Residence Time, minutes | | 32 | 29 | 28 | 27 |
| Total Run Time, minutes | 190 | 330 | 270 | 300 | 330 |
| Ethylene Oligomerization Run Results | | | | | |
| Ethylene Conversion, mass % | 17.27 | 16.65 | 19.83 | 26.62 | 29.62 |
| Total Polymer, mass % | 0.0432 | 0.0360 | 0.0030 | 0.0076 | 0.0020 |
| Hexenes, mass % | 75.77 | 74.08 | 71.28 | 72.64 | 72.01 |
| Octenes, mass % | 22.61 | 25.23 | 26.43 | 23.93 | 24.62 |
| $C_{10+}$ Liquid Oligomer Product, mass % | 1.62 | 0.69 | 2.29 | 3.43 | 3.37 |
| $C_6$ + $C_8$ Selectivity, mass % | 98.38 | 99.31 | 97.71 | 96.57 | 96.63 |
| Productivity, g ($C_6$ + $C_8$)/g Cr | 110,000 | 107,000 | 108,000 | 100,000 | 110,000 |

TABLE 10-continued

| Run | 12 | 13 | 14 | 15 | 16 |
|---|---|---|---|---|---|
| Catalyst System Preparation | | | | | |
| MMAO Type | 3A | 3A | A | 3A | 3A |
| Activation Temperature, °C. | 2640 | 60 | 120 | 60 | 60 |
| Activation Time, Minutes | 23 | 60 | 60 | 50 | 45 |
| Ethylene Oligomerization Run Conditions | | | | | |
| pressure, psig | 800 | 800 | 875 | 800 | 900 |
| Hydrogen Flow Rate, sccm | 12,844 | 9,796 | 4,687 | 20,176 | 4,652 |
| Chromium Conc., ppm by mass | 0.87 | 1.13 | 1.12 | 0.48 | 1.13 |
| Temperature, °C. | 73.3 | 70.1 | 70.1 | 70.4 | 69.9 |
| Average Residence Time, minutes | 29 | 28 | 28 | 25 | 30 |
| Total Run Time, minutes | 270 | 291 | 285 | 210 | 300 |
| Ethylene Oligomerization Run Results | | | | | |
| Ethylene Conversion, mass % | 28.69 | 28.77 | 22.00 | 32.13 | 17.98 |
| Total Polymer, mass % | 0.0039 | 0.0020 | 0.0274 | NA | 0.019 |
| Hexenes, mass % | 72.88 | 72.85 | 71.80 | 72.39 | 71.63 |
| Octenes, mass % | 22.90 | 23.66 | 25.34 | 24.50 | 25.89 |
| $C_{10+}$ Liquid Oligomer Product, mass % | 4.22 | 3.49 | 2.96 | 3.77 | 2.49 |
| $C_6 + C_8$ Selectivity, mass % | 95.78 | 96.51 | 97.04 | 96.89 | 97.51 |
| Productivity, g $(C_6 + C_8)$/g Cr | 106,000 | 78,600 | 57,400 | 155,000 | 48,400 |

| Run | 17 | 18 | 19 | 20 | 21 |
|---|---|---|---|---|---|
| Catalyst System Preparation | | | | | |
| MMAO Type | 20 | 20 | 20 | 20 | 20 |
| Activation Temperature, °C. | 45 | 45 | 45 | 45 | 45 |
| Activation Time, Minutes | 120 | 120 | 120 | 120 | 120 |
| Ethylene Oligomerization Run Conditions | | | | | |
| pressure, psig | 900 | 670 | 700 | 700 | 800 |
| Hydrogen Flow Rate, sccm | 4887 | 4731 | 5121 | 5150 | 12387 |
| Chromium Conc., ppm by mass | 1.19 | 0.89 | 1.01 | 0.92 | 0.46 |
| Temperature, °C. | 70.1 | 70.7 | 70.4 | 70.3 | 69.5 |
| Average Residence Time, minutes | 27 | 20 | 22 | 24 | 21 |
| Total Run Time, minutes | 270 | 330 | 315 | 300 | 300 |
| Ethylene Oligomerization Run Results | | | | | |
| Ethylene Conversion, mass % | 46.74 | 53.74 | 57.40 | 62.70 | 61.60 |
| Total Polymer, mass % | 0.0020 | 0.0032 | 0.0013 | 0.0006 | 0.0045 |
| Hexenes, mass % | 72.10 | 73.61 | 74.74 | 76.42 | 77.78 |
| Octenes, mass % | 22.76 | 21.04 | 19.60 | 15.38 | 16.06 |
| $C_{10+}$ Liquid Oligomer Product, mass % | 4.97 | 5.36 | 5.66 | 8.20 | 6.17 |
| $C_6 + C_8$ Selectivity, mass % | 95.03 | 94.64 | 94.34 | 91.80 | 93.83 |
| Productivity, g $(C_6 + C_8)$/g Cr | 126,000 | 192,000 | 151,000 | 210,0005 | 375,000 |

| Run | 22 | 23 | 24 | 25 |
|---|---|---|---|---|
| Catalyst System Preparation | | | | |
| MMAO Type | 20 | 20 | 20 | 20 |
| Activation Temperature, °C. | 45 | 45 | 45 | 45 |
| Activation Time, Minutes | 120 | 120 | 120 | 120 |
| Ethylene Oligomerization Run Conditions | | | | |
| pressure, psig | 800 | 800 | 800 | 800 |
| Hydrogen Flow Rate, sccm | 13096 | 20697 | 19297 | 19595 |
| Chromium Conc., ppm by mass | 0.37 | 0.46 | 0.48 | 0.50 |
| Temperature, °C. | 69.4 | 70.0 | 70.0 | 70.4 |
| Average Residence Time, minutes | 23 | 23 | 22 | 23 |
| Total Run Time, minutes | 360 | 360 | 330 | 360 |
| Ethylene Oligomerization Run Results | | | | |
| Ethylene Conversion, mass % | 49.42 | 51.11 | 54.43 | 56.78 |
| Total Polymer, mass % | 0.0018 | 0.0025 | 0.0018 | 0.0034 |
| Hexenes, mass % | 76.12 | 76.51 | 76.82 | 75.96 |
| Octenes, mass % | 17.93 | 17.31 | 17.12 | 17.67 |
| $C_{10+}$ Liquid Oligomer Product, mass % | 5.95 | 6.19 | 6.06 | 6.38 |
| $C_6 + C_8$ Selectivity, mass % | 94.05 | 93.81 | 93.94 | 93.62 |
| Productivity, g $(C_6 + C_8)$/g Cr | 394,000 | 323,000 | 323,000 | 340,000 |

†Two Stage Activation. First stage was performed at 50° C. for 60 minutes and the second stage was performed at 65° C. for 60 minutes.

Figure 5:
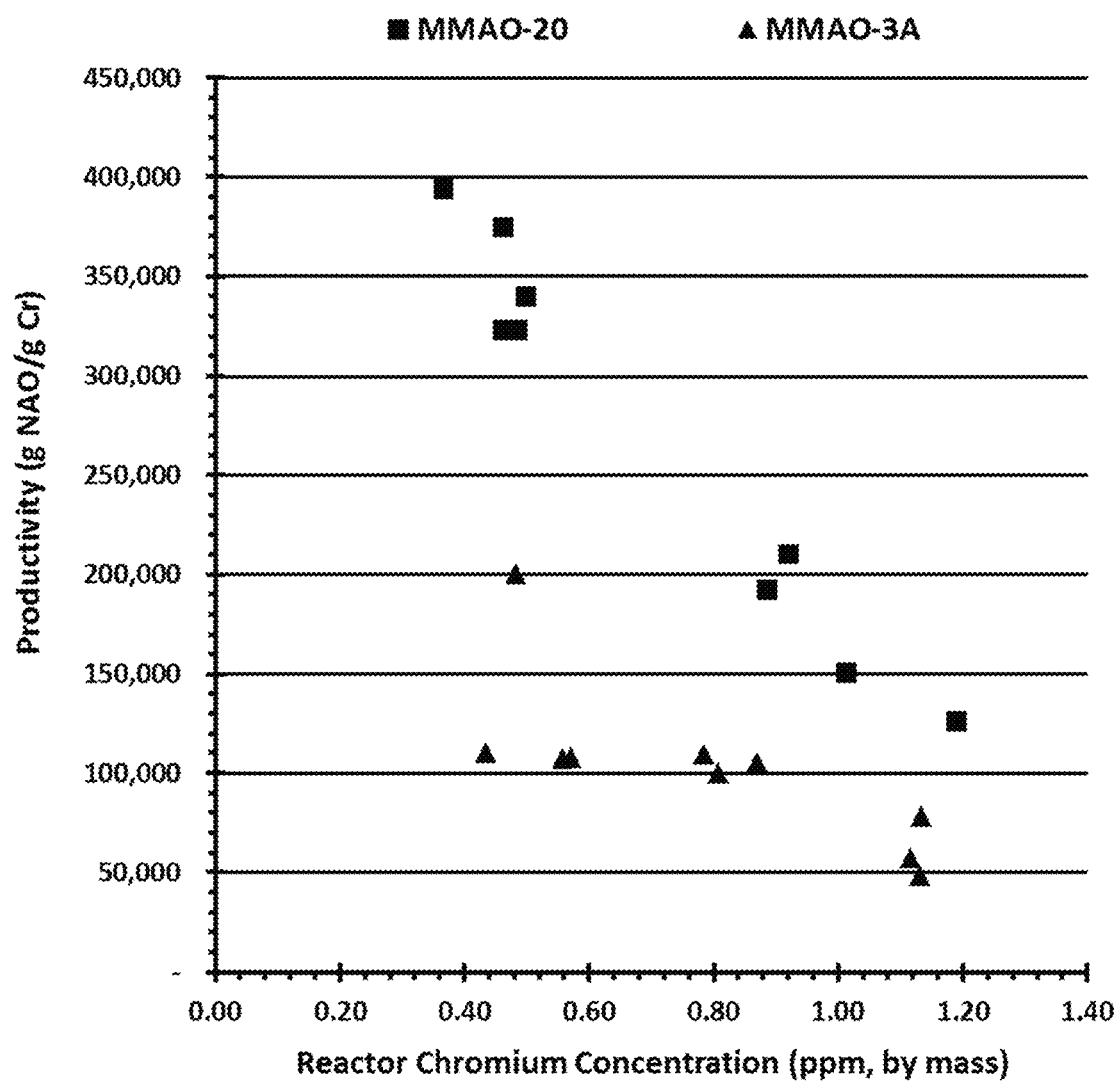
FIG. 5 is a graph of catalyst system productivity as a function of chromium concentration for ethylene oligomerization runs 7-16 using MMAO-3A as the aluminoxane and ethylene oligomerization runs 17-25 using MMAO-20 as the aluminoxane of Example 4.

FIG. 5 provides a graph of the catalyst system productivity as a function of reactor chromium concentration for the ethylene oligomerizations using the catalyst system using complex A and MMAO-3A (Runs 7-16) and the catalyst system using complex A and MMAO-20 (Runs 17-25). The data displayed in FIG. 5 shows that the catalyst system using complex A and MMAO-20 has improved productivity at all of the observed chromium concentrations.

Example 5: Ethylene Oligomerizations Using Complex B MMAO-20 or MMAO-3A

Ethylene oligomerizations were performed using Complex B and MMAO-20 or MMAO-3A using the following procedure. In a dry box, a 20 mL glass vial was charged with ethylbenzene (1 g), Complex B (3.5 mg, 0.0079 mmol), the desired aluminoxane (1.275 g) to provide an Al:Cr molar ratio of 419. This solution was then aged for 30 minutes at room temperature to provide an aged catalyst system mixture. The aged catalyst system mixture was then added to 0.5 L glass charger containing cyclohexane (200 mL).

The glass charger was removed from the dry box and charged into an evacuated 0.5 L stainless steel reactor having an internal temperature of 70° C. Hydrogen was charged to the stainless steel reactor to provide a pressure of 50 psig. Ethylene was then charged to the stainless steel reactor to provide a pressure of 875 psig. The reaction was allowed to proceed for the desired time (34 minutes for the MMAO-20 run and 30 minutes for the MMAO-3A run) with ethylene being fed on demand to maintain a 875 psig pressure.

At reaction completion, water cooling was applied to the 0.5 L stainless steel reactor using the internal cooling coils. When the stainless steel reactor contents reached 35° C., the unreacted ethylene and hydrogen gas were vented from the stainless steel reactor. A 2 mL sample of the liquid sample was collected, filtered, and analyzed by GC-FID. The stainless steel reactor solids were collected by filtering the liquid solution and cleaning the reactor walls and internal cooling coils. Table 11 provides the analysis of the oligomer product of the ethylene oligomerization and the calculated productivities and activity of the catalyst systems tested in ethylene oligomerization runs

TABLE 11

Data from Example 5

| | Run | |
|---|---|---|
| | 26 | 27 |
| | Aluminoxane | |
| | MMAO-20 | MMAO-3A |
| Polymer, g | 20 | 1.14 |
| Polymer, mass % | 28.87 | 11.29 |
| Liquid Oligomer, g | 49 | 9 |
| $C_6$, mass % | 40.2 | 28.3 |
| 1-Hexene, mass % | 31.8 | 21.5 |
| Methylcyclopentane, % | 10.1 | 11.0 |
| Methylenecyclopentane, % | 7.06 | 8.66 |
| Trimer Purity, 1-Hexene, % | 79.2 | 76.0 |
| $C_8$, mass % | 47.9 | 62.9 |
| 1-Octene, mass % | 43.3 | 58.9 |
| Tetramer Purity, 1-Octene, % | 90.4 | 93.6 |
| $C_{10}$, mass % | 6.3 | 5.1 |
| $C_{12}$, mass % | 5.7 | 3.7 |
| $C_{14+}$, mass % | 0.0 | 0.0 |
| $(C_6 + C_8)$, mass % | 88.0 | 91.1 |
| Productivity, g $(C_6 + C_8)$/g Cr | 105,000 | 19,800 |

The use of MMAO-20 (Run 26) led to nearly an order of magnitude increase in productivity from ~19,800 g $(C_6+C_8)$/g Cr to 105,000 g $(C_6+C_8)$/g Cr compared to the use of MMAO-3A (Run 27). Although the absolute polymer production levels increased for Run 26 using MMAO-20, the polymer was easier to manage due to reduced molecular weight.

In summary, the surprising and unexpected results observed in the Examples include:
 i) an improved catalyst system productivity in using MMAO-20 over MMAO-3A (Examples 2-5);
 ii) a reduction in the quantity of polymer produced (Examples 2-5);
 iii) a different molecular weight distribution of the produced solids (Example 3);
 iv) a reduced Mw maximum peak (Example 2);
 iv) increased trimer purity (Examples 2-3, 5); and
 v) increased tetramer purity (Examples 2-3).

Additional Disclosure

Accordingly, the scope of protection is not limited by the description set out above but is only limited by the claims which follow, that scope including all equivalents of the subject matter of the claims. Each and every embodiment and claim is incorporated into the specification as an aspect of the present invention. Thus, the claims are a further description and are an addition to the detailed description of the present invention.

Embodiment 1

A process comprising: contacting a catalyst system, ethylene, and optionally hydrogen to form an oligomer product in a reaction zone, wherein the catalyst system comprises: a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and an aluminoxane; wherein the aluminoxane is characterized by 400 MHz proton NMR in which: (a) the ratio of peaks found in the range of −0.86 ppm to −0.74 ppm to peaks found in a range of −0.03 ppm to 0.07 ppm can be any value described herein; (b) the ratio of peaks found in the range of −0.03 ppm to 0.025 ppm to peaks found in a range of 0.025 ppm to 0.07 ppm can be any value described herein; (c) the ratio of peaks found in the range of −0.86 ppm to −0.78 ppm to peaks found in the range of −0.78 ppm to −0.74 ppm can be any value described herein; or (d) any combination thereof.

Embodiment 2

The process of embodiment 1, wherein the aluminoxane comprises MMAO-20.

Embodiment 3

A process comprising: contacting a catalyst system, ethylene, and optionally hydrogen to form an oligomer product in a reaction zone, wherein the catalyst system comprises a chromium component comprising an $N^2$-phosphinyl amidine chromium compound complex, an $N^2$-phosphinyl formamidine chromium compound complex, an $N^2$-phosphinyl guanidine chromium compound complex, or any combination thereof and an aluminoxane, wherein the aluminoxane comprises MMAO-20.

Embodiment 4

The process of any one of embodiments 1-3, further comprising forming a catalyst system mixture by contacting the chromium component, the aluminoxane, and optionally a solvent to form a catalyst system mixture, aging the catalyst system mixture in the substantial absence of ethylene for a catalyst system mixture aging time to form an aged catalyst system mixture, and contacting the aged catalyst system mixture with the ethylene and optionally hydrogen to form the oligomer product in the reaction zone.

Embodiment 5

The process of embodiment 4, wherein the catalyst system mixture aging time is any catalyst system mixture aging time disclosed herein (e.g., at least 5, 10, 15, or 20 minutes, from 5 minutes to 6 hours, from 10 minutes to 4 hours, from 10 minutes to 2 hours, from 15 minutes to 2 hours, from 20 minutes to 2 hours, or from 20 minutes to one hour).

Embodiment 6

The process of embodiment 4 or 5, wherein relative to the same process utilizing an aluminoxane having (a) a ratio of peaks found in the range of −0.86 ppm to −0.74 ppm to peaks found in a range of −0.03 ppm to 0.07 ppm greater than 2.85; (b) a ratio of peaks found in the range of −0.03 ppm to 0.025 ppm to peaks found in a range of 0.025 ppm to 0.07 ppm greater than 16:1; (c) the ratio of peaks found in the range of −0.86 ppm to −0.78 ppm to peaks found in the range of −0.78 ppm to −0.74 ppm greater than 6.7:1, the catalyst system mixture aging time is reduced.

Embodiment 7

A process comprising: contacting ethylene, an aluminoxane, a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and optionally hydrogen to form an oligomer product in a reaction zone, wherein the aluminoxane is characterized by 400 MHz proton NMR in which: (a) the ratio of peaks found in the range of −0.86 ppm to −0.74 ppm to peaks found in a range of −0.03 ppm to 0.07 ppm can be any value described herein; (b) the ratio of peaks found in the range of −0.03 ppm to 0.025 ppm to peaks found in a range of 0.025 ppm to 0.07 ppm can be any value described herein; (c) the ratio of peaks found in the range of −0.86 ppm to −0.78 ppm to peaks found in the range of −0.78 ppm to −0.74 ppm can be any value described herein; or (d) any combination thereof.

Embodiment 8

The process of embodiment 7, wherein the aluminoxane comprises MMAO-20.

Embodiment 9

A process comprising: contacting ethylene, an aluminoxane, a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and optionally hydrogen to form an oligomer product in a reaction zone, wherein the aluminoxane comprises MMAO-20.

Embodiment 10

The process of any one of embodiments 1-9, wherein the chromium component is an $N^2$-phosphinyl formamidine chromium compound complex having Structure NPFCr1:

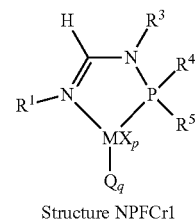

Structure NPFCr1 wherein $R^1$ is a $C_1$ to $C_{30}$ organyl group; $R^3$ is hydrogen or a $C_1$ to $C_{30}$ organyl group consisting essentially of inert functional groups; $R^4$ and $R^5$ each independently are $C_1$ to $C_{30}$ organyl groups consisting essentially of inert functional groups; $CrX_p$ represents a chromium compound where X is a monoanion, and p is an integer from 2 to 6; Q is a neutral ligand; and q ranges from 0 to 6.

Embodiment 11

The process of any one of embodiments 1-9, wherein the chromium component is an $N^2$-phosphinyl amidine chromium compound complex having Structure NPACr1 or Structure NPACr2:

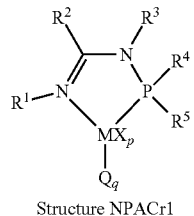 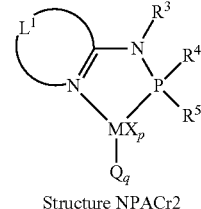

Structure NPACr1    Structure NPACr2 wherein $R^1$ is a $C_1$ to $C_{30}$ organyl group; $R^2$ is a $C_1$ to $C_{30}$ organyl groups consisting essentially of inert functional groups; $R^3$ is hydrogen or a $C_1$ to $C_{30}$ organyl group consisting essentially of inert functional groups; $R^4$ and $R^5$ each independently are $C_1$ to $C_{30}$ organyl groups consisting essentially of inert functional groups; $L^1$ is a $C_3$ to $C_{30}$ organylene group; $CrX_p$ represents a chromium compound where X is a monoanion, and p is an integer from 2 to 6; Q is a neutral ligand; and q ranges from 0 to 6.

Embodiment 12

The process of any one of embodiments 1-9, wherein the chromium component is an $N^2$-phosphinyl guanidine chromium compound complex having Structure GuCr1, Structure GuCr2, Structure GuCr3, Structure GuCr4, or Structure GuCr5:

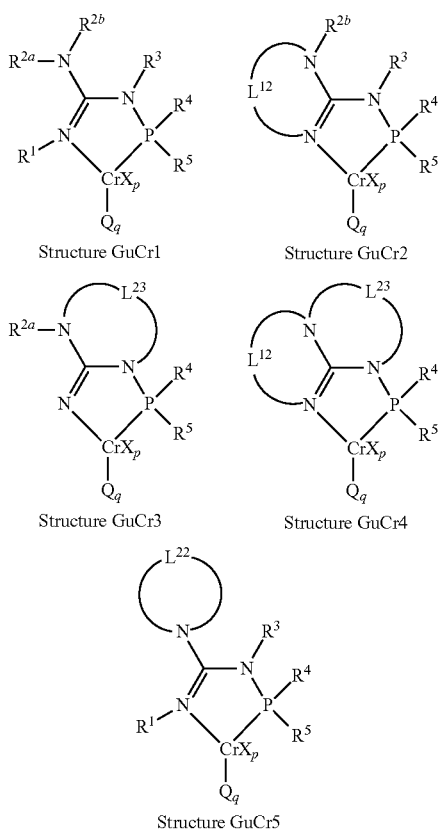

Structure GuCr1

Structure GuCr2

Structure GuCr3

Structure GuCr4

Structure GuCr5 wherein $R^1$ is a $C_1$ to $C_{30}$ organyl group; $R^{2a}$ and $R^{2b}$ independently are $C_1$ to $C_{30}$ organyl groups consisting essentially of inert functional groups; $R^3$ is hydrogen or a $C_1$ to $C_{30}$ organyl group consisting essentially of inert functional groups; $R^4$ and $R^5$ each independently are $C_1$ to $C_{30}$ organyl groups consisting essentially of inert functional groups; $L^{12}$ and $L^{23}$ each independently are $C_2$ to $C_{20}$ organylene groups consisting essentially of inert functional groups; $L^{22}$ is a $C_3$ to $C_{20}$ organylene group consisting essentially of inert functional groups; $CrX_p$ represents a chromium compound where X is a monoanion, and p is an integer from 2 to 6; Q is a neutral ligand; and q ranges from 0 to 6.

Embodiment 13

The process of any one of embodiments 1-12, wherein relative to the same process utilizing a different aluminoxane: (a) a ($C_6+C_8$) productivity (defined as the grams of ($C_6+C_8$) product produced per gram of chromium) is increased; (b) a liquid oligomer portion of the oligomer product comprises a reduced amount of $C_{10}$ to $C_{18}$ oligomers; (c) the oligomer product comprises a polymer having a lower Mw; (d) a Mw maximum peak of the polymer is reduced, (e) a quantity of polymer in the oligomer product is reduced; or (0 any combination thereof.

Embodiment 14

The process of embodiment 13, wherein there is at least a 10, 20, or 30% increase in the $C_6+C_8$ productivity.

Embodiment 15

The process of embodiment 13 or 14, wherein there is at least a 5, 10, 15, or 20% reduction in the $C_{10}$ to $C_{18}$ oligomers in the oligomer product.

Embodiment 16

The process of any one of embodiments 13-15, wherein there is at least a 10, 15, 20, or 25% reduction in the molecular weight of the Mw maximum peak of the polymer.

Embodiment 17

The process of any one of embodiments 13-16, wherein there is at least a 10, 15, 20, or 25% a reduction in the polymer Mw.

Embodiment 18

The process of any one of embodiments 13-17, wherein there is at least a 30, 40, 50, or 60% reduction in the quantity of polymer in the oligomer product.

Embodiment 19

The process of any one of embodiments 1-18, wherein relative to the same process utilizing a different aluminoxane, a reaction zone on-line for the process is increased.

Embodiment 20

The process of any one of embodiments 1-19, wherein, relative to the same process utilizing a different aluminoxane, an amount of 1-hexene in the $C_6$ fraction of the oligomer product is increased (e.g., there is a 0.2, 0.3, 0.4, 0.5, or 0.6% increase in the amount 1-hexene the $C_6$ fraction of the oligomer product).

Embodiment 21

The process of any one of embodiments 1-20, wherein, relative to the same process utilizing a different aluminoxane, a hexene selectivity is increased (e.g., there is a 1, 2, 3, or 4% increase in the 1-hexene selectivity).

Embodiment 22

The process of any one of embodiments 1-21, wherein, relative to the same process utilizing a different aluminoxane, a ($C_6+C_8$) selectivity is increased (e.g., there is a 0.2, 0.3, 0.4, 0.5, or 0.6% increase in the ($C_6+C_8$) selectivity).

Embodiment 23

The process of any one of embodiments 13-22, wherein the different aluminoxane comprises (or consists essentially of, or consists of) an aluminoxane having (a) a ratio of peaks found in the range of −0.86 ppm to −0.74 ppm to peaks found in a range of −0.03 ppm to 0.07 ppm greater than 2.85, (b) a ratio of peaks found in the range of −0.03 ppm to 0.025 ppm to peaks found in a range of 0.025 ppm to 0.07 ppm greater than 16:1, (c) the ratio of peaks found in the range of −0.86 ppm to −0.78 ppm to peaks found in the range of −0.78 ppm to −0.74 ppm greater than 6.7:1, or d) or any combination thereof; or alternatively comprises (or consists essentially of, or consists of) MMAO-3A.

Embodiment 24

The process of any one of embodiments 1-23, wherein the reaction zone has an aluminum of the aluminoxane to chromium of the chromium component molar ratio in a range of from 100:1 to 2,000:1.

Embodiment 25

The process of any one of embodiments 1-24, wherein the oligomer product is formed at a temperature in a range of from 0° C. to 200° C.

Embodiment 26

The process of any one of embodiments 1-25, wherein the oligomer product is formed at an ethylene partial pressure in a range of from 100 psi (689 kPa) to 2,000 psi (13.8 MPa).

Embodiment 27

The process of any one of embodiments 1-26, wherein the reaction zone has a temperature in a range of from 50° C. to 100° C., an ethylene:chromium of the chromium component mass ratio in the range of from 250,000:1 to 1,500,000:1, and a hydrogen:chromium of the chromium component mass ratio in the range of from 100:1 to 10,000:1 based upon a total mass in the reaction zone.

Embodiment 28

The process of any one of embodiments 1-27, wherein the oligomer product comprises hexenes and/or octenes; or alternatively, comprises (a) at least 70 wt. % hexenes, (b) at least 70 wt. % octenes, or (c) a total of at least 70 wt. % hexenes and octenes.

Embodiment 29

The process of any one of embodiments 1-28, wherein a reaction zone effluent comprising the oligomer product is removed from the reaction zone.

Embodiments 30

The process of embodiment 29, wherein hexenes and/or octenes are separated from the reaction zone effluent.

Embodiment 31

The process of embodiment 29 or 30, wherein the ethylene, the catalyst system, and optionally, hydrogen are periodically or continuously introduced into the reaction zone, and a reaction zone effluent comprising the oligomer product is periodically or continuously removed from the reaction zone.

Embodiment 32

The process of any one of embodiments 1-31 further comprising: (I) contacting ethylene with at least a portion of an organic reaction medium prior to contacting the ethylene with the catalyst system, and/or (II) introducing or feeding the ethylene into the reaction zone separately from the catalyst system.

Embodiment 33

The process of embodiment 32, wherein a mass of polymer per mass of oligomer in the reaction zone is less than a mass of polymer per mass of oligomer in the reaction zone of an otherwise similar process which does not: (I) contact ethylene with at least a portion of the organic reaction medium prior to contact of the ethylene with the catalyst system, and/or (II) introduce or feed the ethylene into the reaction zone separately from the catalyst system.

Embodiment 34

The process of any one of embodiments 1-33, wherein the reaction zone comprises one or more reactors selected from autoclave reactors, continuous stirred tank reactors, loop reactors, gas phase reactors, solution reactors, tubular reactors, recycle reactors, bubble reactors, or a combination thereof.

The invention illustratively disclosed herein suitably can be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above can vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

All publications and patents mentioned herein are incorporated herein by reference. The publications and patents mentioned herein can be utilized for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Therefore, the present invention is well adapted to attain the ends and advantages mentioned as well as those that are inherent therein. This concludes the detailed description. The particular embodiments disclosed above are illustrative only, as the invention can be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above can be altered or modified and all such variations are considered within the scope and spirit of the invention. Accordingly, the protection sought herein is as set forth in the claims herein.

What is claimed is:

1. A process comprising: contacting a catalyst system, ethylene, and optionally hydrogen to form an oligomer product in a reaction zone, wherein the catalyst system comprises: a chromium component comprising an N²-phosphinyl amidine chromium compound complex, an N²-phosphinyl formamidine chromium compound complex, an N²-phosphinyl guanidine chromium compound complex, or any combination thereof, and a modified methylaluminoxane (MMAO); wherein the MMAO is characterized by 400 MHz proton NMR in which: (a) a ratio of peak areas found in a range of −0.86 ppm to −0.74 ppm to peak areas found in a range of −0.03 ppm to 0.07 ppm is less than or equal to 2.8:1; (b) a ratio of peak areas found in a range of −0.03 ppm to 0.025 ppm to peak areas found in a range of 0.025 ppm to 0.07 ppm is less than or equal to 15:1; and (c) a ratio of peak areas found in a range of −0.86 ppm to −0.78 ppm to peak areas found in the range −0.78 ppm to −0.74 ppm is less than or equal to 6.5:1.

2. The process of claim 1, further comprising forming a catalyst system mixture by contacting the chromium component, the MMAO, and optionally a solvent to form a catalyst system mixture, aging the catalyst system mixture in the substantial absence of ethylene for a catalyst system mixture aging time to form an aged catalyst system mixture, and contacting the aged catalyst system mixture with the ethylene and optionally hydrogen to form the oligomer product in the reaction zone.

3. The process of claim 2, wherein relative to the same process utilizing an MMAO having (a) the ratio of peak areas found in the range of −0.86 ppm to −0.74 ppm to peak areas found in a range of −0.03 ppm to 0.07 ppm greater than 2.85; (b) the ratio of peak areas found in the range of −0.03 ppm to 0.025 ppm to peak areas found in a range of 0.025 ppm to 0.07 ppm greater than 16:1; (c) the ratio of peak areas found in the range of −0.86 ppm to −0.78 ppm to peak areas found in the range of −0.78 ppm to −0.74 ppm greater than 6.7:1; or any combination thereof, the catalyst system mixture aging time is reduced.

4. The process of claim 1, wherein the chromium component is an N²-phosphinyl formamidine chromium compound complex having Structure NPFCr1:

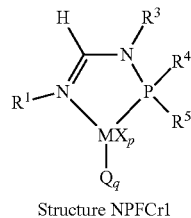

Structure NPFCr1 wherein $R^1$ is a $C_1$ to $C_{30}$ organyl group; $R^3$ is hydrogen or a $C_1$ to $C_{30}$ organyl group consisting essentially of inert functional groups; $R^4$ and $R^5$ each independently are $C_1$ to $C_{30}$ organyl groups consisting essentially of inert functional groups; $CrX_p$ represents a chromium compound where X is a monoanion, and p is an integer from 2 to 6; Q is a neutral ligand; and q ranges from 0 to 6.

5. The process of claim 1, wherein the chromium component is an N²-phosphinyl amidine chromium compound complex having Structure NPACr1 or Structure NPACr2:

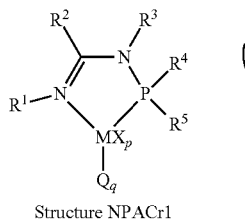 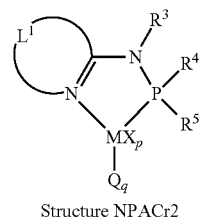

Structure NPACr1　　　Structure NPACr2 wherein $R^1$ is a $C_1$ to $C_{30}$ organyl group; $R^2$ is a $C_1$ to $C_{30}$ organyl groups consisting essentially of inert functional groups; $R^3$ is hydrogen or a $C_1$ to $C_{30}$ organyl group consisting essentially of inert functional groups; $R^4$ and $R^5$ each independently are $C_1$ to $C_{30}$ organyl groups consisting essentially of inert functional groups; $L^1$ is a $C_3$ to $C_{30}$ organylene group; $CrX_p$ represents a chromium compound where X is a monoanion, and p is an integer from 2 to 6; Q is a neutral ligand; and q ranges from 0 to 6.

6. The process of claim 1, wherein the chromium component is an N²-phosphinyl guanidine chromium compound complex having Structure GuCr1, Structure GuCr2, Structure GuCr3, Structure GuCr4, or Structure GuCr5:

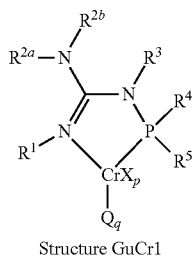 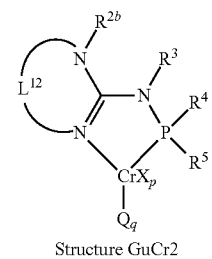

Structure GuCr1　　　Structure GuCr2

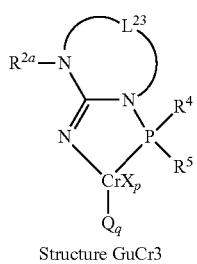 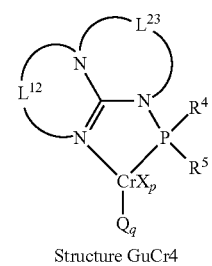

Structure GuCr3　　　Structure GuCr4

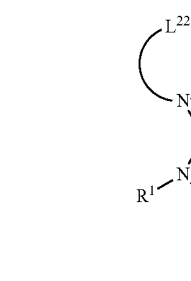

Structure GuCr5 wherein $R^1$ is a $C_1$ to $C_{30}$ organyl group; $R^{2a}$ and $R^{2b}$ independently are $C_1$ to $C_{30}$ organyl groups consisting essentially of inert functional groups; $R^3$ is hydrogen or a $C_1$ to $C_{30}$ organyl group consisting essentially of inert functional groups; $R^4$ and $R^5$ each independently are $C_1$ to $C_{30}$ organyl groups consisting essentially of inert functional groups; $L^{12}$ and $L^2$ each independently are $C_2$ to $C_{20}$ organylene groups consisting essentially of inert functional groups; $L^{22}$ is a $C_3$ to $C_{20}$ organylene group consisting essentially of inert functional groups; $CrX_p$ represents a chromium compound where X is a monoanion, and p is an integer from 2 to 6; Q is a neutral ligand; and q ranges from 0 to 6.

7. The process of claim 1, wherein relative to the same process utilizing an MMAO having (a) the ratio of peak areas found in the range of −0.86 ppm to −0.74 ppm to peak areas found in a range of −0.03 ppm to 0.07 ppm greater than 2.85; (b) the ratio of peak areas found in the range of −0.03 ppm to 0.025 ppm to peak areas found in a range of 0.025 ppm to 0.07 ppm greater than 16:1; (c) the ratio of peak areas found in the range of −0.86 ppm to −0.78 ppm to peak areas found in the range of −0.78 ppm to −0.74 ppm greater than 6.7:1; or any combination thereof: (a) a catalyst system $(C_6+C_8)$ productivity is increased; (b) a liquid oligomer portion of the oligomer product comprises a reduced amount of $C_{10}$ to $C_{18}$ oligomers; (c) the oligomer product comprises a polymer having a lower Mw; (d) a Mw maximum peak of the polymer is reduced, (e) a quantity of polymer in the oligomer product is reduced; or (f) any combination thereof.

8. The process of claim 7, wherein there is (a) at least a 10% increase in the catalyst system $(C_6+C_8)$ productivity; (b) at least a 5% reduction in the C10 to C18 oligomers in the liquid oligomer product; (c) at least a 10% reduction in the polymer Mw; (d) at least a 10% reduction in the molecular weight of the Mw maximum peak of the polymer, (e) a 30% reduction in the quantity of polymer in the oligomer product; or (f) any combination thereof.

9. The process of claim 1, wherein relative to the same process utilizing an MMAO having (a) the ratio of peak areas found in the range of −0.86 ppm to −0.74 ppm to peak areas found in a range of −0.03 ppm to 0.07 ppm greater than 2.85; (b) the ratio of peak areas found in the range of −0.03 ppm to 0.025 ppm to peak areas found in a range of 0.025 ppm to 0.07 ppm greater than 16:1; (c) the ratio of peak areas found in the range of −0.86 ppm to −0.78 ppm to peak areas found in the range of −0.78 ppm to −0.74 ppm greater than 6.7:1; or any combination thereof, a reaction zone on-line for the process is increased.

10. The process of claim 1, wherein, relative to the same process utilizing an MMAO having (a) the ratio of peak areas found in the range of −0.86 ppm to −0.74 ppm to peak areas found in a range of −0.03 ppm to 0.07 ppm greater than 2.85; (b) the ratio of peak areas found in the range of −0.03 ppm to 0.025 ppm to peak areas found in a range of 0.025 ppm to 0.07 ppm greater than 16:1; (c) the ratio of peak areas found in the range of −0.86 ppm to −0.78 ppm to peak areas found in the range of −0.78 ppm to −0.74 ppm greater than 6.7:1; or any combination thereof, an amount of 1-hexene in the $C_6$ fraction of the oligomer product is increased.

11. The process of claim 1, wherein, relative to the same process utilizing an MMAO having (a) the ratio of peak areas found in the range of −0.86 ppm to −0.74 ppm to peak areas found in a range of −0.03 ppm to 0.07 ppm greater than 2.85; (b) the ratio of peak areas found in the range of −0.03 ppm to 0.025 ppm to peak areas found in a range of 0.025 ppm to 0.07 ppm greater than 16:1; (c) the ratio of peak areas found in the range of −0.86 ppm to −0.78 ppm to peak areas found in the range of −0.78 ppm to −0.74 ppm greater than 6.7:1; or any combination thereof, a hexene selectivity is increased.

12. The process of claim 1, wherein, relative to the same process utilizing an MMAO having (a) the ratio of peak areas found in the range of −0.86 ppm to −0.74 ppm to peak areas found in a range of −0.03 ppm to 0.07 ppm greater than 2.85; (b) the ratio of peak areas found in the range of −0.03 ppm to 0.025 ppm to peak areas found in a range of 0.025 ppm to 0.07 ppm greater than 16:1; (c) the ratio of peak areas found in the range of −0.86 ppm to −0.78 ppm to peak areas found in the range of −0.78 ppm to −0.74 ppm greater than 6.7:1; or any combination thereof, a $(C_6+C_8)$ selectivity is increased.

13. The process of claim 1 further comprising: (I) contacting ethylene with at least a portion of an organic reaction medium prior to contacting the ethylene with the catalyst system, and/or (II) introducing or feeding the ethylene into the reaction zone separately from the catalyst system.

14. The process of claim 1, wherein the MMAO is characterized by 400 MHz proton NMR in which: (a) the ratio of peak areas found in the range of −0.86 ppm to −0.74 ppm to peak areas found in the range of −0.03 ppm to 0.07 ppm is less than or equal to 2.8:1; (b) the ratio of peak areas found in the range of −0.03 ppm to 0.025 ppm to peak areas found in the range of 0.025 ppm to 0.07 ppm is less than or equal to 15:1; and (c) the ratio of peak areas found in the range of −0.86 ppm to −0.78 ppm to peak areas found in the range −0.78 ppm to −0.74 ppm is less than or equal to 6.5:1.

15. A process comprising: contacting ethylene, a modified methylaluminoxane (MMAO), a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and optionally hydrogen to form an oligomer product in a reaction zone, wherein the MMAO is characterized by 400 MHz proton NMR in which: (a) a ratio of peak areas found in a range of −0.86 ppm to −0.74 ppm to peak areas found in a range of −0.03 ppm to 0.07 ppm is less than or equal to 2.8:1; (b) a ratio of peak areas found in a range of −0.03 ppm to 0.025 ppm to peak areas found in a range of 0.025 ppm to 0.07 ppm is less than or equal to 15:1; and(c) a ratio of peak areas found in a range of −0.86 ppm to −0.78 ppm to peak areas found in the range of −0.78 ppm to −0.74 ppm is less than or equal to 6.5:1.

16. The process of claim 15, wherein the chromium component is an $N^2$-phosphinyl formamidine chromium compound complex having Structure NPFCr1:

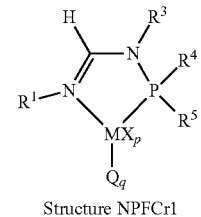

Structure NPFCr1 wherein $R^1$ is a $C_1$ to $C_{30}$ organyl group; $R^3$ is hydrogen or a $C_1$ to $C_{30}$ organyl group consisting essentially of inert functional groups; $R^4$ and $R^5$ each independently are $C_1$ to $C_{30}$ organyl groups consisting essentially of inert functional groups; $CrX_p$ represents a chromium compound where X is a monoanion, and p is an integer from 2 to 6; Q is a neutral ligand; and q ranges from 0 to 6.

17. The process of claim 15, wherein the chromium component is an $N^2$-phosphinyl amidine chromium compound complex having Structure NPACr1 or Structure NPACr2:

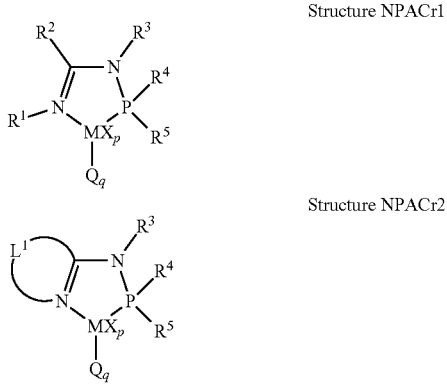

Structure NPACr1

Structure NPACr2 wherein $R^1$ is a $C_1$ to $C_{30}$ organyl group; $R^2$ is a $C_1$ to $C_{30}$ organyl groups consisting essentially of inert functional groups; $R^3$ is hydrogen or a $C_1$ to $C_{30}$ organyl group consisting essentially of inert functional groups; $R^4$ and $R^5$ each independently are $C_1$ to $C_{30}$ organyl groups consisting essentially of inert functional groups; $L^1$ is a $C_3$ to $C_{30}$ organylene group; $CrX_p$ represents a chromium compound where X is a monoanion, and p is an integer from 2 to 6; Q is a neutral ligand; and q ranges from 0 to 6.

18. The process of claim 15, wherein the chromium component is an $N^2$-phosphinyl guanidine chromium compound complex having Structure GuCr1, Structure GuCr2, Structure GuCr3, Structure GuCr4, or Structure GuCr5:

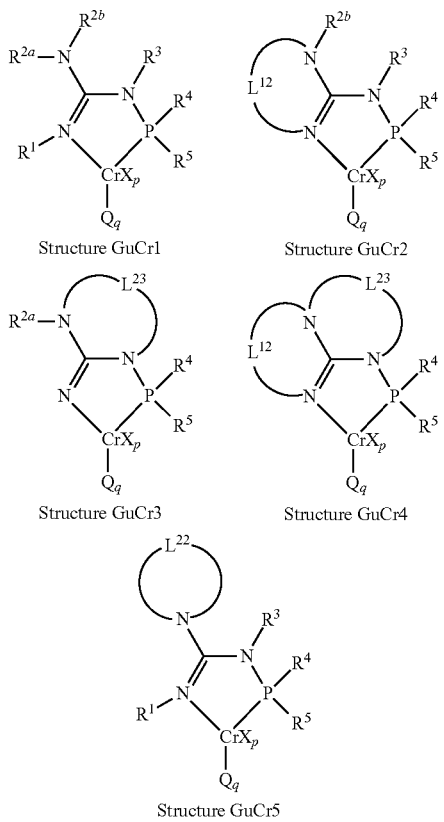

Structure GuCr1

Structure GuCr2

Structure GuCr3

Structure GuCr4

Structure GuCr5 wherein $R^1$ is a $C_1$ to $C_{30}$ organyl group; $R^{2a}$ and $R^{2b}$ independently are $C_1$ to $C_{30}$ organyl groups consisting essentially of inert functional groups; $R^3$ is hydrogen or a $C_1$ to $C_{30}$ organyl group consisting essentially of inert functional groups; $R^4$ and $R^5$ each independently are $C_1$ to $C_{30}$ organyl groups consisting essentially of inert functional groups; $L^{12}$ and $L^{23}$ each independently are $C_2$ to $C_{20}$ organylene groups consisting essentially of inert functional groups; $L^{22}$ is a $C_3$ to $C_{20}$ organylene group consisting essentially of inert functional groups; $CrX_p$ represents a chromium compound where X is a monoanion, and p is an integer from 2 to 6; Q is a neutral ligand; and q ranges from 0 to 6.

19. The process of claim 15, wherein relative to the same process utilizing an MMAO having (a) the ratio of peak areas found in the range of −0.86 ppm to −0.74 ppm to peak areas found in a range of −0.03 ppm to 0.07 ppm greater than 2.85; (b) the ratio of peak areas found in the range of −0.03 ppm to 0.025 ppm to peak areas found in a range of 0.025 ppm to 0.07 ppm greater than 16:1; (c) the ratio of peak areas found in the range of −0.86 ppm to −0.78 ppm to peak areas found in the range of −0.78 ppm to −0.74 ppm greater than 6.7:1; or any combination thereof: (a) a catalyst system ($C_6+C_8$) productivity is increased; (b) a liquid oligomer portion of the oligomer product comprises a reduced amount of $C_{10}$ to $C_{18}$ oligomers: (c) the oligomer product comprises a polymer having a lower Mw; (d) a Mw maximum peak of the polymer is reduced, (e) a quantity of polymer in the oligomer product is reduced; or (f) any combination thereof.

20. The process of claim 15, wherein relative to the same process utilizing an MMAO having (a) the ratio of peak areas found in the range of −0.86 ppm to −0.74 ppm to peak areas found in a range of −0.03 ppm to 0.07 ppm greater than 2.85; (b) the ratio of peak areas found in the range of −0.03 ppm to 0.025 ppm to peak areas found in a range of 0.025 ppm to 0.07 ppm greater than 16:1; (c) the ratio of peak areas found in the range of −0.86 ppm to −0.78 ppm to peak areas found in the range of −0.78 ppm to −0.74 ppm greater than 6.7:1; or any combination thereof, an amount of 1-hexene in the $C_6$ fraction of the oligomer product is increased.

21. The process of claim 15, wherein relative to the same process utilizing an MMAO having (a) the ratio of peak areas found in the range of −0.86 ppm to −0.74 ppm to peak areas found in a range of −0.03 ppm to 0.07 ppm greater than 2.85; (b) the ratio of peak areas found in the range of −0.03 ppm to 0.025 ppm to peak areas found in a range of 0.025 ppm to 0.07 ppm greater than 16:1; (c) the ratio of peak areas found in the range of −0.86 ppm to −0.78 ppm to peak areas found in the range of −0.78 ppm to −0.74 ppm greater than 6.7:1; or any combination thereof, a hexene selectivity is increased.

22. The process of claim 15, wherein relative to the same process utilizing an MMAO having (a) the ratio of peak areas found in the range of −0.86 ppm to −0.74 ppm to peak areas found in a range of −0.03 ppm to 0.07 ppm greater than 2.85; (b) the ratio of peak areas found in the range of −0.03 ppm to 0.025 ppm to peak areas found in a range of 0.025 ppm to 0.07 ppm greater than 16:1; (c) the ratio of peak areas found in the range of −0.86 ppm to −0.78 ppm to peak areas found in the range of −0.78 ppm to −0.74 ppm greater than 6.7:1; or any combination thereof, a ($C_6+C_8$) selectivity is increased.

23. The process of claim 15 further comprising: (I) contacting ethylene with at least a portion of an organic reaction medium prior to contacting the ethylene with the catalyst system, and/or (II) introducing or feeding the ethylene into the reaction zone separately from the catalyst system.

24. The process of claim 15, wherein the MMAO is characterized by 400 MHz proton NMR in which: (a) the ratio of peak areas found in the range of −0.86 ppm to −0.74 ppm to peak areas found in the range of −0.03 ppm to 0.07 ppm is less than or equal to 2.8:1; (b) the ratio of peak areas found in the range of −0.03 ppm to 0.025 ppm to peak areas found in the range of 0.025 ppm to 0.07 ppm is less than or equal to 15:1; and (c) the ratio of peak areas found in the range of −0.86 ppm to −0.78 ppm to peak areas found in the range −0.78 ppm to −0.74 ppm is less than or equal to 6.5:1.

* * * * *